United States Patent
Jones et al.

(10) Patent No.: US 11,454,611 B2
(45) Date of Patent: Sep. 27, 2022

(54) SPECTROMETRIC ANALYSIS OF PLANTS

(71) Applicant: Micromass UK Limited, Wilmslow (GB)

(72) Inventors: Emrys Jones, Manchester (GB); Sara Stead, Wilmslow (GB); Julia Balog, Solymar (HU); Richard Schafer, Somberek (HU)

(73) Assignee: Micromass UK Limited, Wilmslow (GB)

( * ) Notice: Subject to any disclaimer, the term of this patent is extended or adjusted under 35 U.S.C. 154(b) by 712 days.

(21) Appl. No.: 16/093,506

(22) PCT Filed: Apr. 13, 2017

(86) PCT No.: PCT/GB2017/051050
§ 371 (c)(1),
(2) Date: Oct. 12, 2018

(87) PCT Pub. No.: WO2017/178833
PCT Pub. Date: Oct. 19, 2017

(65) Prior Publication Data
US 2021/0215638 A1    Jul. 15, 2021

(30) Foreign Application Priority Data
Apr. 14, 2016   (GB) .................................. 1606558

(51) Int. Cl.
*H01J 49/00*   (2006.01)
*G01N 27/623*   (2021.01)
(Continued)

(52) U.S. Cl.
CPC ....... *G01N 27/623* (2021.01); *G01N 33/0098* (2013.01); *G01N 33/6851* (2013.01);
(Continued)

(58) Field of Classification Search
CPC ............. G01N 27/623; G01N 33/0098; G01N 33/6851; G01N 33/92; G01N 2333/415;
(Continued)

(56) References Cited

U.S. PATENT DOCUMENTS 525,799 A    9/1894   Rymes
3,479,545 A   11/1969   Wilson
(Continued)

FOREIGN PATENT DOCUMENTS

CA        2339552 A1    2/2000
CA        2527886 A1   12/2004
(Continued)

OTHER PUBLICATIONS

Boughton, et al ("Mass spectrometry imaging for plant biology: a review" Phytochemistry Reviews, 15, 445-488 (2016)) (Year: 2016).*
(Continued)

*Primary Examiner* — Michael Maskell
(74) *Attorney, Agent, or Firm* — Goodwin Procter LLP

(57) ABSTRACT

A method of analysis using mass spectrometry and/or ion mobility spectrometry is disclosed comprising: (a) using a first device to generate smoke, aerosol or vapour from a target plant material; (b) mass analysing and/or ion mobility analysing said smoke, aerosol or vapour, or ions derived therefrom, in order to obtain spectrometric data; and (c) analysing said spectrometric data in order to identify and/or characterise said plant material.

19 Claims, 18 Drawing Sheets

(51) Int. Cl.
*G01N 33/00* (2006.01)
*G01N 33/68* (2006.01)
*G01N 33/92* (2006.01)

(52) U.S. Cl.
CPC .......... *G01N 33/92* (2013.01); *H01J 49/0036* (2013.01); *G01N 2333/415* (2013.01); *G01N 2560/00* (2013.01)

(58) Field of Classification Search
CPC ............. G01N 2560/00; G01N 27/622; G01N 33/6848; G01N 30/7233; H01J 49/0036; H01J 49/0459
USPC ......................................... 250/281, 282, 288
See application file for complete search history.

(56) References Cited

U.S. PATENT DOCUMENTS

| | | | |
|---|---|---|---|
| 3,770,954 A | 11/1973 | Davis | |
| 4,408,125 A | 10/1983 | Meuzelaar | |
| H414 H | 1/1988 | Young et al. | |
| 4,835,383 A | 5/1989 | Mahoney et al. | |
| 4,845,367 A | 7/1989 | Amirav et al. | |
| 4,883,958 A | 11/1989 | Vestal | |
| 4,935,624 A | 6/1990 | Henion et al. | |
| 5,033,541 A | 7/1991 | D'Silva | |
| 5,053,343 A | 10/1991 | Vora et al. | |
| 5,210,412 A | 5/1993 | Levis et al. | |
| 5,257,991 A | 11/1993 | Fletcher et al. | |
| 5,306,977 A | 4/1994 | Hayashi | |
| 5,308,977 A | 5/1994 | Oishi et al. | |
| 5,374,755 A | 12/1994 | Neue et al. | |
| 5,454,274 A | 10/1995 | Zhu | |
| 5,509,916 A | 4/1996 | Taylor | |
| 5,559,326 A | 9/1996 | Goodley et al. | |
| 5,663,561 A | 9/1997 | Franzen et al. | |
| 5,696,352 A | 12/1997 | Kourimsky | |
| 5,800,597 A | 9/1998 | Perrotta et al. | |
| 5,828,062 A | 10/1998 | Jarrell et al. | |
| 5,830,214 A | 11/1998 | Flom et al. | |
| 5,836,909 A | 11/1998 | Cosmescu | |
| 5,969,352 A | 10/1999 | French et al. | |
| 5,989,015 A | 11/1999 | Guerin et al. | |
| 6,032,673 A | 3/2000 | Savage et al. | |
| 6,333,632 B1 | 12/2001 | Yang et al. | |
| 6,348,688 B1 | 2/2002 | Vestal | |
| 6,825,464 B2 | 11/2004 | De La Mora | |
| 6,998,622 B1 | 2/2006 | Wang et al. | |
| 7,057,168 B2* | 6/2006 | Miller .................. | G01N 27/622 250/281 |
| 7,238,936 B2 | 7/2007 | Okamura et al. | |
| 7,247,845 B1 | 7/2007 | Gebhardt et al. | |
| 7,329,253 B2 | 2/2008 | Braunstein et al. | |
| 7,335,897 B2 | 2/2008 | Takats et al. | |
| 7,365,309 B2 | 4/2008 | Denny et al. | |
| 7,517,348 B2 | 4/2009 | Vetter et al. | |
| 7,564,028 B2 | 7/2009 | Vestal | |
| 7,718,958 B2 | 5/2010 | Shiea et al. | |
| 7,828,948 B1 | 11/2010 | Hatch et al. | |
| 7,947,039 B2 | 5/2011 | Sartor | |
| 7,960,711 B1 | 6/2011 | Sheehan et al. | |
| 8,156,151 B2 | 4/2012 | Sidman | |
| 8,193,487 B2 | 6/2012 | Briglin et al. | |
| 8,232,520 B2 | 7/2012 | Cristoni | |
| 8,253,098 B2 | 8/2012 | Hiraoka et al. | |
| 8,286,260 B2 | 10/2012 | Vertes et al. | |
| 8,314,382 B2 | 11/2012 | Takats | |
| 8,334,504 B2 | 12/2012 | Finlay et al. | |
| 8,431,409 B1 | 4/2013 | Meinhart et al. | |
| 8,448,493 B2 | 5/2013 | McIntyre et al. | |
| 8,481,922 B2 | 7/2013 | Musselman | |
| 8,778,695 B2 | 7/2014 | Caprioli | |
| 8,803,085 B2 | 8/2014 | Ouyang et al. | |
| 8,834,462 B2 | 9/2014 | Johnson et al. | |
| 8,970,840 B2 | 3/2015 | Kulkarni et al. | |
| 8,980,577 B2 | 3/2015 | Maier et al. | |
| 9,046,448 B2 | 6/2015 | Takats | |
| 9,053,914 B2 | 6/2015 | Pringle et al. | |
| 9,082,603 B2 | 7/2015 | Bajic | |
| 9,120,083 B2 | 9/2015 | Wyndham et al. | |
| 9,255,907 B2 | 2/2016 | Heanue et al. | |
| 9,281,174 B2 | 3/2016 | Takats | |
| 9,287,100 B2 | 3/2016 | Szalay et al. | |
| 9,709,529 B2 | 7/2017 | Takats | |
| 9,731,219 B2 | 8/2017 | Wang et al. | |
| 9,947,524 B2 | 4/2018 | Pringle et al. | |
| 10,077,461 B2 | 9/2018 | Beaulieu et al. | |
| 10,186,626 B2 | 1/2019 | Song et al. | |
| 10,867,779 B2* | 12/2020 | Richardson ......... | H01J 49/0036 |
| 2002/0008871 A1 | 1/2002 | Poustka et al. | |
| 2002/0070338 A1 | 6/2002 | Loboda | |
| 2002/0076824 A1 | 6/2002 | Haglund, Jr. et al. | |
| 2003/0001084 A1 | 1/2003 | Bateman et al. | |
| 2003/0008404 A1 | 1/2003 | Tomita et al. | |
| 2003/0015657 A1 | 1/2003 | Takada et al. | |
| 2003/0042412 A1 | 3/2003 | Park | |
| 2003/0080278 A1 | 5/2003 | Okada et al. | |
| 2003/0119193 A1 | 6/2003 | Hess et al. | |
| 2003/0135222 A1 | 7/2003 | Baska | |
| 2003/0136918 A1 | 7/2003 | Hartley | |
| 2003/0193023 A1 | 10/2003 | Marsh | |
| 2004/0007673 A1 | 1/2004 | Coon et al. | |
| 2004/0079881 A1 | 4/2004 | Fischer et al. | |
| 2004/0124352 A1 | 7/2004 | Kashima et al. | |
| 2004/0197899 A1 | 10/2004 | Gomez et al. | |
| 2004/0217274 A1 | 11/2004 | Bai et al. | |
| 2004/0235395 A1 | 11/2004 | Hashish et al. | |
| 2005/0017091 A1 | 1/2005 | Olsen et al. | |
| 2005/0032471 A1 | 2/2005 | Pfarr et al. | |
| 2005/0061779 A1 | 3/2005 | Blumenfeld et al. | |
| 2005/0067565 A1 | 3/2005 | Takada et al. | |
| 2005/0072916 A1 | 4/2005 | Park | |
| 2005/0074361 A1 | 4/2005 | Tanoshima et al. | |
| 2005/0077644 A1 | 4/2005 | Bryan et al. | |
| 2005/0124986 A1 | 6/2005 | Brounstein et al. | |
| 2005/0138861 A1 | 6/2005 | O'Connor | |
| 2005/0154490 A1 | 7/2005 | Blaine et al. | |
| 2005/0159765 A1 | 7/2005 | Moutafis et al. | |
| 2005/0178962 A1 | 8/2005 | Guevremont et al. | |
| 2005/0178975 A1 | 8/2005 | Glukhoy | |
| 2005/0179366 A1 | 8/2005 | Rose et al. | |
| 2005/0230611 A1 | 10/2005 | Denny et al. | |
| 2005/0230634 A1 | 10/2005 | Bajic et al. | |
| 2005/0230635 A1 | 10/2005 | Takats et al. | |
| 2005/0258358 A1 | 11/2005 | Thakur | |
| 2005/0269518 A1 | 12/2005 | Bajic et al. | |
| 2005/0274885 A1 | 12/2005 | Brown et al. | |
| 2006/0035570 A1 | 2/2006 | Chisum et al. | |
| 2006/0038120 A1 | 2/2006 | Lean et al. | |
| 2006/0054806 A1 | 3/2006 | Yamada et al. | |
| 2006/0091308 A1 | 5/2006 | Boyle et al. | |
| 2006/0097084 A1 | 5/2006 | Gromer et al. | |
| 2006/0108539 A1 | 5/2006 | Franzen | |
| 2006/0113463 A1 | 6/2006 | Rossier et al. | |
| 2006/0122593 A1 | 6/2006 | Jun | |
| 2006/0138321 A1 | 6/2006 | Ahern et al. | |
| 2006/0145089 A1 | 7/2006 | Cristoni et al. | |
| 2006/0186334 A1 | 8/2006 | Jolliffe et al. | |
| 2006/0250138 A1 | 11/2006 | Sparkman et al. | |
| 2006/0255264 A1 | 11/2006 | Belford | |
| 2007/0023631 A1 | 2/2007 | Takats et al. | |
| 2007/0023677 A1 | 2/2007 | Perkins et al. | |
| 2007/0094389 A1 | 4/2007 | Nussey et al. | |
| 2007/0114388 A1 | 5/2007 | Ogawa et al. | |
| 2007/0114394 A1 | 5/2007 | Combs et al. | |
| 2007/0114437 A1 | 5/2007 | Kovtoun | |
| 2007/0176092 A1 | 8/2007 | Miller et al. | |
| 2007/0176113 A1 | 8/2007 | Shiea et al. | |
| 2007/0181802 A1 | 8/2007 | Yamada et al. | |
| 2008/0001081 A1 | 1/2008 | Jindai et al. | |
| 2008/0015278 A1 | 1/2008 | Malik et al. | |
| 2008/0042056 A1 | 2/2008 | Fischer et al. | |
| 2008/0067352 A1 | 3/2008 | Wang | |
| 2008/0073503 A1 | 3/2008 | Wu | |

(56) References Cited

U.S. PATENT DOCUMENTS

| | | |
|---|---|---|
| 2008/0073512 A1 | 3/2008 | Siuzdak et al. |
| 2008/0132890 A1 | 6/2008 | Woloszko et al. |
| 2008/0149822 A1 | 6/2008 | Vertes et al. |
| 2008/0172075 A1 | 7/2008 | Ammann |
| 2008/0173809 A1 | 7/2008 | Wu |
| 2008/0234579 A1 | 9/2008 | Halevy-Politch et al. |
| 2008/0312651 A1 | 12/2008 | Pope et al. |
| 2009/0065714 A1 | 3/2009 | Keady |
| 2009/0082637 A1 | 3/2009 | Galperin |
| 2009/0088772 A1 | 4/2009 | Blumenkranz |
| 2009/0126891 A1 | 5/2009 | Koivunen et al. |
| 2009/0159790 A1 | 6/2009 | Kostiainen et al. |
| 2009/0272893 A1 | 11/2009 | Hieftje et al. |
| 2009/0294660 A1 | 12/2009 | Whitehouse et al. |
| 2009/0302211 A1 | 12/2009 | Takats |
| 2010/0012830 A1 | 1/2010 | Cristoni |
| 2010/0072359 A1 | 3/2010 | Briglin et al. |
| 2010/0078550 A1 | 4/2010 | Wiseman et al. |
| 2010/0101304 A1 | 4/2010 | McIntyre et al. |
| 2010/0176290 A1 | 7/2010 | Vidal-de-Miguel |
| 2010/0186524 A1 | 7/2010 | Ariessohn et al. |
| 2010/0229263 A1 | 9/2010 | Vertes et al. |
| 2010/0273666 A1 | 10/2010 | Bernatchez et al. |
| 2011/0036978 A1 | 2/2011 | Franzen |
| 2011/0049352 A1 | 3/2011 | Ding et al. |
| 2011/0059554 A1 | 3/2011 | Albers et al. |
| 2011/0066147 A1 | 3/2011 | He et al. |
| 2011/0087308 A1 | 4/2011 | Morgan et al. |
| 2011/0121173 A1 | 5/2011 | Koenig et al. |
| 2011/0295250 A1 | 12/2011 | Johnson et al. |
| 2012/0018628 A1 | 1/2012 | Wuijckhuijse et al. |
| 2012/0043460 A1 | 2/2012 | Wouters et al. |
| 2012/0048264 A1 | 3/2012 | Finlay et al. |
| 2012/0074306 A1 | 3/2012 | Jesse et al. |
| 2012/0079894 A1 | 4/2012 | Van Berkel et al. |
| 2012/0080592 A1 | 4/2012 | Wiseman et al. |
| 2012/0085649 A1 | 4/2012 | Sano et al. |
| 2012/0119079 A1 | 5/2012 | Ouyang et al. |
| 2012/0141789 A1 | 6/2012 | Wyndham et al. |
| 2012/0149009 A1 | 6/2012 | Levis et al. |
| 2012/0156712 A1 | 6/2012 | Takats |
| 2012/0190055 A1 | 7/2012 | Cezar et al. |
| 2012/0201846 A1 | 8/2012 | Rehm et al. |
| 2012/0295276 A1 | 11/2012 | Cooks et al. |
| 2012/0308555 A1 | 12/2012 | Polakiewicz et al. |
| 2013/0123919 A1 | 5/2013 | Goldstein et al. |
| 2013/0178845 A1 | 7/2013 | Smith et al. |
| 2013/0181126 A1 | 7/2013 | Jong |
| 2013/0303846 A1 | 11/2013 | Cybulski et al. |
| 2013/0306856 A1 | 11/2013 | Trimpin et al. |
| 2014/0039480 A1 | 2/2014 | Van Wyk |
| 2014/0151547 A1 | 6/2014 | Bajic |
| 2014/0268134 A1 | 9/2014 | O'Connor |
| 2014/0276775 A1 | 9/2014 | Funk et al. |
| 2014/0291506 A1 | 10/2014 | Tikhonski et al. |
| 2014/0297201 A1 | 10/2014 | Knorr et al. |
| 2014/0299577 A1 | 10/2014 | Chung et al. |
| 2014/0303449 A1 | 10/2014 | Balog |
| 2014/0326865 A1 | 11/2014 | Pringle et al. |
| 2014/0336456 A1 | 11/2014 | Demers et al. |
| 2014/0350534 A1 | 11/2014 | Kircher et al. |
| 2014/0353488 A1 | 12/2014 | Takats |
| 2014/0353489 A1 | 12/2014 | Szalay et al. |
| 2015/0021469 A1 | 1/2015 | Bajic |
| 2015/0048255 A1 | 2/2015 | Jarrell |
| 2015/0087003 A1 | 3/2015 | Charles et al. |
| 2015/0144782 A1 | 5/2015 | Fogwill et al. |
| 2015/0192590 A1 | 7/2015 | Sodeoka et al. |
| 2015/0201913 A1 | 7/2015 | Takats |
| 2015/0340215 A1 | 11/2015 | Pringle et al. |
| 2016/0002696 A1 | 1/2016 | Galiano |
| 2016/0133450 A1 | 5/2016 | Green et al. |
| 2016/0215322 A1 | 7/2016 | Goodlett et al. |
| 2016/0247668 A1 | 8/2016 | Szalay et al. |
| 2016/0341712 A1 | 11/2016 | Agar |
| 2016/0372313 A1 | 12/2016 | Brown et al. |
| 2017/0103880 A1 | 4/2017 | Syage |
| 2018/0047551 A1 | 2/2018 | Jones et al. |
| 2018/0053644 A1 | 2/2018 | Jones et al. |
| 2018/0136091 A1 | 5/2018 | Ryan et al. |
| 2018/0254177 A1 | 9/2018 | Gao et al. |
| 2018/0256239 A1 | 9/2018 | Johnson et al. |
| 2020/0144044 A1* | 5/2020 | Zarrine-Afsar ..... H01J 49/0468 |

FOREIGN PATENT DOCUMENTS

| | | |
|---|---|---|
| CA | 2876731 A1 | 12/2013 |
| CA | 2882003 A1 | 2/2014 |
| CN | 1672238 A | 9/2005 |
| CN | 1774627 A | 5/2006 |
| CN | 101073137 A | 11/2007 |
| CN | 101170043 A | 4/2008 |
| CN | 101178381 A | 5/2008 |
| CN | 101223625 A | 7/2008 |
| CN | 101288146 A | 10/2008 |
| CN | 101372502 A | 2/2009 |
| CN | 101413905 A | 4/2009 |
| CN | 101490524 A | 7/2009 |
| CN | 201266145 Y | 7/2009 |
| CN | 101657158 A | 2/2010 |
| CN | 101819179 A | 9/2010 |
| CN | 101871914 A | 10/2010 |
| CN | 102026709 A | 4/2011 |
| CN | 102121921 A | 7/2011 |
| CN | 102137618 A | 7/2011 |
| CN | 102164675 A | 8/2011 |
| CN | 102169791 A | 8/2011 |
| CN | 102264404 A | 11/2011 |
| CN | 102367424 A | 3/2012 |
| CN | 102445544 A | 5/2012 |
| CN | 102483369 A | 5/2012 |
| CN | 102768236 A | 11/2012 |
| CN | 102800553 A | 11/2012 |
| CN | 102879453 A | 1/2013 |
| CN | 102924993 A | 2/2013 |
| CN | 102928610 A | 2/2013 |
| CN | 103295873 A | 9/2013 |
| CN | 103335984 A | 10/2013 |
| CN | 103426712 A | 12/2013 |
| CN | 103456595 A | 12/2013 |
| CN | 103597574 A | 2/2014 |
| CN | 103748233 A | 4/2014 |
| CN | 103764812 A | 4/2014 |
| CN | 104062348 A | 9/2014 |
| CN | 104254772 A | 12/2014 |
| CN | 104254901 A | 12/2014 |
| CN | 104284984 A | 1/2015 |
| CN | 104582616 A | 4/2015 |
| EP | 0169469 A2 | 1/1986 |
| EP | 0437358 A2 | 7/1991 |
| EP | 1225616 A2 | 7/2002 |
| EP | 1530721 A2 | 5/2005 |
| EP | 1650549 A2 | 4/2006 |
| EP | 1855306 A1 | 11/2007 |
| EP | 1730519 B1 | 7/2010 |
| EP | 3265817 A1 | 1/2018 |
| EP | 3266035 A1 | 1/2018 |
| EP | 3265818 B1 | 2/2020 |
| GB | 2420008 B | 5/2006 |
| GB | 2425178 A | 10/2006 |
| GB | 2462190 A | 2/2010 |
| GB | 2491484 A | 12/2012 |
| GB | 2491486 A | 12/2012 |
| GB | 2507298 A | 4/2014 |
| GB | 2523873 A | 9/2015 |
| JP | S63243864 A | 10/1988 |
| JP | 03001435 A | 1/1991 |
| JP | H0785834 A | 3/1995 |
| JP | H07130325 A | 5/1995 |
| JP | H10247472 A | 9/1998 |
| JP | H10302710 A | 11/1998 |
| JP | H1164283 A | 3/1999 |
| JP | 2000097913 A | 4/2000 |
| JP | 2000180413 A | 6/2000 |

(56) References Cited

FOREIGN PATENT DOCUMENTS

| | | |
|---|---|---|
| JP | 2001183345 A | 7/2001 |
| JP | 2002170518 A | 6/2002 |
| JP | 2004264043 A | 9/2004 |
| JP | 2005205181 A | 8/2005 |
| JP | 2006329710 A | 12/2006 |
| JP | 2007051934 A | 3/2007 |
| JP | 2007170870 A | 7/2007 |
| JP | 2007218916 A | 8/2007 |
| JP | 2008249563 A | 10/2008 |
| JP | 2010169454 A | 8/2010 |
| JP | 2014515831 A | 7/2014 |
| JP | 2015503109 A | 1/2015 |
| JP | 2015504160 A | 2/2015 |
| KR | 1020020013544 A | 4/2007 |
| KR | 1020100106336 A | 10/2010 |
| WO | 9734534 A1 | 9/1997 |
| WO | 0160265 A1 | 8/2001 |
| WO | 2008148557 A2 | 12/2008 |
| WO | 2009070555 A1 | 6/2009 |
| WO | 2010075265 A2 | 7/2010 |
| WO | 2010136887 A1 | 12/2010 |
| WO | 2011114902 A1 | 9/2011 |
| WO | 2012143737 A1 | 10/2012 |
| WO | 2012164312 A2 | 12/2012 |
| WO | 2012174437 A1 | 12/2012 |
| WO | 2013093517 A1 | 6/2013 |
| WO | 2013098642 A2 | 7/2013 |
| WO | 2013098645 A2 | 7/2013 |
| WO | 2013102670 A1 | 7/2013 |
| WO | 2013148162 A1 | 10/2013 |
| WO | 2014106165 A | 7/2014 |
| WO | 2014128629 A1 | 8/2014 |
| WO | 2014139018 A1 | 9/2014 |
| WO | 2014140601 A1 | 9/2014 |
| WO | 2014142926 A1 | 9/2014 |
| WO | 2014167828 A1 | 10/2014 |
| WO | 2014202828 A1 | 12/2014 |
| WO | 2015004457 A1 | 1/2015 |
| WO | 2015132579 A1 | 9/2015 |
| WO | 2016046748 A1 | 3/2016 |
| WO | 2016142674 A1 | 9/2016 |
| WO | 2016156615 A1 | 10/2016 |
| WO | 2018142091 A2 | 8/2018 |

OTHER PUBLICATIONS

Arena, et al ("Exploration of Rapid Evaporative-Ionization Mass Spectrometry as a Shotgun Approach for the Comprehensive Characterization of Kigelia Africana (Lam) Benth. Fruit" Molecules 2020, 25(4), 962) (Year: 2020).*
CNOA for Application No. 201680026939.2, dated Apr. 27, 2021, original 10 pp.
CNOA for Application No. 201910350273.1 dated May 8, 2021, 15 pages.
Dixit, et al., "Development of a High Sensitivity Rapid Sandwich ELISA Procedure and its Comparison with the Conventional Approach", Anal Chem 82(16):7049-7052 (2010).
Gholami, A.M., et al., "Global Proteome Analysis of the NCI-60 Cell Line Panel", Cell Reports 4(3):609-620 (2013).
Hanson, et al., "Polymer-coated reversed-phase packings in high-performance liquid chromatography", J Chromat A656:369-380 (1993). Abstract.
Herog, R., et al., "LipidXplorer: A Software for Consensual Cross-Platform Lipidomics" Plos ONE 7(1): e29851.
Hillenkamp, F., et al., "Matrix-Assisted Laser Desorption/Ionization Mass Spectrometry of Biopolymers", Anal Chem 63(24): 1193A-1203A(1991). Abstract.
Hrabak, J., et al., "Matrix-Assisted Laser Desorption Ionizataion-Time of Flight (MALDI-TOF) Mass Spectrometry for Detection of Antibiotic Resistance Mechanisms: from Research to Routine Diagnosis", CMR Journal 26(1): 103-114 (2013).
Kind, T., et al., "LipidBlast—in-silico tandem mass spectrometry database for lipid identification", Nat Methods 10(8):755-758 (2013).
Knochenmuss, R., "Ion Formation Mechanisms in UV-MALDI" Analyst 131:966-986 (2006).
Krishtalik, Lev I., "The mechanism of the proton transfer: an outline", Biochimica et Biophysica Acta (BBA)—Bioenergetics 1458(1):6-27 (2000).
Lipid Maps® [online] [retrieved on Jul. 2, 2021], Retrieved from URL: http://www.lipidmaps.org , 3 pages.
Shamir, E.R., and Ewald, A.J., "Three-dimensional organotypic culture: experimental models of mammalian biology and disease", Nature Rev Mol Cell Biol 15(10):647-664 (2014).
Shoemaker, Robert H., "The NCI60 Human Tumour Cell Line Anticancer Drug Screen", Nature Reviews Cancer 6:813-823 (2006).
Weinstein, "Integromic analysis of the NCI-60 cancer cell lines", Breast Dis 19:11-22 (2004). Abstract.
White, D.C., et al., "Fatty Acid Composition of the Complex Lipids of Staphylococcus aureus During the Formation of Membrane-bound Electron Transport System", Journal of Bacteriology 95:2198-2209 (1968).
Harry, K. H., et al. "Effect of protein coating of flocked swabs on the collection and release of clinically important bacteria", Indian Journal of Medical Microbiology, 32(3):301-303 (2014).
Blais, B. W., "Swab-Based Enzyme Immunoassay System for Detection of Meat Residues on Food Contact Surfaces as a Hygiene Monitoring Tool", Journal of Food Protection, 62(4):386-389 (1999).
Farhat, S. E., et al., "Efficacy of a Swab Transport System in Maintaining Viability of Neisseria gonorrhoeae and *Streptococcus pneumoniae*", Journal of Clinical Microbiology, 39(8):2958-2960 (2001).
Hachmoeller et al., "Element bioimaging of liver needle biopsy specimens from patients with Wilsons disease by laser ablation-inductively coupled plasma-mass spectrometry", Journal of Trace Elements in Medicine and Biology, 35:97-102, Feb. 10, 2016.
Guenther et al., ""Spatially Resolved Metabolic Phenotyping of Breast Cancer by Desorption Electrospray Ionization Mass Spectrometry"", Cancer Research, 75:1828-1837, Feb. 17, 2015.
Extended EP Search Report for EP Patent Application No. 19171058.1, dated Nov. 15, 2019.
Santagata, S., et al., "Intraoperative mass spectrometry mapping of an onco-metabolite to guide brain tumor surgery", Proceedings of the National Academy of Sciences (PNAS), 111(30):11121-11126, Jun. 30, 2014.
Chipuk, J. E., et al., "Transmission Mode Desorption Electrospray Ionization", Journal of the American Society for Mass Spectrometry, 19(11):1612-1620, Nov. 1, 2008.
Harry, E. L. et al., "Direct analysis of pharmaceutical formulations from non-bonded reversed-phase thin-layer chromatography plates by desorption electrospray ionisation ion mobility mass spectrometry", Rapid Communications in Mass Spectrometry, 23(17):2597-2604, Jul. 28, 2009.
Chen, H., et al., "What Can We Learn from Ambient Ionization Techniques", Journal of the American Society for Mass Spectrometry, 20:1947-1963, (2009).
Sankaranarayanan, G., et al., "Common Uses and Cited Complications of Energy in Surgery", Surg Endosc., 27:3056-3072, (2013).
Rau, H.G., et al., "The use of water-jet dissection in open and laparoscopic liver resection", HPB, 10: 275280, (2008).
Office Action for CN Patent Application No. 201680025801.0 dated Apr. 7, 2020.
Office Action for CN Patent Application No. 201680025801.0 dated Apr. 7, 2020 translation.
Adams, F., et al., "Inorganic Mass Spectrometry", copyright John Wiley Sons, Inc. pp. 174-180 (1988).
Vemury, S., and Pratsinis, S.E., "Charging and Coagulation During Flame Synthesis of Silica", Journal of Aerosol Science 27(6):1951-966 (1996).
Examination Report under Section 18(3), for application No. GB1715787.6, dated Jun. 1, 2020, 6 pages.
CNOA for application No. 201680026285.3 dated Jun. 12, 2020, 12 pages.
Panpradist, N., et al., "Swab Sample Transfer for Point-of-Care Diagnostics: Characterization of Swab types and Manual Agitation Methods", Plos One 9(9):1-11 (2014).

(56) References Cited

OTHER PUBLICATIONS

Tait, Emma et al., "Identification of Volatile Organic Compounds Produced by Bacteria Using HS-SPME-GC-MS", Journal of Chromatographic Sci, pp. 1-11.
Uribe, D.O. et al., "Piezoelectric Self-Sensing System for Tactile Intraoperative Brain Tumor Delineation in Neurosurgery", Proceedings of the 31st Annual International Conference of the IEEE Engineering in Medicine and Biology Society: Engineering the Future of BioMedicine, IEEE pp. 737-740 (Sep. 2009).
Kohler, M. et al. "Characterization of lipid extracts from brain tissue and tumors using Raman spectroscopy and mass spectrometry," Anal Bioana Chem, 393:1513-1520, Jan. 20, 2009.
Vander Wilp, W. et al., "Lead in Micro-Samples of Whole Blood by Rhenium-Cup in-Torch Vaporization-Inductively Coupled Plasma-Atomic Emission Spectrometry (ITV-ICP-AES)", Fresenius Journal of Analytical Chemistry, vol. 368, No. 7, pp. 734-736 (Nov. 2000).
Vircks, Kyle E. et al., "Rapid Screening of Synthetic Cathinones as Trace Residues and in Authentic Seizures Using a Portable Mass Spectrometer Equipped with Desorption Electrospray Ionization", Rapid Communications in Mass Spectrometry, vol. 26, No. 23, pp. 2665-2672 (Dec. 15, 2012).
Wehofsky, et al. "Automated deconvolution and deisotoping of electrospray mass spectra" J. Mass Spectrom. 2002; 37: pp. 223-229.
Al Sahaf et al., "Chemical Composition of Smoke Produced by High-Frequency Electrosurgery", Irish Journal of Medical Science, vol. 176, No. 3, pp. 229-232, 2007.
Barrett et al., "Surgical Smoke: A Review of the Literature", Surgical Endoscopy, vol. 17, No. 6, pp. 979-987, 2003.
Down, "A DESI-Rable Ionization Revolutionizes Mass Spectrometry", Base Peak, 2005.
International Search Report and Written Opinion for International Application. No. PCT/IB2012/003009, dated Aug. 14, 2013, 17 pages.
PCT International Search Report and Written Opinion for International Appln. No. PCT/IB2010/001261, dated Sep. 21, 2010, 5 pages.
PCT International Search Report and Written Opinion for International Appln. No. PCT/IB2012/002995, dated Sep. 10, 2013, 3 pages.
Qiao et al., "Electrostatic-Spray Ionization Mass Spectrometry", Analytical Chemistry, vol. 84, No. 17, pp. 7422-7430, 2012.
Lee et al., "Thermally Assisted Electrospray Interface for Liquid Chromatography/Mass Spectrometry", Rapid Communications in Mass Spectrometry, vol. 6, pp. 727-733, 1992.
McEwen et al., "Analysis of Solids, Liquids, and Biological Tissues Using Solids Probe Introduction at Atmospheric Pressure on Commercial LC/MS Instruments", Anal. Chem., vol. 77, pp. 7826-7831, 2005.
Sakairi et al., "Characteristics of a Liquid Chromatograph/Atmospheric Pressure Ionization Mass Spectrometer", Anal. Chem., vol. 60, pp. 774-780, 1988.
Takats et al., "Characterization of DESI-FTICR Mass Spectrometry—From ECD to Accurate Mass Tissue Analysis", Journal of Mass Spectrometry, vol. 43, pp. 196-203, 2008.
Eagles, et al., "Fast Atom Bombardment Mass Spectrometry of Amine Mixtures", John Wiley Sons, Ltd, 1988.
Slemr et al., Concentration Profiles of Diamines in Fresh and aerobically Stored Park and Beef, American Chemical Society, 1985.
Mulligan, Christopher C. et al., "Desorption electrospray ionization with a portable mass spectrometer: in situ analysis of ambient surfaces", Chemical Communications—Chemcom, No. 16, pp. 1709-1711, (Jan. 2006).
Van Berkel, "Thin-Layer Chromatography and El3ectrospray Mass Spectrometry Coupled Using a Surface Sampling probe", Anal. Chem. 2002.
Takats et al., "Mass Spectrometry Sampling Under Ambient Conditions with Desorption Electrospray Ionization", Science, vol. 306, 2004.

Tottszer et al., "Laser Heating Versus Resistive Heating in the Field-Desorption Mass Spectrometry of Organic Polymers", J. Phys. D: Appl. Phys., vol. 21, pp. 1713-1720, 1988.
Zhou, X., et al., "Development of miniature mass spectrometry systems for bioanalysis outside the conventional laboratories " Bioanalysis, 6 (11) 1497-1508 (2014).
Bolt, F., et al., "Automated High-Throughput Identification and Characterization of Clinically Important Bacteria and Fungi using Rapid Evaporative Ionization Mass Spectrometry," American Chemical Socieity, 88 9419-9426 (2016).
McJimpsey, E.L., et al., "Parameters Contributing to Efficient Ion Generation in Aerosol MALDI Mass Spectrometry," American Society for Mass Spectrometry pp. 1044-0305 (2007).
Mutters, N.T., et al., "Performance of Kiestra Total Laboratory Automation Combined with MS in Clinical Microbiology Practice," Annals of Laboratory Medicine 34: 111-117 (2014).
Longuespee, R., et al., Tissue Proteomics for the Next Decade Towards a Molecular Dimension in Histology, OMICS a Journal of Integrative Biology 28(9): 539-552 (2014).
Lu, K., et al., "Arsenic Exposure Perturbs the Gut Microbiome and its Metabolic Profile in Mice: An Integrated Metagenomics and Metabolomics Analysis," Environmental Health Perspectives, 122(3): 284-291 (2014).
Suarez, S., et al., Ribosomal proteins as biomarkers for bacterial identification by mass spectrometry in the clinical microbiology laboratory, Journal of microbiological Methods, 94: 390-396 (2013).
Trimpin, S. et al., New Ionization Method for Analysis on Atmospheric Pressure Ionization Mass Spectrometers Requiring Only Vacuum and Matrix Assistance, Analytical Chemistry, 85:2005-2009 (2013).
Cha, S., Laser desorption/ionization mass spectrometry for direct profiling and imaging of small moledcules from raw biological materials, Doctoral Dissertation, Iowa State University (2008).
Asano et al., "Self-aspirating atmospheric pressure chemical ionization source for direct sampling of analytes on Surfaces in liquid solution", Rapid Communications in Mass Spectrometry 2005.
Examination Report under Section 18(3), for application No. GB1714122.7, dated May 9, 2019, 6 pages.
Bagley, B.M., et al., "Evaluation of archival time on shotgun proteomics of formalin-fixed and paraffin-embedded tissues", Journal of Proteome Research 8(2):917-925, (2009).
Cho, YT., et al. "Differentiation of Virulence of Helicobacter Pyloriby Matrix-Assited Laser Desorption/Ionization Mass Spectrometry and Multivariate Analyses" Clinica Chimica ACTA, Elsevier BV, 424:123-130, May 26, 2013.
Bartels, B. et al., "Spatially resolved in vivo plant metabolomics by laser ablation-based mass spectrometry imaging (MSI) techniques: LDI-MSI and LAESI", Frontiers in Plant Science vol. 6 (2015).
Chen et al. "Desorption Electrospray Ionization Mass spectrometry for high-thoughput analysis of Pharamaceutical samples in the ambient environment" (Year: 2005).
Communication pursuant to Article 94(3) EPC, for application No. 16710788.7, dated Jun. 13, 2019, 9 pages.
Schafer, K.C., et al., "In Situ, Real-Time Identification of Biological Tissue by Ultraviolet and Infrared Laser Desorption Ionization Mass Spectrometry", Analytical Chemistry, 83(5):1632-1640, Mar. 1, 2011.
International Search Report and Written Opinion for International Application No. PCT/GB2016/052956, dated Jan. 26, 2017, 16 pages.
Hsu, et al., "Microscopy ambient ionization top-down mass spectrometry reveals developmental patterning", Proceedings of the National Academy of Sciences, vol. 110, No. 37, pp. 14855-14860, Aug. 22, 2013.
Na, N., et al., "Development of a Dielectric Barrier Discharge Ion Source for Ambient Mass Spectrometry", Journal of The American Society For Mass Spectrometry, Elsevier Science Inc, vol. 18, No. 10, pp. 1859-1862, Sep. 20, 2007.
Jackson, S. N. et al. "On-line laser desorption/ionization mass spectrometry of matrix-coated aerosols", Rapid Communications in Mass Spectrometry, vol. 18, pp. 2041-2045 (Year: 2004).

(56) References Cited

OTHER PUBLICATIONS

Dong, Y., et al., "Sample Preparation for Mass Spectrometry Imaging of Plant Tissues: A Review", Frontiers in Plant Science 7(60): 1-16 (2016).
Partial European Search Report for EP20181905.9, dated Aug. 27, 2020, 14 pages.
Roddy, T., et al., "Imaging of Freeze-Fractured Cells with in Situ Fluorescence and Time-of-Flight Secondary Ion Mass Spectrometry", Analytical Chemistry 74(16):4011-4019(2002).
Petrotchenko, E.V., et al., "Combining Fluorescence Detection and Mass Spectrometric Analysis for Comprehensive and Quantitative Analysis of Redox-Sensitive Cysteines in Native Membrane Proteins", Analytical Chemistry 78(23):7959-7966 (2006).
Ablonczy, Z., et al., "The utilization of fluorescence to identify the components of lipofuscin by imaging mass spectrometry", Proteomics 14(7-8):936-944.
Enthaler, B., et al., "Improved sample preparation for MALDI-MSI of endogenous compounds in skin tissue sections and mapping of exogenous active compounds subsequent to ex-vivo skin penetration" Anal Bioanal Chem 402:1159-1167 (2012).
Extended EP search report for EP Application No. 20172634.6, dated Sep. 14, 2020, 8 pages.
CNOA for application No. CN201680025801.0 dated Oct. 12, 2020 original document and translation.
Adams, F., et al., "Inorganic Mass Spectrometry", (1993) Abstract.
Dong, Y.M.B.A., "Polymer Analysis Handbook", China Petromchemical Press (2004) 8 pages.
Examination Report under Section 18(3) for Application No. GB1713964.3, dated Oct. 26, 2020, 3 pages.
Shin, Y-S., et al., "Desorption Electrospray Ionization-Mass Spectrometry of Proteins" Analytical Chemistry 79:3514-3518 (2007).
Search and Examination Report under Sections 17 and 18(3) for GB1715767.8, dated Nov. 26, 2020, 6 pages.
Waters DESI System Operators Guide 715004701/Revision A, Waters Corporation, [online] Jan. 2015 [retrieved on Dec. 3, 2020]. Retrieved from Internet URL: https://www.waters.com/webassets/cms/support/docs/715004701ra.pdf. 141 pages.
Chen, X., ed., "Liquid Chromatography—Mass Spectrometry—Chapter 8", in Principle and Application of Chromatographic Analysis Technology, Chinese Peoples Public Security University Press, (Jan. 2014) 6 pages.
Song, Y., et al., "Rapid ambient mass spetrometric profiling of intact, untreated bacteria using desoprtion electrospray ionization" ChemComm pp. 61-63 (2007).
Wiseman, J.M. and Li, J.B., "Eluction, Partial Separation, and Identification of Lipids Directly from Tissue Slices on Planar Chromatogrpahy Media by Desoprtion Electrospray Ionization Mass Spectrometry", Anal Chem 82:8866-8874 (2010).
Examination Report under Section 18(3) for Application No. GB2015580.0, dated Jan. 21, 2021, 4 pages.
Krouskop, T., et al., "Elastic moduli of breast and prostate tissues under compression" Ultrasonic Imaging 20:260-274 (1998).
Aberg, P., et al., "Skin Cancer Identification Using Multifrequency Electrical Impedance—A Potential Screening Tool", IEEE Transactions on Biomedical Engineering, 51(12): 2097-2102 (2004).
Forbes, T.P. et al., "Chemical imaging of arlificial Fingerprints by desorption electro-flow focusing ionization mass spectrometry" Analyst 139(12):2982-2985 (2014).
Extended European Search Report for Application No. 20210062.4, dated Mar. 9, 2021, 13 pages.
Rath, C.M., et al., "Molecular Analysis of Model Gut Microbiotas by Imaging Mass Spectrometry and Nanodesorption Electrospray Ionization Reveals Dietary Metabolite Tranformations" Analytical Chemistry 84(21):9259-9267 (2012).
Fenselau, C.C., "Rapid Characterization of Microorganisms by Mass Spectrometry—What Can Be Learned and How" Journal of the American Society for Mass Spectrometry 24(8):1161-1166 (2013).

Uetrecht, C. et al., "Modern Biomolecular Mass Spectrometry and its Role in Studying Virus Structure, Dynamics and Assembly" Angewandte Chemie International Edition 50(36):8248-8262 (2011).
Examination Report for GB Patent Application No. GB2015580.0, dated Mar. 12, 2021.
Cornett, D. S., et al., "A Novel Histology-directed Strategy for MALDI-MS Tissue Profiling That Improves Throughput and Cellular Specificity in Human Breast Cancer", American Society for Biochemistry and Molecular Biology, p. 1975-1983, Jul. 18, 2006.
Examination Report under Section 18(3) for Application No. GB1714165.6, dated Mar. 22, 2021, 6 pages.
Examination Report under Section 18(3) for Application No. GB1715750.4 dated Mar. 22, 2021, 5 pages.
International Search Report and Written Opinion for International Application No. PCT/GB2017/051050 dated Jun. 27, 2017, 15 pages.
Gerbig, S., et al., "Spatially resolved investigation of systemic and contact pesticides in plant material by desorption alectrospray ionization mass spectrometry imaging (DESI-MSI)," Analytical and Bioanalytical Chemistry, 407(24):7379-7389, Jul. 31, 2015.
Lesiak, A. D., et al., Rapid detection by direct analysis in real time-mass spectrometry (DART-MS) of psychoactive plant drugs of abuse: The case of Mitragyna speciosa aka "Krato", Forensic Science International, Elsevier, 242: 210-218, Jul. 14, 2014.
Benjamin, B., et al., "Spatially resolved in vivo plant metabolomics by laser ablation-based mass spectrometry imaging (MSI) techniques: LDI-MSI and LAESI", Frontiers in Plant Science, vol. 6, p. 2-5, Jul. 10, 2015.
Nielen, M. W. F., et al., "Desorption electrospray ionization mass spectrometry in the analysis of chemical food contaminants in food", Trac Trends in Analytical Chemistry, 30(2): 165-180, Feb. 1, 2011.
Boughton, B. A., et al., "Mass spectrometry imaging for plant biology: a review", Phytochemistry Reviews, Kluwer, 15(3): 445-488, Oct. 13, 2015.
Summons to Attend Oral Proceedings Pursuant to Rule 115(1) EPC of EP Application No. 12726643.5, dated Apr. 20, 2018, 7 pages.
Chen et al., "Surface desorption atmospheric pressure chemical ionization mass spectrometry for direct ambient sample analysis without toxic chemical contamination", Journal of Mass Spectrometry, 42(8):1045-1056, Jan. 1, 2007.
Agar, N. et al., "Development of Stereotactic Mass Spectrometry for Brain Tumor Surgery", Biosis, Neurosurgery [online], vol. 68, No. 2, (Feb. 2011) pp. 280-290.
Ahlf, Dorothy R. et al., "Correlated Mass Spectrometry Imaging and Confocal Raman Microscopy for Studies of Three-Dimensional Cell Culture Sections", Analyst, vol. 139, No. 18, p. 4578 (2014).
Azimzadeh, Omid et al., "Formalin-Fixed Paraffin-Embedded (FFPE) Proteome Analysis Using Gel-Free and Gel-Based Proteomics", Journal of Proteome Research, vol. 9, No. 9, pp. 4710-4720 (2010).
Bagley, Brian M. et al., "Evaluation of Archival Time on Shotgun Proteomics of Formalin-Fixed and Paraffin-Embedded Tissues", Journal of Proteome Research, vol. 8 No. 2, pp. 917-925 (2009).
Balog, Julia et al., "Identification of Biological Tissues by Rapid Evaporative Ionization Mass Spectrometry", Analytical Chemistry, vol. 82, No. 17, pp. 7343-7350 (Sep. 2010).
Balog, Julia et al., "Supporting Information for Identification of Biological Tissues by Rapid Evaporative Ionization Mass Spectrometry", pp. SI-S9, http://pubs.acs.org/doi/suppl/10.1021 /ac101, (2013).
Balog, J. et al., "Intraoperative Tissue Identification Using Rapid Evaporative Ionization Mass Spectrometry", Science Translational Medicine, vol. 5, No. 194, pp. 1-11 (Jul. 2013).
Balog, J. et al., "Supplementary Materials: Intraoperative Tissue Identification Using Rapid Evaporative Ionization Mass Spectrometry", Science Translational Medicine, vol. 5, No. 194 34 pages (Jul. 2013).
Bean, Heather D. et al., "Bacterial Volatile Discovery Using Solid Phase Microextraction and Comprehensive Two-Dimensional Gas Chromatographytime-of-Flight Mass Spectrometry", Journal of Chromatography B: Biomedical Sciences Applications, Elsevier, Amersterdam, NL, vol. 901, pp. 41-46 (May 2012).

(56) References Cited

OTHER PUBLICATIONS

Belief, V. et al., "Proteomic Analysis of RCL2 Paraffin-Embedded Tissues", Journal of Cellular and Molecular Medicine, vol. 12, No. 5B, pp. 2027-2036 (2008).
Bocklitz, T.W. et al., "Deeper Understanding of Biological Tissue: Quantitative Correlation of MALDITOF and Raman Imaging", Analytical Chemistry, vol. 85 No. 22, pp. 10829-10834 (2013).
Chen, H., et al: "Neutral desorption sampling coupled to extractive electrospray ionization mass spectrometry for rapid differentiation of biosamples by metabolomic fingerprinting", Journal of Mass Spectromety, vol. 42, No. 9, Sep. 1, 2007 pp. 1123-1135.
Cole, Laura M. et al., "Mass Spectrometry Imaging for the Proteomic Study of Clinical Tissue", Proteomics—Clinical Applications, vol. 9, No. 3-4, pp. 335-341 (Apr. 2015).
Crawshaw, Benjamin et al., "Gastrointestinal Surgery: Real-Time Tissue Identification During Surgery", Nature Review/Gastroenterology Hepatology, vol. 10, No. 11. pp. 624-625.
Cselik, Z. et al., "Impact of Infrared Laser Light-Induced Ablation at Different Wavelengths on Bovine Intervertebral Disc Ex Vivo: Evaluation with Magnetic Resonance Imaging and Histology", Lasers in Surgery and Medicine, vol. 44, No. 5, pp. 406-412 (Jul. 2012).
Davies, T.J. et al., "Volatile Products from Acetylcholine as Markers in the Rapid Urine Test Using Head-Space Gas-Liquid Chromatography",Journal of Chromatography B: Biomedical Sciences and Application, vol. 307, pp. 11-21 (Jan. 1984).
European Commission, "ISD Report Summary", http://cordis.europa.eu/result/rcn/163435_e, (2016).
Fahy, Eoin, et al., "Lipid Classification, Structures and Tools", Biochimica at Biophysica Acta (BBA)—Molecular and Cell Biology of Lipids, vol. 1811, No. 11, pp. 637-647 (2011).
Gerbig, Stefanie et al., "Analysis of Colorectal Adenocarcinoma Tissue by Desorption Electrospray Ionization Mass Spectrometric Imaging", Analytical and Bioanalytical Chemistry, vol. 403, No. 8, pp. 2315-2325 (Mar. 2012).
Golf, Ottmar et al., "Rapid Evaporative Ionization Mass Spectrometry Imaging Platform for Direct Mapping from Bulk Tissue and Bacterial Growth Media", Analytical Chemistry, vol. 87, No. 5, pp. 2527-2534 (Mar. 2015).
Golf, Ottmar et al., "XMS: Cross-Platform Normalization Method for Multimodal Mass Spectrometric Tissue Profiling", Journal of the American Society for Mass Spectrometry, vol. 26, No. 1, pp. 44-54 (Nov. 2014).
Guenther, Sabine et al., "Electrospray Post-Ionization Mass Spectrometry of Electrosurgical Aerosols", Journal of The American Society for Mass Spectrometry, vol. 22, No. 11, pp. 2082-2089 (Nov. 2011).
Gustafsson, Ove J.R. et al., "Proteomic Developments in the Analysis of Formalin-Fixed Tissue", Biochimica et Biophysica Acta, vol. 1854, No. 6, pp. 559-580.
Hensman C., et al: "Chemical Composition of Smoke Produced by High-Frequency Electrosurgery in a Closed Gaseous Environment an in Vitro Study", Surgical Endoscopy, vol. 12, No. 8, Aug. 1, 1998.
Hobbs, S.K. et al.,"Magnetic Resonance Image-Guided Proteomics of Human Glioblastoma Multiforme", Journal of Magnetic Resonance Imaging, vol. 18, pp. 530-536 (Jan. 2003).
Hsu, C. et al., "Visualizing Life with Ambient Mass Spectrometry", Current Opinion in Biotechnology, vol. 31, pp. 24-34 (2015).
Jadoul, L. et al., "Matrix-Assisted Laser Desorption/Ionization Mass Spectrometry and Raman Spectroscopy: An Interesting Complementary Approach for Lipid Detection in Biological Tissues", Eurooean Journal of Lipid Science and Technology. vol. 116, No. 8. pp. 1080-1086 (2014).
Jain, M. et al., "Metabolite Profiling Identifies a Key Role for Glycine in Rapid Cancer Cell Proliferation", American Association for the Advancement of Science, vol. 336, No. 6084, pp. 1040-1044 (May 2012).

Jarmusch, Alan K. et al., "Detection of Strep Throat Causing Bacterium Directly from Medical Swabs by Touch Spray-Mass Spectrometry", Analyst, vol. 139, No. 19, pp. 4785 (Jan. 1, 2014).
Jarmusch, Alan K. et al., "Supplemental Information Detection of Strep Throat Causing Bacterium Directly from Medical Swabs by Touch Spray-Mass Spectrometry", http://www.rsc.org/suppdata/an/c4/c4an00959b/c4an00959b1.
Lazova, Rossitza et al., "Imaging Mass Spectrometry—A New and Promising Method to Differentiate Spitz Nevi From Spitwid Malignant Melanomas", American Journal of Dermatopathology, vol. 34, No. 1, pp. 82-90 (Feb. 2012).
Li, Yan et al., "Aberrant Mucin5B Expression in Lung Adenocarcinomas Detected by iTRAQ Labeling Quantitative Proteomics and Immunohistochemistry", Clinical Proteomics, vol. 10, No. 1, p. 15 (2013).
Lieuwe, D.J. et al., "Volatile Metabolites of Pathogens: A Systematic Review", PLoS Pathogens, vol. 9, Issue 5, e1003311 (May 2013).
Luge, S. et al., "Use of a Lower Power, High Frequency Stabilized Capacitive Plasma Combined with Graphite Furnace Vaporization for the Atomic Emission Spectrometric Analysis of Serum Samples", Analytical Chimica Acta, vol. 332, No. 2-3, pp. 193-199 (Oct. 1996).
Mccullough, Bryan J. et al., "On-Line Reaction Monitoring by Extractive Electrospray Ionisation", Rapid Communications in Mass Spectrometry, vol. 25, No. 10, pp. 1445-1451 (May 2011).
Moot, A. et al: "Composition of Volatile Organic Compouds in Diathermy Plume as Detected by Selected Ion Flow Tube Mass Spectrometry", ANZ Journal of Surgery, vol. 77, No. 1-2, (Jan. 2007) pp. 20-23.
Murray, Patrick R, "What is New in Clinical Microbiology-Microbial Identification by MALDI-TOF Mass Spectrometry", Journal of Molecular Diagnostics, vol. 14, No. 5, pp. 419-423 (Sep. 2012).
Nicholson, Jeremy K. et al., "Metabolic Phenotyping in Clinical and Surgical Environments", Nature, vol. 491, No. 7424 pp. 384-392 (Nov. 2012).
Pirro, Valentina et al., "Direct Drug Analysis from Oral Fluid Using Medical Swab Touch Spray Mass Spectrometry", Analytica Chimica Acta, vol. 861, Jan. 7, 2015 pp. 47-54.
Plata, N. et al., "Aerosols Sampling Using a New Cryogenic Instrument", Journal of Aerosol Science, Pergamon, Amsterdam, NL vol. 37, No. 12, pp. 1871-1875 (Dec. 2006).
Rodriguez-Rigueiro, Teresa et al., "A Novel Procedure for Protein Extraction from Formalin-Fixed Paraffin-Embedded Tissues", Proteomics, vol. 11, No. 12, pp. 2555-2559 (2011).
Schafer, Karl-Christian et al., "In Vivo, In Situ Tissue Analysis Using Rapid Evaporative Ionization Mass Spectrometry", Angewandte Chemie International Edition, vol. 48, No. 44, pp. 8240-8242 (Oct. 2009).
Ellis, S. et al., "Surface Analysis of Lipids by Mass Spectrometry: More Than Just Imaging", Progress in Lipid Research Pergamon Press, vol. 52, No. 4, pp. 329-353 (Oct. 2013).
Shoemaker, Robert H., "The NCI60 Human Tumour Cell Line Anticancer Drug Screen", (2013).
Strittmatter, N. et al., "Anaylsis of Intact Bacteria Using Rapid Evaporative Ionization Mass Spectrometry", Chemical Communications—Chemcon, vol. 49, No. 55, p. 6188 (May 2013).
Strittmatter, N. et al., "Characterization and Identification of Clinically Relevant Microorganisms Using Rapid Evaporative Ionization Mass Spectrometry", Analytical Chemistry, vol. 86, No. 13, pp. 6555-6562 (Jul. 2014).
Strittmatter, N. et al., "Taxon-Specific Markers for the Qualitative and Quantitative Detection of Bacteria in Human Samples", https://www.msacl.org/2015 US Long Abstract.
Strittmatter, N.: "Home—Miss Nicole Strittmatter" Retrieved from the Internet URL: http://www.imperial.ac.uk/people/n.strittmatter12 [retrieved on May 19, 2016] the whole document.
Combined Search and Examination Report under Sections 17 and 18(3), for Application No. GB2110454.2, dated Aug. 19, 2021, 9 pages.
Examination Report under Section 18(3) for Application No. GB1715750.4, dated Oct. 11, 2021, 5 pages.

(56) References Cited

OTHER PUBLICATIONS

Office Action for Chinese application No. 20191104563.7, dated Oct. 11, 2021, original document 14 pages.
Chen Liru, Master student of Nanchang University, Thesis defense date Jun. 7, 2014 "Atmospheric pressure true mass spectrometry technology for rapid identification of lung cancer tissues and experimental study on tissues adjacent to lung cancer—Ambient Mass Spectrometry for Fast Identification of Lung Cancer", original and translated documents.

* cited by examiner

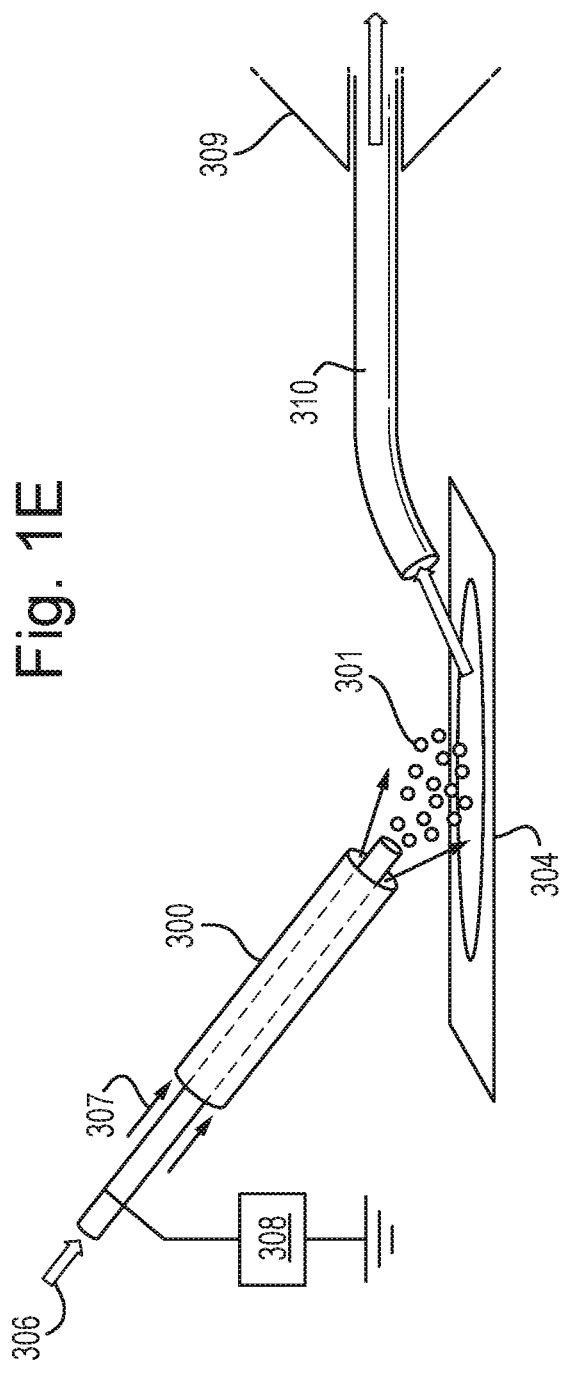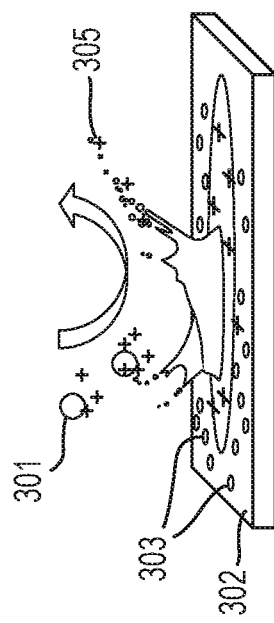

SPECTROMETRIC ANALYSIS OF PLANTS

CROSS-REFERENCE TO RELATED APPLICATIONS

This application is a U.S. national phase filing claiming the benefit of and priority to International Patent Application No. PCT/GB2017/051050, filed on Apr. 13, 2017, which claims priority from and the benefit of United Kingdom patent application No. 1606558.3 filed on Apr. 14, 2016. The entire contents of these applications are incorporated herein by reference.

FIELD OF THE INVENTION

The present invention generally relates to mass spectrometry and/or ion mobility spectrometry, and in particular to methods of analysing plant phenotype and/or genotype such as determining the species and/or herbicide susceptibility of a plant.

BACKGROUND

Environmental factors such as drought, high salinity, freezing temperatures, and/or chemical substances, such as herbicides, are environmental conditions that can cause stress and consequently adverse effects on the growth of plants and the productivity of crops.

The control of weeds, e.g., grass weeds in wheat crop represents a major challenge to sustainable intensification in arable agriculture in Northern Europe. Since the 1980's this problem has been further compounded by the rapid spread of herbicide resistance in weed grass with resultant crop losses estimated at 15-35% due to yield and quality losses. As weed populations differ in their tolerance to herbicides, there is a need for methods to discriminate between them using rapid phenotyping technologies. Farmers require rapid, robust diagnostic technologies in order to deploy alternative weed control strategies in the growing season. Recognising the difference between target site resistant (TSR) and multiple herbicide resistant (MHR) varieties would inform the choice of which, if any, herbicides should be applied or whether alternative control measures should be employed.

It is therefore desired to provide an improved method of analysis for plant material and an improved apparatus therefor.

SUMMARY

The invention provides a method of mass and/or ion mobility spectrometry comprising;

using a first device to generate aerosol, smoke or vapour from one or more regions of a target plant material;

mass analysing and/or ion mobility analysing said aerosol, smoke or vapour or ions derived therefrom; and analysing said spectrometric data in order to analyse said target plant material.

The invention also provides a method of analysis using mass and/or ion mobility spectrometry comprising;

(a) using a first device to generate to generate aerosol, smoke or vapour from one or more regions of a target plant material;

(b) mass analysing and/or ion mobility analysing said aerosol, smoke or vapour or ions derived therefrom in order to obtain spectrometric data; and (c) analysing said spectrometric data in order to analyse said target plant material.

Details of embodiments of the methods are discussed in the detailed description. Thus, unless otherwise stated, any reference to "a method" or "the method" is intended to be a reference to any of the methods provided herein. It is explicitly intended that any of these features may be present in any combination in any of these methods.

BRIEF DESCRIPTION OF THE DRAWINGS

Various embodiments will now be described, by way of example only, and with reference to the accompanying drawings in which:

FIGS. 1E-1F show a DESI method for analyzing target plant material;

DETAILED DESCRIPTION

Figure 1A:
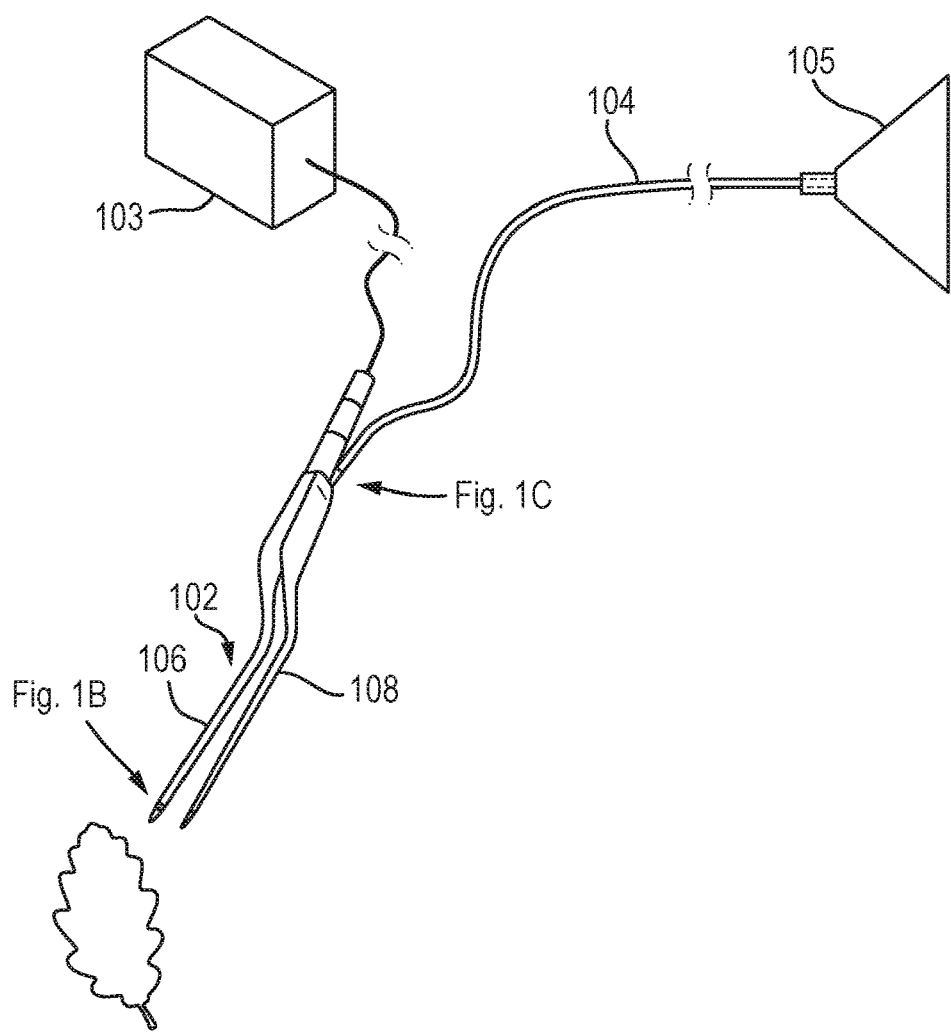
FIGS. 1A-1C show an experimental setup used for REIMS analysis of a plant material which may be used in a method provided herein.

The invention provides a method of analysis using mass spectrometry and/or ion mobility spectrometry comprising:
(a) using a first device to generate smoke, aerosol or vapour from a target plant material;
(b) mass analysing and/or ion mobility analysing said smoke, aerosol or vapour, or ions derived therefrom, in order to obtain spectrometric data; and
(c) analysing said spectrometric data in order to identify and/or characterise said plant material.

The step of analysing may comprise analysing said spectrometric data in order to do one or more of, or any combination of, the following (i) analyse the identity of said plant material; (ii) analyse the genotype and/or phenotype of said plant material; (iii) analyse the effect of an abiotic or biotic stress on said plant material; (iv) analyse the effect of manipulating an abiotic or biotic stress affecting said plant material; (v) analyse the stress state of said plant material; (vi) analyse the effect of manipulating the genotype and/or phenotype of said plant material; (vii) analyse the production of a compound by said plant material; (viii) analyse the utilisation of a substance by said plant material; (ix) analyse the viability of said plant material; (x) analyse the disease state of said plant material; and/or (xi) analyse a compound or biomarker.

It should be understood that any reference herein to "analysing" a target is intended to mean that the target is analysed on the basis of the spectrometric data. Thus, for example, by an expression, such as, "analysing spectrometric data in order to identify a plant type" is meant that the identity of a plant type is determined based upon the spectrometric data. The terms "analysis", "analysing" and derivatives of these terms are used herein to encompass any of the following: identification of a target; characterisation of a target; monitoring the characteristics of a target; detection, identification and/or characterisation of a compound or biomarker in the target; determination and/or monitoring of a status, e.g. a stress and/or disease status; and/or determination of a margin between two different disease or tissue types and the like.

The analysis may be qualitative and/or quantitative. Thus, optionally, any type of analysis may involve determining the concentration, percentage, relative abundance or the like of a compound in the target. Optionally, an increase or decrease in a compound may be analysed.

The identification of a plant material can be important as it can allow a determination to be made as to how to treat the plant material. For example, many weed species differ in their susceptibility to particular herbicides, so identifying a weed can help to decide which herbicide to treat it with. Thus, the method may optionally be a method of identifying and/or authenticating a plant material. Thus, the method may optionally comprise a step of analysing the first spectrometric data in order to identify and/or authenticate the plant material.

The terms "identify", "identification" and derivations of these terms are used interchangeably herein to mean that information about the identity of a target is obtained. This may optionally be the determination of the identity, and/or the confirmation of the identity. This may optionally include information about the precise identity of the target. However, it may alternatively include information that allows the target to be identified as falling into a particular classification.

By "identifying" a plant material is meant that at least some information about the identity of the plant material is obtained, which may, for example, be at any taxonomic level, e.g., at the Phylum, Class, Order, Family, Genus, Species and/or Strain level.

By "identifying" a compound is meant that at least some information about the structure and/or function of the compound is obtained, e.g., the information may optionally allow a compound to be identified as comprising or consisting of a compound selected from any of the types disclosed herein, and/or as being characterised by one or more of the functional groups disclosed herein.

By "identifying" a biomarker is meant that the presence, absence, or relative abundance, of one or more compounds is determined to be a biomarker, e.g., for a particular plant type, genotype, phenotype or the like.

Optionally, the method may be carried out on a plant material wherein (i) the identity of said plant material is known; (ii) the identity of said plant material is unknown; (iii) the plant material has a suspected identity; (iv) the authenticity of the plant material is unconfirmed; or (v) the authenticity of the plant material is confirmed.

Optionally, the plant may be identified as being a particular species or strain in the grass family, e.g., as being a strain of *Alopecurus myosuroides* or *Lollium rigidum*, optionally selected from the Pellium, Oxford, Nottingham and Rothamsted strains of *Alopecurus myosuroides*.

By "characterising" and derivatives of this term is meant that at least some information about one or more characteristics of the plant material is obtained. The characteristic may, e.g., be a characteristic of a plant cell and/or of a plant metabolite. The characteristic may optionally be a genotypic and/or phenotypic trait.

The identification of a plant is an example of a method that provides some information about the genotype and phenotype of a plant. There are other ways in which the genotype and/or phenotype of a plant may be of interest. Thus, in one aspect, the method may be a method of analysing the genotype and/or phenotype of a plant material. Thus, the method may optionally comprise a step of analysing the first spectrometric data in order to analyse the genotype and/or phenotype of the plant material. The identity of the plant material which is analysed in order to analyse its genotype and/or phenotype may be known or unknown.

The term "phenotype" is used to refer to the physical and/or biochemical characteristics of a plant material whereas the term "genotype" is used to refer to the genetic constitution of a plant material.

The term "phenotype" may be used to refer to a collection of a plant material's physical and/or biochemical characteristics, which may optionally be the collection of all of the plant material's physical and/or biochemical characteristics; and/or to refer to one or more of a plant material's physical and/or biochemical characteristics. For example, a plant material may be referred to as having the phenotype of a specific plant type, e.g., a grass plant, and/or as having the phenotype of being target-site herbicide resistant.

The term "genotype" may be used to refer to genetic information, which may include genes, regulatory elements and/or junk DNA. The term "genotype" may be used to refer to a collection of a plant material's genetic information, which may optionally be the collection of all of the plant material's genetic information; and/or to refer to one or more of a plant material's genetic information. For example, a plant material may be referred to as having the genotype of a specific plant type, e.g., a black grass, and/or as having the genotype of encoding a factor involved in herbicide resistance.

It is well known that the genotype of a plant may or may not affect its phenotype, as many genotypic changes may have no phenotypic effect.

The genotype and/or phenotype may optionally be the susceptibility of a plant to abiotic and/or biotic stress, details of which are provided elsewhere herein. The genotype and/or phenotype may optionally be a mutant or transgenic genotype and/or phenotype.

The genotype and/or phenotype of the plant material may optionally be manipulated, e.g., to analyse a cellular process, to analyse and/or alter the susceptibility and/or response to a stress and/or disease, and the like. Optionally, the method may involve the analysis of the effect of such a genotype and/or phenotype manipulation on the plant material, e.g., on the genotype and/or phenotype of the plant material.

The method may optionally be used to analyse a plant material after mutagenesis. Conventional methods for confirming whether or not a plant material has been mutated can be difficult and/or time consuming. Optionally, the method may be used to analyse whether a plant material has been mutated. A mutation may, e.g., be the introduction of a new gene, the silencing of a gene, an alteration in the expression of a gene, or give rise to an altered protein. Silencing may, e.g., be achieved via gene knock-out.

Optionally, the method may be used to analyse the effect of mutagenesis on a plant material, e.g., on the genotype and/or phenotype of a plant material.

Optionally, the method may be used to analyse a plant material at 2 or more time points, e.g., before and after mutagenesis, and/or at 2 or more time points after mutagenesis.

The method may optionally be a method of analysing the effect of an abiotic and/or biotic stress on a plant material. Thus, the method may optionally comprise a step of analysing the first spectrometric data in order to analyse the effect of an abiotic and/or biotic stress on the plant material. For example, a plant material may be analysed before and after being exposed to an abiotic and/or biotic stress to analyse whether the stress had any effect on the plant material. Alternatively or in addition, a first plant material that has been exposed to a first abiotic and/or biotic stress and a second plant material that has not been exposed to a first abiotic and/or biotic stress, but has optionally been exposed to a second abiotic and/or biotic stress, may be analysed and compared to determine if there are any differences between the first and the second plant materials.

The method may be carried out on a plant material known to have been exposed to one or more stress factors; suspected of having been exposed to one or more stress factors; suspected of not having been exposed to one or more stress factors; or known not to have been exposed to one or more stress factors. Thus, the stress status of the plant material may be known or unknown. The method may optionally be a method of analysing the stress status of a plant material. Thus, the method may optionally comprise a step of analysing the first spectrometric data in order to analyse the stress status of the plant material.

The growth conditions of a plant material, e.g., the exposure of a plant material to a stress may optionally be manipulated, e.g., by adding, increasing, decreasing or removing one or more stress factors, details of which are provided elsewhere herein. The method may optionally be a method of analysing the effect of manipulating the stress affecting a plant material. Thus, the method may optionally comprise a step of analysing the first spectrometric data in order to analyse the effect of manipulating the stress affecting the plant material.

Plants may produce various metabolites, such as secondary metabolites, which may be involved in a stress response, e.g., may mediate the resistance to one or more stress factors. Unless otherwise stated, the terms "metabolite" and "compound" are used interchangeably herein. The method may optionally be a method of analysing the production of a compound by a plant material. Thus, the method may optionally comprise a step of analysing the first spectrometric data in order to analyse the production of a compound by the plant material.

Plants may differ in their utilisation of substances such as nutrients, minerals and the like. Plant material analysis may shows the nutrient status of the plant material at the time of sampling. This, in turn, may show whether nutrient supplies are adequate. Plant material analysis may detect unseen deficiencies and/or may confirm visual symptoms of deficiencies. Toxins, e.g., heavy metals, pesticides etc., may accumulate in a plant material and their presence, absence and/or levels may be analysed. Sampling a crop periodically may provide a record of its nutrient content that can be used through the growing season or from year to year, allowing the tailoring of, e.g., fertilization, weed and/or pest control practices to the plant's needs.

The method may optionally be a method of analysing the utilisation of a substance by a plant material. Thus, the method may optionally comprise a step of analysing the first spectrometric data in order to analyse the utilisation of a substance by the plant material.

The method may optionally be a method of analysing a compound in or on a plant material. Thus, the method may optionally comprise a step of analysing the first spectrometric data in order to analyse a compound in or on the plant material.

The natural environment for plants is composed of a complex set stresses. As mentioned elsewhere herein, the methods provided herein may be used, e.g., to analyse the susceptibility of a plant material to a stress; the response of a plant material to a stress; the effect of a stress on a plant material; and/or the effect of altering a stress to which a plant material is exposed to.

The term "stress" is used to refer to abiotic and/or biotic stress. By "abiotic stress" is meant a non-living factor that may have a negative effect on a plant, particularly on a susceptible plant. By "biotic stress" is meant a living factor that may have a negative effect on a plant, particularly on a susceptible plant.

Any of the factors that may cause stress may be referred to as "stress factors". An abiotic stress factor may optionally be the presence, absence, or non-optimal level, of water, temperature, radiation, a nutrient, a mineral, pH, growth inhibitors and/or toxins.

More particularly, it may optionally be a growth inhibitor selected from a herbicide and a pesticide, such as a fungicide and/or insecticide; water deficit, drought, or flooding; cold, frost, freezing, or heat; high, low, or no radiation; acidic, neutral, or basic pH; salinity; mineral deficiency or toxicity; nutrient deficiency or toxicity; high or low humidity; air and/or ground pollution; and/or deficiency or toxicity of a gas and/or chemical substance.

A biotic stress factor may optionally be a microbe, e.g., a virus, bacterium, fungus, or protozoa; an insect; or an animal such as a rodent. The virus may optionally be a tomato spotted wilt virus (TSVVV); a Cucumber Mosaic virus (CMV), e.g., a CMV which contains fragments of peanut stunt virus (PSV), or a CMV RS isolate; Tobacco mosaic virus; Tomato yellow leaf curl virus; Potato virus Y; Cauliflower mosaic virus; African cassava mosaic virus; Plum pox virus; Brome mosaic virus; Potato virus X; Citrus tristeza virus; Barley yellow dwarf virus; Potato leafroll virus; or Tomato bushy stunt virus.

The fungus may optionally be from the Rhytismataceae family, e.g., *Rhytisma acerinum*; Magnaporthe oryzae; Botrytis cinerea; Puccinia spp.; Fusarium graminearum; Fusarium oxysporum; Blumeria graminis; Mycosphaerella graminicola; Colletotrichum spp.; Ustilago maydis; Melampsora lini; Phakopsora pachyrhizi; or Rhizoctonia solani.

The stress factor may, e.g., be in the growth medium, such as in the soil, and/or the atmosphere.

The herbicide may optionally be a Acetyl coenzyme A carboxylase (ACCase) inhibitor; a acetolactate synthase (ALS) inhibitor; a enolpyruvylshikimate 3-phosphate synthase enzyme (EPSPS) inhibitor; a synthetic auxin; a photosystem I inhibitor; a photosystem II inhibitor; and/or a 4-Hydroxyphenylpyruvate dioxygenase (HPPD) inhibitor.

The method may be carried out on a "target" plant material. The term "plant material" is used herein to encompass whole plants as well as parts of a plant and specimens derived from a plant and the terms "plant" and "plant material" are, unless otherwise stated, used interchangeably herein. Optionally, the plant material may be a whole plant. Optionally, it may be a specimen derived therefrom.

The "plant" may optionally be a green plant, which may, e.g., be selected from land plants and green algae. Optionally, it may be a vascular or non-vascular plant; a seed plant or a non-seed plant; and/or a flowering or non-flowering plant. Optionally, it may be selected from club mosses, horsetails, ferns, gymnosperms and angiosperms (flowering plants). Optionally, it may be a monocot plant, optionally a plant from the grass family (the Poaceae), e.g., wheat, rice, corn, rye, barley, oat, sorghum, wild rice, and/or millet. Optionally, it may be a paprika plant, e.g. species Galga, *Capsicum annum*; a tobacco plant, e.g., a Nicotania plant, e.g., *Nicotiana benthamiana* Domin, or *Nicotiana tabacum* L. cv. Xanthi nc; a bean plant, e.g., a *Phaseolus* plant, e.g. *Phaseolus vulgaris* L. Minidor; or a member of the acer species, e.g., Sycamore tree.

Optionally, it may be selected from *Alopecurus* and/or *Lollium*, e.g., *Alopecurus myosuroides* and/or *Lollium rigidum*, optionally from the strains listed in Table 1.1.

Thus, any agriculture, agronomy and/or horticulture applications of the method are contemplated.

The method may optionally be carried out on an in vivo target, i.e. on a living plant material. For example, it may be carried out by using a thermal ablation method. Alternatively or in addition, it may optionally be carried out on a dead plant material. Alternatively or in addition, it may optionally be carried out on an ex vivo or in vitro target, e.g., on a specimen. The plant material may optionally be a mature plant or a seedling.

The target plant material may optionally comprise or consist of one or more stems, leaves, roots, flowers, seeds, plant fluid, a part of any thereof, and/or a combination of any thereof. For example, it may comprise or consist of one or more of a leaf blade, a petiole, a whole compound leaf, a terminal leaflet, a most recent mature leaf (MRML), and/or a combination of any thereof. It may optionally comprise or consist of vascular tissue, epidermal tissue, ground tissue and/or meristematic tissue, e.g., xylem, phloem, parenchyma, collenchyma, and/or sclerenchyma.

The most recent mature leaf (MRML) is the first fully expanded leaf below the growing point. For some crops, the most recent mature leaf is a compound leaf. The most recent mature leaf on soybean and strawberry, for example, is a trifoliate compound leaf comprising three leaflets.

A plant fluid may, for example, optionally be selected from xylem sap, phloem sap, resin and/or cell sap.

Optionally, the specimen may be dried, collected with a swab, and/or dispensed onto an absorbent carrier, e.g. a filter or paper.

Optionally, the specimen may be sectioned and/or sequentially disassociated, e.g., mechanically and/or enzymatically, for example with trypsin, to obtain different layers of the specimen, and/or to derive cells from different layers of a specimen. Different layers, or cells derived from different layers, of the specimen may then be analysed. During plant growth and/or maintenance, different layers of the plant may have been exposed to different environmental conditions, and/or been exposed to different concentrations of a substance, as substances may not penetrate each layer at the same rate. Thus, the method may optionally be used to analyse one or more different layers of a specimen, or cells derived therefrom.

The method may optionally involve the analysis of one or more different targets. Optionally, 2 or more targets at or from different locations within a plant material may be analysed. Optionally, a target may be at or from one or more locations known or suspected to be healthy and/or unstressed; and one or more locations known or suspected to be diseased and/or stressed.

Optionally, 2 or more distinct plant materials may be analysed, which may optionally be 2 or more plant materials thereof known or suspected to be genotypically and/or phenotypically different from one another, or which may be known or suspected to share one or more genotypic and/or phenotypic traits, or to be genotypically and/or phenotypically identical. Optionally, the 2 or more distinct plant materials may be at or from different geographical locations, e.g., from different locations within a crop growing area.

Optionally, distinct locations of a target may be analysed, e.g., a series of points may be sampled, optionally with or without spatial encoding information for imaging purposes.

The method may optionally be carried out on a target that is native. By "native" is meant that the target has not been modified prior to performing the method of the invention. In particular, the target may be native in that the tissue or cells present in the target plant material are not subjected to a step of lysis or extraction, e.g., lipid extraction, prior to performance of the method provided herein. Thus, a target plant material may be native in that it comprises or consists essentially of intact tissue and/or cells Thus, by native is meant that the target has not been chemically or physically modified and is thus chemically and physically native. Optionally, the target may be chemically native, i.e. it may be chemically unmodified, meaning that it has not been contacted with a chemical agent so as to change its chemistry. Contacting a target with a matrix is an example of a chemical modification.

Optionally, the target may be physically native, i.e. it may be physically unmodified, meaning that it has not been modified physically. Freezing, thawing, and/or sectioning are examples of physical modifications. The skilled person will appreciate that although physical actions, such as, freezing, may affect a specimen's chemistry, for the purpose of this invention such an action is not considered to be a chemical modification.

Thus, optionally the target may be chemically native, but not physically native, e.g. because it has been frozen, dried and/or sectioned.

Optionally, the target may be frozen, previously frozen and then thawed, fixed, sectioned, dried and/or otherwise prepared. Optionally, the method may be carried out on a target that has not undergone a step of preparation specifically for the purpose of mass and/or ion mobility spectrometry analysis.

The target may not have been contacted with a solvent, or a solvent other than water, prior to generating the smoke, aerosol or vapour from the target.

Additionally, or alternatively, the target may not be contacted with a matrix prior to generating the smoke, aerosol or vapour from the target. For example, the target may not be contacted with a MALDI matrix or other matrix for assisting ionisation of material in the target. A MALDI matrix may, e.g., comprise or consist of small organic acids such as a-cyano-4-hydroxycinnamic acid (CHCA) and/or 2,5-dihydroxybenzoic acid (DHB).

The method may optionally be carried out on a target that has been prepared for a particular mass and/or ion mobility spectrometry analysis; and/or that has been prepared for any other analytical method.

Any of the methods may optionally include automatic sampling, which may optionally be carried out using a REIMS device. Any of the methods may optionally comprise using a disposable sampling tip.

The method may optionally involve the analysis of one or more biomarkers. A biomarker may be an objective, quantifiable characteristic of, e.g., a phenotype and/or genotype.

The term "biomarker" is sometimes used explicitly herein, but it should also be understood that any of the analyses mentioned herein may optionally be the analysis of a biomarker. The biomarker may optionally be a spectrometric biomarker. The term "spectral biomarker" or "spectrometric biomarker" is used herein to refer to spectrometric data that is characteristic of a plant type, e.g., a plant genotype and/or phenotype, characteristic of a plant biological process, and/or characteristic of a compound, such as a plant metabolite, but for simplicity, a spectrometric biomarker may simply be referred to as a "biomarker".

By "characteristic of a plant type" is meant that the biomarker may optionally be used to analyse, e.g., identify and/or characterise said plant type. Optionally, the biomarker may be used to distinguish between taxonomically different plants and/or between genotypically and/or phenotypically different plants, e.g., between a wild-type and a mutant plant; a stressed and an unstressed plant, and/or between a diseased and a healthy plant.

A biomarker may optionally be used to analyse the stress and/or disease status of a target plant material. Optionally, the biomarker may be used to distinguish between healthy and stressed and/or diseased plants; and/or to analyse the severity of a stress and/or disease.

As discussed elsewhere herein, identification may be on any level, for example, on a taxonomic level. A biomarker that allows identification of a plant as belonging to a particular taxonomic level may be referred to as a "taxonomic marker" or "taxonomic biomarker". Thus, a taxonomic marker may be specific for a Kingdom, Phylum, Class, Order, Family, Genus, Species and/or Strain.

By "characteristic of a compound" is meant that the biomarker may optionally be used to analyse, e.g., detect, identify and/or characterise said compound.

By "characteristic of a plant biological process" is meant that the biomarker may optionally be used to analyse a biological process carried out by a plant material. Optionally, the biomarker may be used to analyse the start, progression, speed, efficiency, specificity and/or end of a plant biological process.

Different plant types, stress and/or disease states, metabolites, plant biological progresses and the like may be characterised by the presence or absence, and/or relative abundance, of one or more compounds, which may serve as biomarkers. Any reference herein to a biomarker being a particular compound, or class of compounds, should be understood optionally to be the spectrometric data of that compound, or class of compounds.

For example, a reference to a "Phellodensin E" biomarker should be understood to be a reference to the spectrometric data corresponding to Phellodensin E which may, e.g., be a signal corresponding to m/z of about 517, e.g., 517.1728; whereas a reference to a "Secologanin" biomarker should be understood to be a reference to the spectrometric data corresponding to Secologanin (C17H24O10), which may, e.g., be a signal corresponding to m/z of about 387, e.g., 387.1298.

As explained above, a biomarker may be indicative of a plant type, stress and/or disease status, metabolite, and/or plant biological process. A biomarker which is indicative of herbicide resistance may therefore be referred to as a "herbicide resistance biomarker"; a biomarker which is indicative of *Lollium rigidum* may be referred to as a "*Lollium rigidum* biomarker" and so on.

Optionally, a spectrometric biomarker may be identified as being the spectrometric data of a particular compound, or class of compounds. Thus, a signal corresponding to a particular mass, charge state, m/z and/or ion mobility (e.g., due to cross-sectional shape or area) may optionally be identified as being indicative of the presence of a particular compound, or class of compounds.

Optionally, spectrometric signal may serve as a biomarker even if a determination has not been made as to which particular compound, or class of compounds gave rise to that signal. Optionally, a pattern of spectrometric signals may serve as a biomarker even if a determination has not been made as to which particular compounds, or class of compounds, gave rise to one or more signals in that pattern, or any of the signals in a pattern.

The work disclosed herein has led to the identification of a range of biomarkers, as well as allowing the identification of further biomarkers. Optionally, the biomarker may be selected from any of the biomarkers disclosed herein, including in any of the Examples and/or the Tables. Optionally, the biomarker may be a biomarker of the substituted or unsubstituted form of any of the biomarkers mentioned herein; and or of an ether, ester, phosphorylated and/or glycosylated form, or other derivative, of any of the biomarkers mentioned herein.

Optionally, the biomarker may be a biomarker of a lipid; a protein; a carbohydrate; a DNA molecule; an RNA molecule; a polypeptide, such as, a ribosomal peptide or a non-ribosomal peptide; an oligopeptide; a lipoprotein; a lipopeptide; an amino acid; and/or a chemical compound, optionally an organic chemical molecule or an inorganic chemical molecule.

A biomarker may optionally be the clear-cut presence or absence of a particular compound, which may optionally manifest itself as the presence or absence of a spectrometric signal corresponding to a specific mass, charge state, m/z and/or ion mobility.

A biomarker may optionally be the relative abundance of a particular compound, which may optionally manifest itself as the relative intensity of a spectrometric signal corresponding to a specific mass, charge state, m/z and/or ion mobility.

A biomarker may optionally be the relative abundance of more or more compounds, which may optionally manifest itself as the relative intensity of two or more spectrometric signals corresponding to two or more specific mass, charge state, m/z and/or ion mobility.

Thus, a biomarker may optionally be an increased or decreased level of one or more compounds, e.g., a metabolite, a lipopeptide and/or lipid species, which may optionally manifest itself as an increase and/or decrease in the intensity of two or more spectrometric signals corresponding to two or more specific mass, charge state, m/z and/or ion mobility.

The presence, absence and relative abundance of a variety of compounds may be referred to as a molecular "fingerprint" or "profile". The totality of the lipids of a cell may be referred to as a lipidomic fingerprint/profile, whereas the totality of metabolites produced by a cell may be referred to as a metabolomic fingerprint/profile.

Thus, the biomarker may be a molecular fingerprint, e.g., a lipid fingerprint and/or a metabolomic fingerprint, more particularly e.g., a (i) a lipidomic profile; (ii) a fatty acid profile; (iii) a phospholipid profile; (iv) a phosphatidic acid (PA) profile; (v) a phosphatidylethanolamine (PE) profile; (vi) a phosphatidylglycerol (PG) profile; (vii) a phosphatidylserines (PS) profile; and/or (viii) a phosphatidylinositol (PI) profile.

By way of example, certain glycerophospholipids are less abundant in multiple herbicide resistant black grass than in wild-type black grass, so the relative abundance of such glycerophospholipids may be a biomarker for herbicide susceptibility.

The biomarker may optionally be a direct biomarker or an indirect biomarker. By "direct" biomarker is meant that the spectrometric data is produced directly from the biomarker. For example, if a particular compound has a specific spectrometric signal or signal pattern, then obtaining this signal or signal pattern from a sample provides direct information about the presence of that compound. This may be the case, for example, for a metabolite produced in significant amounts by a plant. Optionally, in such an example, the spectrometric data from the compound may alternatively or in addition serve as an indirect biomarker for the plant type that produced this compound.

By "indirect" biomarker is meant that the spectrometric data is produced from one or more biomarkers that is/are indicative of a particular compound, plant biological process, and/or type of plant. Thus, an indirect biomarker is spectrometric data generated from one or more molecules that provides information about a different molecule. For example, a molecular fingerprint, such as, a lipid fingerprint, may be indicative of the expression of a particular protein, e.g. a receptor; or of a particular plant type.

A lipid biomarker may optionally be selected from, e.g., fatty acids, glycerolipids, sterol lipids, sphingolipids, prenol lipids, saccharolipids and/or phospholipids. A brief overview of various lipids is provided below, but it must be appreciated that any particular lipid may fall into more than one of the groups mentioned herein.

A fatty acid is an aliphatic monocarboxylic acid. The fatty acid may optionally have a carbon chain comprising precisely or at least 4, 6, 8, 10, 12, 14, 16, 18, 20, 22, 24, 26, 28, 30, 32, 36, 38 or 40 carbons. It may optionally be monounsaturated, polyunsaturated, or saturated. It may optionally be an eicosanoid. It may, for example, be oleic acid, palmitic acid, arachidonic acid, linoleic acid, capric acid, caprylic acid, and/or lauric acid.

The glycerolipid may optionally be selected from e.g., monoacylglycerol, diacylglycerol, and/or triacylglycerol.

The sterol may optionally be selected from free sterols, acylated sterols (sterol esters), alkylated sterols (steryl alkyl ethers), sulfated sterols (sterol sulfate), sterols linked to a glycoside moiety (steryl glycosides) and/or acylated sterols linked to a glycoside moiety (acylated sterol glycosides).

The sterol may optionally have an aliphatic side chain of precisely or at least 8, 9, 10, 11, 12, 13, 14, 15, 16, 17, 18, 19, 10, 21, 22, 23, 24, 25, 26, 27, 28, 29, 20, 35 or 40 carbon atoms. The number of carbon atoms in the aliphatic side chain may be expressed by the letter C followed by the number, e.g., C27 for cholesterol. It may, for example, be selected from cholesterol, cholesterol sulphate, ergosterol, lanosterol, dinosterol (4a,23,24-trimethyl-5a-cholest-22E-en-3b-ol), oxysterol and/or a derivative of any thereof.

A phospholipid may comprise two fatty acids, a glycerol unit, a phosphate group and a polar molecule. The Phospholipid may optionally comprise an ester, ether and/or other 0-derivative of glycerol. The phospholipid may optionally be selected from, e.g., Phosphatidylglycerol, diphosphatidylglycerol (cardiolipin), and/or Acylphosphatidylglycerol (1,2-diacyl-sn-glycero-3-phospho-(3'-acyl)-1'-sn-glycerol).

The phosphatidylglycerol lipid may optionally be selected from phosphatidic acids (PAs), phosphatidylethanolamines (PEs), phosphatidylglycerols (PGs), phosphatidylcholines (PCs), phosphatidylinositols (PIs) and/or phosphatidylserines (PSs).

A sphingolipid is a lipid containing a sphingoid. It may optionally be selected from, e.g., a ceramide, i.e. an N-acylated sphingoid; sphingomyelin, i.e. a ceramide-1-phosphocholine; phosphoethanolamine dihidroceramide, and/or a glycosphingolipid, i.e. a lipid containing a sphingoid and one or more sugars. For example, it may optionally be a glycosylated ceramide.

The biomarker may optionally be a metabolite, such as, a primary or a secondary metabolite; an antibiotic; a fatty acid synthase product; a pheromone; and/or a biopolymer.

A biomarker compound may optionally be characterised by one or more of the following functional groups: alcohol, ester, alkane, alkene, alkyne, ether, ketone, aldehyde, anhydride, amine, amide, nitrile, aromatic, carboxylic acid, alkyl halide, and/or carbonyl. Optionally, it may additionally be identified as being primary, secondary or tertiary, e.g., a primary alcohol, a secondary amine, or the like.

The method of the invention may optionally involve the analysis of an exogenous compound, i.e. a compound that was brought into contact with a plant material. Thus, the biomarker may be an exogenous compound.

The method may optionally involve the analysis of one or more compounds. Unless otherwise stated, the terms "compound", "substance", "molecule" and "metabolite" etc. are used interchangeably herein.

The compound may optionally be intracellular and/or extracellular. It may optionally be endogenous, i.e. produced by the plant material, and/or exogenous, i.e. added to the plant material.

The compound may optionally comprise or consist of any of the compounds or classes of compounds mentioned herein, e.g. any of the biomarker compounds mentioned herein. Optionally, it may comprise or consist of, for example, a lipid, such as, a glycolipid or phospholipid; carbohydrate; DNA; RNA; protein; polypeptide, such as, a ribosomal peptide or a non-ribosomal peptide; oligopeptide; lipoprotein; lipopeptide; amino acid; and/or chemical molecule, optionally an organic chemical molecule.

The compound may optionally be linear, cyclic or branched.

The compound may optionally be a metabolite, such as, a primary or a secondary metabolite; an antibiotic; a fatty acid synthase product; a pheromone; and/or a biopolymer.

The compound may optionally be characterised by one or more of the following functional groups: alcohol, ester, alkane, alkene, alkyne, ether, ketone, aldehyde, anhydride, amine, amide, nitrile, aromatic, carboxylic acid, alkyl halide, and/or carbonyl. Optionally, it may additionally be identified as being primary, secondary or tertiary, e.g., a primary alcohol, a secondary amine, or the like.

Optionally, the method may involve the analysis of the cellular composition of a plant or specimen thereof. For example, the proportion of one or more particular cell types may be analysed. The cell types may optionally be selected from any known cell types, e.g., any of the cell types mentioned herein. For example, the presence, location, spatial distribution, concentration and/or type of one or more cells and/or compounds may be analysed.

The embodiments of the invention described herein may, for example, be used in or with a real-time, robust tissue characterisation tool which utilises ambient ionisation technologies, such as REIMS technology.

Various embodiments will now be described in more detail below which in general relate to generating an aerosol, surgical smoke or vapour from one or more regions of a target (details of which are provided elsewhere herein) using an ambient ionisation ion source. The aerosol, surgical smoke or vapour may then be mixed with a matrix and aspirated into a vacuum chamber of a mass and/or ion mobility spectrometer. The mixture may be caused to impact upon a collision surface causing the aerosol, smoke or vapour to be ionised by impact ionisation which results in the generation of analyte ions. The resulting analyte ions (or fragment or product ions derived from the analyte ions) may then be mass and/or ion mobility analysed and the resulting mass and/or ion mobility spectrometric data may be subjected to multivariate analysis or other mathematical treatment in order to determine one or more properties of the target in real time. For example, the multivariate analysis may enable a determination to be made of a plant's genotype and/or phenotype. In particular, a determination may be made as to the susceptibility of a plant to one or more herbicides.

In any of the methods provided herein a device may be used to generate an aerosol, smoke or vapour from one or more regions of a plant material target (details of which are provided elsewhere herein). The device may comprise an ambient ionisation ion source which is characterised by the ability to generate analyte aerosol, smoke or vapour from a plant material target (details of which are provided elsewhere herein), which may, e.g., be a native or unmodified target. By contrast, other types of ionisation ion sources such as Matrix Assisted Laser Desorption Ionisation ("MALDI") ion sources require a matrix or reagent to be added to the sample prior to ionisation.

It will be apparent that the requirement to add a matrix or a reagent directly to a sample may prevent the ability to perform in vivo analysis of plant material and also, more generally, prevents the ability to provide a rapid simple analysis of target plant material.

Ambient ionisation techniques are particularly useful since firstly they do not require the addition of a matrix or a reagent to the sample (and hence are suitable for the analysis of in vivo material) and since secondly they enable a rapid simple analysis of target plant material to be performed. Whilst there is no requirement to add a matrix or reagent to a sample in order to perform ambient ionization techniques, the method may optionally include a step of adding a matrix or reagent to the plant material target (e.g., directly to the target) prior to analysis. The matrix or reagent may be added to the plant material target, e.g., to lyse the cells of the plant material target or to enhance the signal therefrom during the analysis.

A number of different ambient ionisation techniques are known and are intended to fall within the scope of the present invention. As a matter of historical record, Desorption Electrospray Ionisation ("DESI") was the first ambient ionisation technique to be developed and was disclosed in 2004. Since 2004, a number of other ambient ionisation techniques have been developed. These ambient ionisation techniques differ in their precise ionisation method but they share the same general capability of generating gas-phase ions directly from (e.g., native, untreated or unmodified) samples. The various ambient ionisation techniques which are intended to fall within the scope of the present invention may not require any prior sample preparation. As a result, the various ambient ionisation techniques enable both in vivo plant material and ex vivo plant material samples to be analysed without the time, expense and problems associated with adding a matrix or reagent to the plant material sample or other plant material target material.

A list of ambient ionisation techniques which are intended to fall within the scope of the methods provided herein are given in the following table:

| Acronym | Ionisation technique |
| --- | --- |
| DESI | Desorption electrospray ionization |
| DeSSI | Desorption sonic spray ionization |
| DAPPI | Desorption atmospheric pressure photoionization |

-continued

| Acronym | Ionisation technique |
|---|---|
| EASI | Easy ambient sonic-spray ionization |
| JeDI | Jet desorption electrospray ionization |
| TM-DESI | Transmission mode desorption electrospray ionization |
| LMJ-SSP | Liquid microjunction-surface sampling probe |
| DICE | Desorption ionization by charge exchange |
| Nano-DESI | Nanospray desorption electrospray ionization |
| EADESI | Electrode-assisted desorption electrospray ionization |
| APTDCI | Atmospheric pressure thermal desorption chemical ionization |
| V-EASI | Venturi easy ambient sonic-spray ionization |
| AFAI | Air flow-assisted ionization |
| LESA | Liquid extraction surface analysis |
| PTC-ESI | Pipette tip column electrospray ionization |
| AFADESI | Air flow-assisted desorption electrospray ionization |
| DEFFI | Desorption electro-flow focusing ionization |
| ESTASI | Electrostatic spray ionization |
| PASIT | Plasma-based ambient sampling ionization transmission |
| DAPCI | Desorption atmospheric pressure chemical ionization |
| DART | Direct analysis in real time |
| ASAP | Atmospheric pressure solid analysis probe |
| APTDI | Atmospheric pressure thermal desorption ionization |
| PADI | Plasma assisted desorption ionization |
| DBDI | Dielectric barrier discharge ionization |
| FAPA | Flowing atmospheric pressure afterglow |
| HAPGDI | Helium atmospheric pressure glow discharge ionization |
| APGDDI | Atmospheric pressure glow discharge desorption ionization |
| LTP | Low temperature plasma |
| LS-APGD | Liquid sampling-atmospheric pressure glow discharge |
| MIPDI | Microwave induced plasma desorption ionization |
| MFGDP | Microfabricated glow discharge plasma |
| RoPPI | Robotic plasma probe ionization |
| PLASI | Plasma spray ionization |
| MALDESI | Matrix assisted laser desorption electrospray ionization |
| ELDI | Electrospray laser desorption ionization |
| LDTD | Laser diode thermal desorption |
| LAESI | Laser ablation electrospray ionization |
| CALDI | Charge assisted laser desorption ionization |
| LA-FAPA | Laser ablation flowing atmospheric pressure afterglow |
| LADESI | Laser assisted desorption electrospray ionization |
| LDESI | Laser desorption electrospray ionization |
| LEMS | Laser electrospray mass spectrometry |
| LSI | Laser spray ionization |
| IR-LAMICI | Infrared laser ablation metastable induced chemical ionization |
| LDSPI | Laser desorption spray post-ionization |
| PAMLDI | Plasma assisted multiwavelength laser desorption ionization |
| HALDI | High voltage-assisted laser desorption ionization |
| PALDI | Plasma assisted laser desorption ionization |
| ESSI | Extractive electrospray ionization |
| PESI | Probe electrospray ionization |
| ND-ESSI | Neutral desorption extractive electrospray ionization |
| PS | Paper spray |
| DIP-APCI | Direct inlet probe-atmospheric pressure chemical ionization |
| TS | Touch spray |
| Wooden-tip | Wooden-tip electrospray |
| CBS-SPME | Coated blade spray solid phase microextraction |
| TSI | Tissue spray ionization |
| RADIO | Radiofrequency acoustic desorption ionization |
| LIAD-ESI | Laser induced acoustic desorption electrospray ionization |
| SAWN | Surface acoustic wave nebulization |
| UASI | Ultrasonication-assisted spray ionization |
| SPA-nanoESI | Solid probe assisted nanoelectrospray ionization |
| PAUSI | Paper assisted ultrasonic spray ionization |
| DPESI | Direct probe electrospray ionization |
| ESA-Py | Electrospray assisted pyrolysis ionization |
| APPIS | Ambient pressure pyroelectric ion source |
| RASTIR | Remote analyte sampling transport and ionization relay |
| SACI | Surface activated chemical ionization |
| DEMI | Desorption electrospray metastable-induced ionization |
| REIMS | Rapid evaporative ionization mass spectrometry |
| SPAM | Single particle aerosol mass spectrometry |
| TDAMS | Thermal desorption-based ambient mass spectrometry |
| MAII | Matrix assisted inlet ionization |
| SAII | Solvent assisted inlet ionization |
| SwiFERR | Switched ferroelectric plasma ionizer |
| LPTD | Leidenfrost phenomenon assisted thermal desorption |

According to an embodiment the ambient ionisation ion source may comprise a rapid evaporative ionisation mass spectrometry ("REIMS") ion source wherein a RF voltage is applied to one or more electrodes in order to generate smoke, aerosol or vapour by Joule heating.

However, it will be appreciated that other ambient ion sources including those referred to above may also be utilised. For example, according to another embodiment the ambient ionisation ion source may comprise a laser ionisation ion source. According to an embodiment the laser ionisation ion source may comprise a mid-IR laser ablation ion source. For example, there are several lasers which emit radiation close to or at 2.94 μm which corresponds with the peak in the water absorption spectrum. According to various embodiments the ambient ionisation ion source may comprise a laser ablation ion source having a wavelength close to 2.94 μm on the basis of the high absorption coefficient of water at 2.94 μm. According to an embodiment the laser ablation ion source may comprise a Er:YAG laser which emits radiation at 2.94 μm.

Other embodiments are contemplated wherein a mid-infrared optical parametric oscillator ("OPO") may be used to produce a laser ablation ion source having a longer wavelength than 2.94 μm. For example, an Er:YAG pumped ZGP-OPO may be used to produce laser radiation having a wavelength of e.g. 6.1 μm, 6.45 μm or 6.73 μm. In some situations it may be advantageous to use a laser ablation ion source having a shorter or longer wavelength than 2.94 μm since only the surface layers will be ablated and less thermal damage may result. According to an embodiment a Co:MgF$_2$ laser may be used as a laser ablation ion source wherein the laser may be tuned from 1.75-2.5 μm. According to another embodiment an optical parametric oscillator ("OPO") system pumped by a Nd:YAG laser may be used to produce a laser ablation ion source having a wavelength between 2.9-3.1 μm. According to another embodiment a CO$_2$ laser having a wavelength of 10.6 μm may be used to generate the aerosol, smoke or vapour.

According to other embodiments the ambient ionisation ion source may comprise an ultrasonic ablation ion source, or a hybrid electrosurgical-ultrasonic ablation source that generates a liquid sample which is then aspirated as an aerosol. The ultrasonic ablation ion source may comprise a focused or unfocussed ultrasound.

According to an embodiment the first device for generating aerosol, smoke or vapour from one or more regions of a target may comprise an tool which utilises an RF voltage, such as continuous RF waveform. According to other embodiments a radiofrequency tissue dissection system may be used which is arranged to supply pulsed plasma RF energy to a tool. The tool may comprise, for example, a PlasmaBlade®. Pulsed plasma RF tools operate at lower temperatures than conventional electrosurgical tools (e.g. 40-170° C. c.f. 200-350° C.) thereby reducing thermal injury depth. Pulsed waveforms and duty cycles may be used for both cut and coagulation modes of operation by inducing electrical plasma along the cutting edge(s) of a thin insulated electrode.

According to an embodiment the first device comprises a surgical water/saline jet device such as a resection device, a hybrid of such device with any of the other devices herein, an electrosurgery argon plasma coagulation device, and/or a hybrid argon plasma coagulation and water/saline jet device. According to an embodiment the first device comprises or forms part of an ambient ion or ionisation source; or said first device generates said aerosol, smoke or vapour from the target plant material and contains ions and/or is subsequently ionised by an ambient ion or ionisation source, or other ionisation source.

Optionally, the first device comprises or forms part of a device, or an ion source, selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a hybrid CUSA-diathermy device; (xxii) a focussed or unfocussed ultrasonic ablation device; (xxiii) a hybrid focussed or unfocussed ultrasonic ablation and diathermy device; (xxiv) a microwave resonance device; (xxv) a pulsed plasma RF dissection device; (xxvi) an argon plasma coagulation device; (xxvi) a hybrid pulsed plasma RF dissection and argon plasma coagulation device; (xxvii) a hybrid pulsed plasma RF dissection and JeDI device; (xxviii) a surgical water/saline jet device; (xxix) a hybrid electrosurgery and argon plasma coagulation device; and (xxx) a hybrid argon plasma coagulation and water/saline jet device.

Optionally, the step of using said first device to generate aerosol, smoke or vapour comprises contacting said target plant material with one or more electrodes.

Optionally, said one or more electrodes comprises either: (i) a monopolar device, wherein said method optionally further comprises providing a separate return electrode; (ii) a bipolar device; or (iii) a multi-phase RF device, wherein said method optionally further comprises providing a separate return electrode or electrodes.

Optionally, said one or more electrodes comprise or forms part of a rapid evaporation ionization mass spectrometry ("REIMS") device.

Optionally, said method further comprises applying an AC or RF voltage to said one or more electrodes in order to generate said aerosol, smoke or vapour.

Optionally, the step of applying said AC or RF voltage to said one or more electrodes further comprises applying one or more pulses of said AC or RF voltage to said one or more electrodes.

Optionally, said step of applying said AC or RF voltage to said one or more electrodes causes heat to be dissipated into said target plant material.

Optionally, said step of using said first device to generate aerosol, smoke or vapour from one or more regions of the target further comprises irradiating the target plant material with a laser.

Optionally, said first device generates aerosol from one or more regions of the target plant material by direct evaporation or vaporisation of target material from said target plant material by Joule heating or diathermy.

Optionally, said step of using said first device to generate aerosol, smoke or vapour from one or more regions of the target plant material further comprises directing ultrasonic energy into said target plant material.

Optionally, said aerosol comprises uncharged aqueous droplets, optionally comprising cellular material.

Optionally, at least 50%, 55%, 60%, 65%, 70%, 75%, 80%, 85%, 90% or 95% of the mass or matter generated by said first device and which forms said aerosol may be in the form of droplets.

The first device may be arranged and adapted to generate aerosol wherein the Sauter mean diameter ("SMD", $d_{32}$) of said aerosol is in a range: (i)<5 µm; (ii) 5-10 µm; (iii) 10-15 µm; (iv) 15-20 µm; (v) 20-25 µm; or (vi)>25 µm.

The aerosol may traverse a flow region with a Reynolds number (Re) in the range: (i)<2000; (ii) 2000-2500; (iii) 2500-3000; (iv) 3000-3500; (v) 3500-4000; or (vi)>4000.

Substantially at the point of generating the aerosol, the aerosol may comprise droplets having a Weber number (We) selected from the group consisting of: (i)<50; (ii) 50-100; (iii) 100-150; (iv) 150-200; (v) 200-250; (vi) 250-300; (vii) 300-350; (viii) 350-400; (ix) 400-450; (x) 450-500; (xi) 500-550; (xii) 550-600; (xiii) 600-650; (xiv) 650-700; (xv) 700-750; (xvi) 750-800; (xvii) 800-850; (xviii) 850-900; (xix) 900-950; (xx) 950-1000; and (xxi)>1000.

Substantially at the point of generating the aerosol, the aerosol may comprise droplets having a Stokes number (Sk) in the range: (i) 1-5; (ii) 5-10; (iii) 10-15; (iv) 15-20; (v) 20-25; (vi) 25-30; (vii) 30-35; (viii) 35-40; (ix) 40-45; (x) 45-50; and (xi)>50.

Substantially at the point of generating the aerosol, the aerosol may comprise droplets having a mean axial velocity selected from the group consisting of: (i)<20 m/s; (ii) 20-30 m/s; (iii) 30-40 m/s; (iv) 40-50 m/s; (v) 50-60 m/s; (vi) 60-70 m/s; (vii) 70-80 m/s; (viii) 80-90 m/s; (ix) 90-100 m/s; (x) 100-110 m/s; (xi) 110-120 m/s; (xii) 120-130 m/s; (xiii) 130-140 m/s; (xiv) 140-150 m/s; and (xv)>150 m/s.

Optionally, said aerosol comprises uncharged aqueous droplets, which may comprise cellular material.

Optionally, the method comprises ionising at least some of said aerosol, smoke or vapour, or analyte therein, so as to generate analyte ions; wherein said analyte ions are analysed to obtain said spectrometric data.

Optionally, the method comprises directing or aspirating at least some of said aerosol, smoke or vapour into a vacuum chamber of a mass and/or ion mobility spectrometer; and/or ionising at least some said aerosol, smoke or vapour, or the analyte therein, within a, or said, vacuum chamber of said spectrometer so as to generate a plurality of analyte ions.

Optionally, the method comprises causing said aerosol, smoke or vapour, or analyte therein, to impact upon a collision surface, optionally located within a, or the, vacuum chamber of said spectrometer, so as to generate the plurality of analyte ions.

Optionally, the collision surface may be heated. The collision surface may be heated to a temperature selected from the group consisting of: (i) about <100° C.; (ii) about 100-200° C.; (iii) about 200-300° C.; (iv) about 300-400° C.; (v) about 400-500° C.; (vi) about 500-600° C.; (vii) about 600-700° C.; (viii) about 700-800° C.; (ix) about 800-900° C.; (x) about 900-1000° C.; (xi) about 1000-1100° C.; and (xii) about >1100° C.

Optionally, the method comprises adding a matrix to said aerosol, smoke or vapour; optionally wherein said matrix is selected from the group consisting of: (i) a solvent for said aerosol, smoke or vapour or analyte therein; (ii) an organic solvent; (iii) a volatile compound; (iv) polar molecules; (v) water; (vi) one or more alcohols; (vii) methanol; (viii) ethanol; (ix) isopropanol; (x) acetone; (xi) acetonitrile; (xii) 1-butanol; (xiii) tetrahydrofuran; (xiv) ethyl acetate; (xv) ethylene glycol; (xvi) dimethyl sulfoxide; an aldehyde; (xviii) a ketone; (xiv) non-polar molecules; (xx) hexane; (xxi) chloroform; and (xxii) propanol.

Although various different ambient ionisation ion sources may be used in the method to analyse a variety of plant material targets, a method of REIMS analysis on a plant material will now be described in order to assist in understanding the embodiments.

Figure 1B:
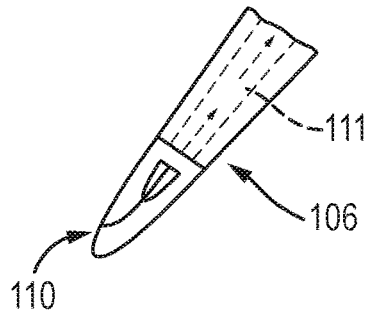
Figure 1C:
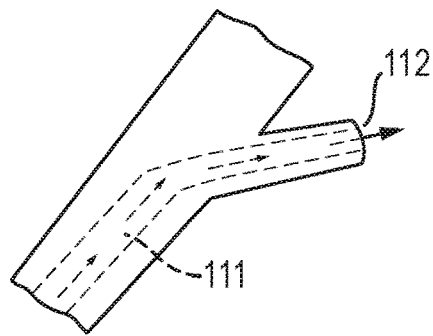
Figure 10:
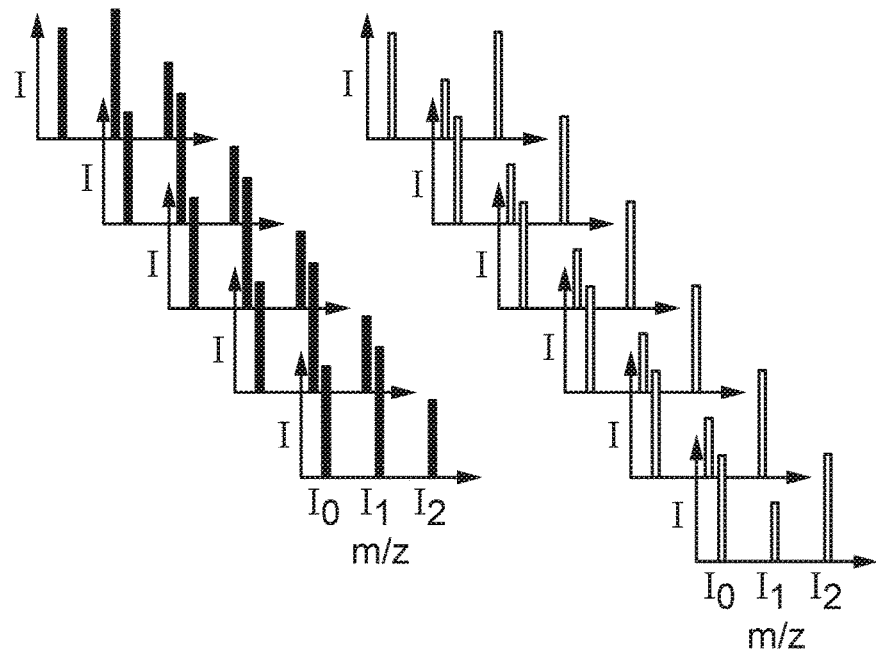
FIG. 10 shows a set of reference sample spectra obtained from two classes of known reference samples.

FIG. 1A shows apparatus that may be used to analyse a plant material. The apparatus comprises a pair of handheld electrodes 106,108 in the form of a forceps 102 (i.e. the first device); an RF power supply 103 for supplying an RF voltage to the electrodes 106,108; an inlet to a mass spectrometer 105; and tubing 104 connecting a port 112 at the rear end of the forceps 102 to the inlet of the spectrometer 105. The forceps 102 and RF power supply 103 may be configured such that the forceps 102 are bipolar forceps. As shown in FIG. 1B, an open entrance port 110 is provided in the tip of one of the electrodes 106 at the front of the forceps 102. This entrance port 110 opens up into a conduit 111 within the electrode 106. The conduit 111 extends through the electrode 106 to an exit port 112 in the rear of the forceps 102, as shown in FIG. 10.

As shown in FIG. 1A, the sample/target to be analysed may be provided in the form of a plant material 101. The forceps 102 may be inserted into contact with the plant material 101 so as to obtain biomass from the plant material 101 on the tips of the electrodes 106,108. The two electrodes 106,108 may be subsequently brought into close proximity with each other, e.g., by pinching the biomass between the tips of the forceps 102. The RF power supply 103 may be triggered, e.g., using a foot switch, so as to energise the electrodes 106,108. This causes the plant material biomass to be rapidly heated (e.g. by Joule or diathermy heating), due to its non-zero impedance, and smoke, aerosol or vapour to be emitted from the biomass. The smoke, aerosol or vapour may contain charged molecular species of analytes in the biomass.

The smoke, aerosol or vapour may then be captured or otherwise aspirated through the entrance port 110 and into the conduit 111 in the forceps 102. The smoke, aerosol or vapour is then drawn through the conduit 111, out of the exit port 112, along the tubing 104 and into the inlet of the mass spectrometer 105. The inherent vacuum system of the mass spectrometer may be used to draw the smoke, aerosol or vapour from the entrance port 110 to the inlet of the spectrometer 105. Alternatively, a Venturi device may be used to draw the smoke, aerosol or vapour from the entrance port 110 to the inlet of the spectrometer 105.

Figure 1D:
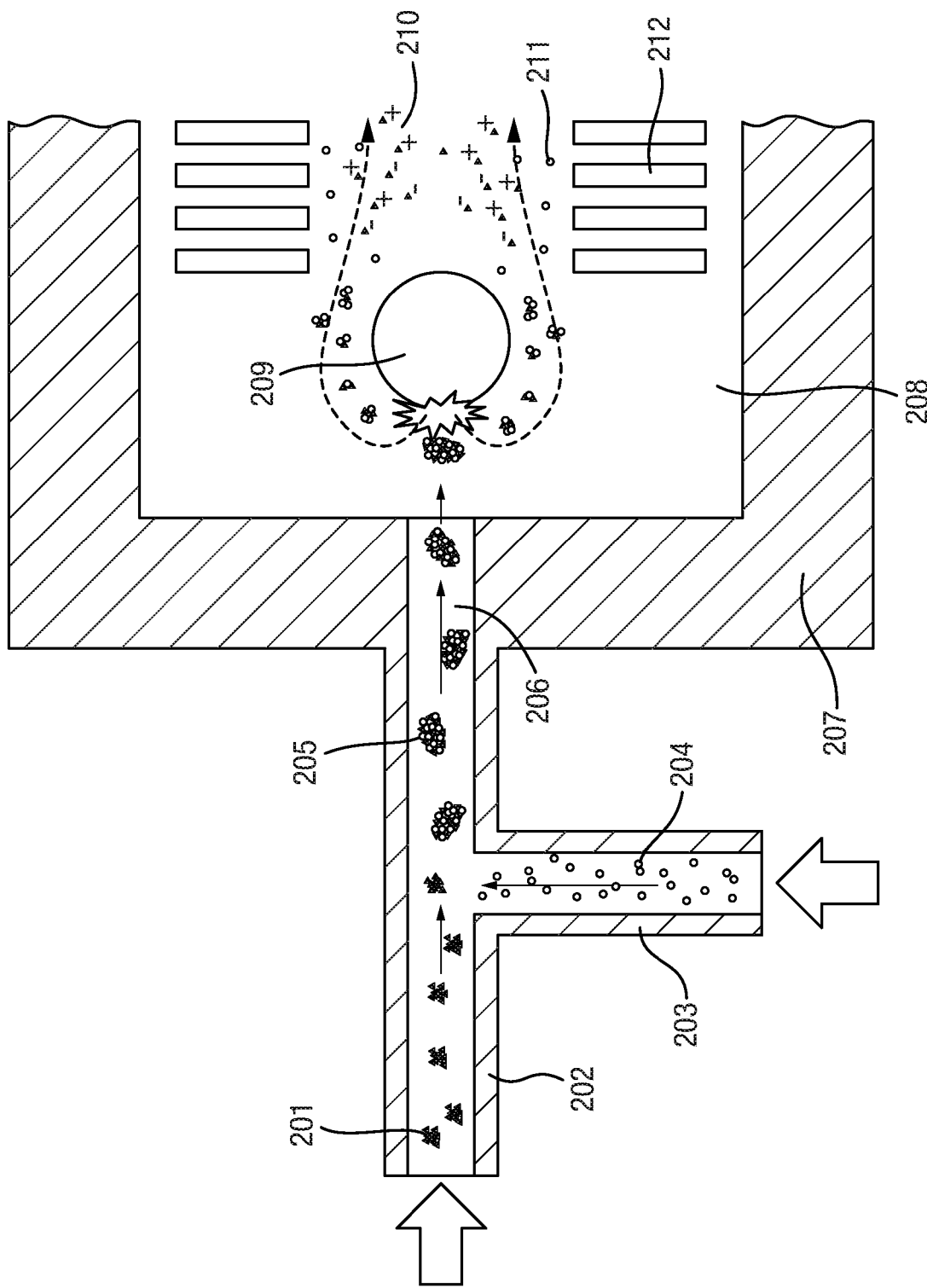
FIG. 1D shows an interface for ionizing aerosol from the target plant material.

FIG. 1D shows a schematic of an embodiment of an interface between the first device (e.g., forceps 102) and the mass spectrometer. The instrument may comprise an ion analyser 207 having an inlet 206 (which may correspond to inlet 5 in FIG. 1A), a vacuum region 208, a collision surface 209 and ion optics 212 (such as a Stepwave® ion guide) arranged within the vacuum region 208. The instrument also comprises a sample transfer tube 202 (corresponding to tubing 4 in FIG. 1) and a matrix introduction conduit 203. The sample transfer tube 202 has an inlet for receiving the smoke, aerosol or vapour sample 201 (which may correspond to that described in relation to FIG. 1) from a sample/target being investigated and an outlet that is connected to the inlet 206 of the ion analyser 207. The matrix introduction conduit 203 has an inlet for receiving a matrix compound and an outlet that intersects with the sample transfer tube 202 so as to allow the matrix 204 to be intermixed with the aerosol sample 201 in the sample transfer tube 202. A T-junction component may be provided at the junction between tubes 202, 203 and 206. The tubes 202, 203 and 206 may be removably inserted into the T-junction.

A method of operating the instrument shown in FIG. 1D will now be described. A sample/target, such as plant material, may be subjected to the REIMS technique. For example, a first device (e.g., forceps 102) may be used to generate an aerosol, e.g., as described above in relation to FIGS. 1A-1C. The aerosol particles 201 are then introduced into the inlet of the sample transfer tube 202. A matrix compound 204 is introduced into the inlet of the matrix introduction conduit 203. The aerosol particles 201 and matrix compound 204 are drawn towards the inlet 206 of the ion analyser 207 by a pressure differential caused by the vacuum chamber 208 being at a lower pressure than the inlets to the tubes 202, 203. The aerosol particles 201 may encounter the molecules of matrix compound 204 in, and downstream of, the region that the sample transfer tube 202 intersects with the matrix introduction conduit 203. The aerosol particles 201 intermix with the matrix 204 so as to form aerosol particles containing matrix molecules 205, in which both the molecular constituents of the aerosol sample 201 and the matrix compound 204 are present. The matrix molecules 204 may be in excess compared to the molecular constituents of aerosol sample 201.

The particles 205 may exit the sample transfer tube 202 and pass into the inlet 206 of the ion analyser 207. The particles 205 then enter into the decreased pressure region 208 and gain substantial linear velocity due to the adiabatic expansion of gas entering the vacuum region 208 from the sample transfer tube 202 and due to the associated free jet formation. The accelerated particles 205 may impact on the collision surface 209, where the impact event fragments the particles 205, leading to the eventual formation of gas phase ions 210 of the molecular constituents of the aerosol sample 201 and the formation of matrix molecules 211. The collision surface 209 may be controlled and maintained at a temperature that is substantially higher than the ambient temperature.

The matrix 204 includes a solvent for the analyte 201, such that the analyte 201 dissolves by the matrix 204, thereby eliminating intermolecular bonding between the analyte molecules 201. As such, when the dissolved analyte 205 is then collided with the collision surface 209, the dissolved analyte 205 will fragment into droplets and any given droplet is likely to contain fewer analyte molecules than it would if the matrix were not present. This in turn leads to a more efficient generation of analyte ions 210 when the matrix in each droplet is evaporated. The matrix may include a solvent for said aerosol, smoke or vapour or analyte therein; an organic solvent; a volatile compound; polar molecules; water; one or more alcohols; methanol; ethanol; isopropanol; acetone; acetonitrile; 1-butanol; tetrahydrofuran; ethyl acetate; ethylene glycol; dimethyl sulfoxide; an aldehyde; a ketone; non-polar molecules; hexane; chloroform; or (xxii) propanol. Isopropanol is of particular interest.

The matrix molecules 211 may freely diffuse into the vacuum. In contrast, the gas phase ions 210 of the molecular constituents of the aerosol sample 201 may be transferred by the ion optics 212 to an analysis region (not shown) of the ion analyser 207. The ions 210 may be guided to the analysis region by applying voltages to the ion optics 212.

The ion optics 212 may be a StepWave® ion guide. The collision surface may be positioned along and adjacent to the central axis of the large opening of a StepWave® ion guide. As will be understood by those skilled in the art, a StepWave® ion guide comprises two conjoined ion tunnel ion guides. Each ion guide comprises a plurality of ring or other electrodes wherein ions pass through the central aperture provided by the ring or other electrodes. Ions enter a first of the ion guides, along with any neutrals that may be present, and travel through the first ion guide. Ions are then directed orthogonally into a second of the ion guides and are transmitted therethrough. Transient DC voltages or potentials are applied to the electrodes to drive the ions through them. The StepWave® ion guide is based on stacked ring ion guide technology and is designed to maximise ion transmission from the source to the mass analyser. The device allows for the active removal of neutral contaminants, since the neutrals are not directed orthogonally into the second ion guide, thereby providing an enhancement to overall signal to noise. The design enables the efficient capture of the diffuse ion cloud entering a first lower stage which is then may focused into an upper ion guide for transfer to the ion analyser. The ions are then analysed by the ion analyser, which may comprise a mass spectrometer or an ion mobility spectrometer, or a combination of the two. As a result of the analysis, chemical information about the sample 201 may be obtained.

A liquid trap or separator may be provided between the first device (e.g., forceps 2) and the analyser, which captures or discards undesired liquids that are aspirated by the probe whilst may allowing the smoke, aerosol or vapour itself to pass relatively uninhibited to the mass spectrometer. This prevents undesired liquid from reaching the analyser without affecting the measurement of the smoke, aerosol or vapour. The liquid trap or separator may be arranged to capture the liquid for later disposal.

As described above, although embodiments have been described in which REIMS is used to generate the smoke, aerosol or vapour for analysis, other ambient ionisation techniques may be used such as, for example, Desorption Electrospray Ionisation ("DESI").

Desorption Electrospray Ionisation ("DESI") has also been found to be a particularly useful and convenient method for the real time rapid and direct analysis of plant material. DESI techniques allow direct and fast analysis of surfaces without the need for prior sample preparation. The technique will now be described in more detail with reference to FIGS. 1E-1F.

As shown in FIGS. 1E-1F, the DESI technique is an ambient ionisation method that involves directing a spray of (primary) electrically charged droplets 301 onto a plant material target 304. The electrospray mist is pneumatically directed at the target 304 by a sprayer 300 where subsequent splashed (secondary) droplets 305 carry desorbed ionised analytes (e.g. desorbed lipid ions). The sprayer 300 may be supplied with a solvent 306, a gas 307 (such as nitrogen) and a voltage from a high voltage source 308. After ionisation, the ions travel through air into an atmospheric pressure interface 309 of a mass spectrometer and/or mass analyser (not shown), e.g. via a transfer capillary 310. The ions may be analysed by the method described in relation to FIG. 1D, or by other methods. For example, the transfer capillary 310 of FIG. 1E may correspond to the sample transfer tube 202 in FIG. 1D. The transfer capillary 310 may be heated, e.g., to a temperature up to 500° C.

The DESI technique allows, for example, direct analysis of plant material, e.g., without requiring any advance sample preparation for the analysis.

Various embodiments are contemplated wherein analyte ions are generated from the target, aerosol, smoke or vapour, e.g., by an ambient ionisation ion source. The analyte ions, or ions derived therefrom, may be subjected either to: (i) mass analysis by a mass analyser such as a quadrupole mass analyser or a Time of Flight mass analyser; (ii) ion mobility analysis (IMS) and/or differential ion mobility analysis (DMA) and/or Field Asymmetric Ion Mobility Spectrometry (FAIMS) analysis; and/or (iii) a combination of firstly ion mobility analysis (IMS) and/or differential ion mobility analysis (DMA) and/or Field Asymmetric Ion Mobility Spectrometry (FAIMS) analysis followed by secondly mass analysis by a mass analyser such as a quadrupole mass analyser or a Time of Flight mass analyser (or vice versa). Various embodiments also relate to an ion mobility spectrometer and/or mass analyser and a method of ion mobility spectrometry and/or method of mass analysis.

Obtaining the spectrometric data may comprise recording the ion signal intensity of the ions derived from the smoke, aerosol or vapour as a function of one or more physicochemical property (or as a function of a property related thereto). For example, the ion signal intensity may be recorded as a function of mass to charge ratio and/or ion mobility. The location and/or size and/or pattern of peaks in this recorded ion signal may then be used to characterise or identify one or more analytes present in the smoke, aerosol or vapour.

Tandem mass spectrometry may be used to assign an analyte/compound to each of the peaks. For example, parent ions having a physicochemical property (e.g., mass to charge ratio) corresponding to that of a peak may be isolated (e.g., using a mass filter) and then fragmented or reacted so as to produce fragment or product ions. These fragment or product ions may then be analysed (e.g., by mass analysis) and their determined properties used to identify the parent ion giving rise to the peak in the ion signal. Such tandem mass spectrometry may be used, for example, to identify biomarkers in the spectrometric data.

The mass and/or ion mobility spectrometer may obtain data in negative ion mode only, positive ion mode only, or in both positive and negative ion modes. Positive ion mode spectrometric data may be combined or concatenated with negative ion mode spectrometric data. Negative ion mode can provide particularly useful spectra for classifying aerosol, smoke or vapour samples, such as aerosol, smoke or vapour samples from targets comprising lipids.

Ion mobility spectrometric data may be obtained using different ion mobility drift gases, or dopants may be added to the drift gas to induce a change in drift time of one or more species. This data may then be combined or concatenated. Other embodiments are contemplated wherein the first device for generating aerosol, smoke or vapour from the target may comprise an argon plasma coagulation ("APC") device. An argon plasma coagulation device involves the use of a jet of ionised argon gas (plasma) that is directed through a probe. The probe may be passed through an endoscope. Argon plasma coagulation is essentially a non-contact process as the probe is placed at some distance from the target. Argon gas is emitted from the probe and is then ionized by a high voltage discharge (e.g., 6 kV). High-frequency electric current is then conducted through the jet of gas, resulting in coagulation of the target on the other end of the jet. The depth of coagulation is usually only a few millimetres.

The first device, surgical or electrosurgical tool, device or probe or other sampling device or probe disclosed in any of the aspects or embodiments herein may comprise a non-contact sampling device, such as one or more of a hydro-sampling device, a water jet sampling device, an argon plasma coagulation device, a hybrid argon plasma coagulation device, a water jet device and a laser device.

A non-contact sampling device may be defined as a device arranged and adapted to dissect, fragment, liquefy, aspirate, fulgurate or otherwise disrupt plant material without physically contacting the material. Examples include laser devices, hydrosurgical devices, argon plasma coagulation devices and hybrid argon plasma coagulation devices.

As the non-contact device may not make physical contact with the material, the procedure may be seen as relatively safe and can be used to treat delicate material having low intracellular bonds.

According to the various embodiments herein, ion imaging may be used to generate an image or map of one or more properties of the target plant material. This may be achieved by using the first device to generate aerosol, smoke or vapour from multiple different regions of the target; ionising analytes in the smoke, aerosol or vapour originating from the different regions to produce analyte ions (or ions derived therefrom, e.g., fragment ions); and then analysing the analyte ions (or ions derived therefrom) to obtain spectrometric data for each of the regions of the target. The spectrometric data is correlated to the region of the target to which it relates (i.e. from where the smoke, aerosol or vapour that generated the spectrometric data originated from) so as to generate image or map data. An image or map of the target can then be generated based on the image or map data. For example, one or more properties of each region of the target may be determined from the spectrometric data and this may be included in the image or map data and hence mapped as a function of location within the target. The image or map data may then be displayed to a user.

The first device may be stepped between multiple spaced apart regions of the target so as to generate the aerosol, smoke or vapour from discrete regions of the target. Alternatively, a plurality of devices may be used to generate the aerosol, smoke or vapour from discrete regions of the target, optionally simultaneously. These plurality of devices may not move across the target, although may move into and out of engagement with the target. Spatial profiling of the target may therefore be performed (e.g., which does not perform a continuous map). Alternatively, the first device may be moved across or through the target continuously so as to generate aerosol, smoke or vapour from the different regions of the target. Any movements of the first device, or the plurality of devices, may be automated and controlled by a machine.

The spectrometric data for each region may be analysed and converted into data representative of the type, condition or constituent(s) of the material at that region in the target.

The representative data may then be displayed as an image or map showing the type, condition or constituents of the material as a function of location in the target.

For example, the representative data may indicate the type, level, presence and/or absence of one or more particular cell types and/or compounds at each of the regions in the target. For example, the spectrometric data may be used to identify and/or display the locations of a compound involved in a response to a stress factor.

The representative data may indicate the presence and/or distribution of one or more types of cells within the target.

Additionally, or alternatively, the representative data may indicate the presence and/or distribution of one or more types of compounds within the target.

Additionally, or alternatively, the representative data may indicate the type or level of biomarker in the target, and the distribution of the type or level of biomarkers within a target may be identified and/or displayed.

The ion imaging and map data may be generated and/or displayed in real-time. The position of at least a portion of the first device and/or another tool relative to the target may be displayed on the image or map, e.g., in real time. For example, the position of a sampling tool, such as a tool for resecting or ablating tissue, may be displayed on the map of the target.

Ion imaging mass and/or ion mobility spectrometry technology, such as DESI-MS and/or REIMS technology, may optionally be used to obtain the spectrometric data for the different regions of the target. A REIMS technology device may optionally be used in cutting and/or pointing mode.

This ion imaging analysis may optionally be combined with a further analysis of the plant or specimen. Details of further analysis methods and tools are provided elsewhere herein. Optionally, the results of mass and/or ion mobility spectrometry imaging may be correlated with the results of a further analysis.

Optionally, the method may involve the analysis of radio tracers. Positron Emission Tomography (PET) is a radiotracer imaging technique, in which tracer compounds labelled with positron-emitting radionuclides are injected into the plant that is the subject of the study. These radiotracer compounds can then be used to track biochemical and physiological processes in vivo. Positron-emitting isotopes of elements such as carbon, nitrogen, oxygen and fluorine may be processed to create a range of radio-tracer compounds which are similar to naturally occurring substances in the plant.

Optionally, the radio-tracer may be a compound labelled with $^{11}C$, $^{13}N$, $^{15}O$, and/or $^{18}F$. Optionally, it may be selected from $^{11}C$ methionine, $^{11}C$ flumazenil, $^{11}C$ raclopride, $^{13}N$ ammonia, $^{15}O$ carbon dioxide, $^{15}O$ water, $^{18}F$ Fluoro-deoxy-glucose, $^{18}F$ Fluoride ion, and/or $^{18}F$ Fluoro-mizonidazole.

Thus, e.g., if the biologically active molecule chosen is fluorodeoxyglucose (FDG), an analogue of glucose, the concentrations of tracer will indicate tissue metabolic activity as it corresponds to the regional glucose uptake. Optionally, a plant and/or specimen may be exposed to a radiotracer and the method may be used to analyse the location and/or concentration of a radio-tracer. Thus, the method may optionally be used to analyse the metabolism and/or transport of a compound labelled with a positron-emitting radionuclide.

Optionally, the method may involve analysing a target and, on the basis of one or more of the following making a determination that a plant is or is not suffering from a particular stress and/or disease: detecting a compound or biomarker; detecting an increase in a compound or biomarker; detecting a decrease in a compound or biomarker.

An increase or decrease may be determined by reference to a suitable reference, comparator or control. For example, the typical levels of phenolic compounds in a healthy, unstressed plant may be used as a reference, comparator or control, and an increase in the levels of phenolic compounds may be indicative of a nutrient deficiency, e.g., a deficiency in potassium, sulphur or magnesium.

The term "monitoring" and derivations of this term as used herein refer to the determination whether any changes take place/have taken place. Typically, it is determined whether any changes have taken place over time, i.e. since a previous time point. The change may, for example, be the development and/or progression of a disease or stress. Optionally, the method may involve analysing a target and, on the basis of detecting the presence, increase or decrease of a disease biomarker and/or stress biomarker, monitoring the development and/or progression of a disease and/or stress.

Optionally monitoring may involve analysing the response of a plant material to changed growth conditions, e.g., to the addition, increase, decrease, or removal of one or more stress factors. A deliberate change in growth conditions may be referred to as a "treatment".

Optionally, the method may involve analysing a target plant material and, on the basis of one or more of the following, determining that the plant material should or should not receive a particular treatment: identifying the genus, species and/or strain of the plant; detecting a biomarker, such as a disease and/or stress biomarker; detecting an increase in such a biomarker; and/or detecting a decrease in such a biomarker.

Optionally, the method may involve analysing a target plant material and, on the basis of one or more of the following, determining that the plant material has or has not responded a particular treatment: detecting a biomarker, such as a disease and/or stress biomarker; detecting an increase in such a biomarker; detecting a decrease in such a biomarker; and/or detecting the absence of such a biomarker.

Optionally, the method may involve analysing a target plant material and, on the basis of one or more of the following, administering a particular treatment to the plant material:

identifying the genus, species and/or strain of the plant; detecting a biomarker, such as a disease and/or stress biomarker; detecting an increase in such a biomarker; detecting a decrease in such a biomarker; and/or detecting the absence of such a biomarker.

Any of the methods of the invention may optionally involve the analysis of spectrometric data; more particularly, the analysis of spectrometric data from a target, e.g., a first target location. The terms "spectral data" and "spectrometric data" are used interchangeably herein.

The analysis of a target may be based solely on the analysis of spectral data, or it may optionally involve one or more further analytical tools, details of which are discussed elsewhere herein.

The spectrometric data may optionally provide direct and/or indirect information about the target.

Spectrometric data obtained from a target plant material, e.g., a first target location, may optionally be compared to one or more other spectrometric data, which may conveniently be referred to herein as "reference", "control" or "comparator" spectrometric data.

As explained elsewhere herein, analysing spectrometric data may optionally comprise analysing one or more sample spectra so as to classify an aerosol, smoke or vapour sample. This may comprise developing a classification model or library using one or more reference sample spectra, or may comprise using an existing library.

Optionally, an analysis may be made to determine whether spectrometric data obtained from a target matches or corresponds sufficiently to the "reference", "control" or "comparator" spectrometric data to make a positive determination. Optionally, a positive determination may be made if the spectrometric data corresponds more closely to one library entry than any other library entry.

The term "reference" spectrometric data is used herein to mean spectrometric data from a known plant type or compound. Reference spectrometric data may optionally be publicly available, or the skilled person may generate a library of reference spectrometric data. The method may optionally involve comparing the spectrometric data to one or more reference spectrometric data. If the spectrometric data obtained from a target matches or corresponds sufficiently to a reference spectrometric data, then optionally a positive determination may be made. If the spectrometric data obtained from a target does not match or correspond sufficiently to a reference spectrometric data, then optionally a negative determination may be made.

The term "comparator" spectrometric data is used herein to mean spectrometric data obtained from a second target location. The first and second target locations may be located in different targets, or at the different locations of the same target. The method may optionally involve comparing the spectrometric data to one or more comparator spectrometric data. If the spectrometric data obtained from a target matches or corresponds sufficiently to a comparator spectrometric data, then optionally a positive determination may be made. If the spectrometric data obtained from a target does not match or correspond sufficiently to a comparator spectrometric data, then optionally a negative determination may be made.

The term "control" spectrometric data is used herein to mean spectrometric data obtained from the first target at an earlier point in time. Control spectrometric data may, for example, be used when monitoring, e.g., nutrient availability, a disease, and/or the response to herbicide treatment. Any of the methods may optionally involve comparing the spectrometric data to one or more control spectrometric data. If the spectrometric data obtained from a target matches or corresponds sufficiently to a control spectrometric data, then optionally a positive determination may be made. If the spectrometric data obtained from a target does not match or correspond sufficiently to a control spectrometric data, then optionally a negative determination may be made.

By a "positive determination" is meant that the presence, identity and/or characteristics of a particular plant type, cell type and/or compound is determined. For example, a positive determination may, e.g., involve determining that a plant belongs to a particular species; and/or that a plant has a certain characteristic, such as, that it is herbicide resistant.

Thus, for example, if the spectrometric data of a first sample matches or corresponds sufficiently to a reference spectrometric data, then the plant material present in the first sample may optionally be identified as corresponding to the identity of the plant material from which the reference spectrometric data was obtained. If the spectrometric data of a first sample matches or corresponds sufficiently to a reference spectrometric data, then the plant material present in the first sample may optionally be characterised as having a characteristic corresponding to the characteristic of the plant material from which the reference spectrometric data was obtained.

As explained elsewhere herein, by determining or confirming the "identity" of a plant material is meant that at least some information about the identity is obtained, which may, for example, be at any taxonomic level. Thus, for example, if the reference spectrometric data is from *Alopecurus myosuroides*, then in one embodiment a match or sufficient correspondence may optionally be used to identify the first plant material as belonging to the genus *Alopecurus*, whereas in another embodiment a match or sufficient correspondence may optionally be used to identify the first plant material as belonging to the species *Alopecurus myosuroides*.

As another example, if the spectrometric data of a first sample matches or corresponds sufficiently to a comparator spectrometric data, then the plant material present in the first sample may optionally be identified as corresponding to the identity of the plant material from which the comparator spectrometric data was obtained. If the spectrometric data of a first sample matches or corresponds sufficiently to a comparator spectrometric data, then the plant material present in the first sample may optionally be characterised as having a characteristic corresponding to the characteristic of the plant material from which the comparator spectrometric data was obtained.

In other words, a match or sufficient correspondence to a reference or comparator spectrometric data respectively may be used to confirm that the first target plant material and the reference or comparator plant material respectively have the same identity, whereas the lack of a match or sufficient correspondence to a reference or comparator spectrometric data respectively may be used to confirm that the first target plant material and the reference or comparator entity respectively do not have the same identity.

By a "negative determination" is meant that it is determined that a target plant material does not have a particular identity and/or characteristic.

For example, a negative determination may involve determining that a particular target plant material does not have a certain characteristic.

For example, a negative determination may, e.g., involve determining that a plant of a particular taxonomic rank is not present; that a particular plant does not have a certain characteristic such as resistance to a particular herbicide; and/or that a particular compound is not being produced.

Thus, for example, if the spectrometric data of a first sample does not match or correspond sufficiently to a reference spectrometric data, then the target plant material present in the first sample may optionally be identified as not corresponding to the identity of the plant material from which the reference spectrometric data was obtained. If the spectrometric data of a first sample does not match or correspond sufficiently to a reference spectrometric data, then the target plant material present in the first sample may optionally be characterised as not having a characteristic corresponding to the characteristic of the plant material from which the reference spectrometric data was obtained.

As another example, if the spectrometric data of a first sample matches or corresponds sufficiently to a control spectrometric data, then a determination may be made that no, or no significant, change has taken place, whereas if the spectrometric data of a first sample does not match or correspond sufficiently to a control spectrometric data, then a determination may be made that a change, optionally a significant change, has taken place. Examples of a change may, for example, be a change in the plant's behaviour or its environment, such as, a change in the plant's growth rate; a change in the presence or levels of one or more stress factors; and the like.

As mentioned elsewhere herein, the method may optionally involve the analysis of biomarkers.

If a biomarker for a target plant material or stress status is known (e.g., from the prior art or from the work disclosed herein), then the method may optionally involve analysing the target for the presence of the spectrometric signal of that biomarker. The spectrometric signal of any biomarker may optionally be looked up in the literature, a database, or, if necessary, it may easily be determined experimentally.

For example, as shown herein, PI(14:1(9Z)/14:1(9Z)) is a biomarker for herbicide resistance at least in black grass, with a spectrometric signal of m/z about 749.426. When analysing a target plant material, such as black grass, to try to distinguish between herbicide sensitive and resistant strains, the method may optionally involve analysing the target for the presence of a spectrometric signal of m/z about 749.426.

Isobaric lipids with different head groups may optionally be differentiated by ion mobility.

Thus, optionally, the method may involve analysing the target for the presence of a spectrometric signal of one or more biomarkers, optionally selected from any of the biomarkers mentioned herein.

A biomarker for a stressed and/or diseased plant may optionally be determined, e.g., by subtracting the spectrometric signals obtained from a normal plant from the spectrometric signals obtained from a stressed and/or diseased plant, to arrive at spectrometric signals that are specific for the stressed and/or diseased plant.

Optionally, the analyte giving rise to a particular m/z and/or ion mobility spectrometric signal may optionally be further characterised, e.g., using MS/MS. Thus, ionic species in the mass and/or ion mobility spectra may optionally be identified based on techniques such as use of the ion mobility drift time and/or exact mass measurements (e.g., with a mass deviation<3 ppm), and/or MS/MS fragmentation patterns.

Thus, optionally, the method may involve analysing the target for the presence of a spectrometric signal of one or more biomarkers, optionally selected from any of the biomarkers mentioned herein.

The spectrometric data may comprise one or more sample spectra. Obtaining the spectrometric data may comprise obtaining the one or more sample spectra. Analysing the spectrometric data may comprise analysing the one or more spectra. Obtaining the one or more sample spectra may comprise a binning process to derive a set of time-intensity pairs and/or a set of sample intensity values for the one or more sample spectra. The binning process may comprise accumulating or histogramming ion detections and/or intensity values in a set of plural bins. Each bin in the binning process may correspond to particular range of times or time-based values, such as masses, mass to charge ratios, and/or ion mobilities. The bins in the binning process may each have a width equivalent to a width in Da or Th (Da/e)

in a range selected from a group consisting of: (i)<or >0.01; (ii) 0.01-0.05; (iii) 0.05-0.25; (iv) 0.25-0.5; (v) 0.5-1.0; (vi) 1.0-2.5; (vii) 2.5-5.0; and (viii)<or >5.0. It has been identified that bins having widths equivalent to widths in the range 0.01-1 Da or Th (Da/e) can provide particularly useful sample spectra for classifying some aerosol, smoke or vapour samples, such as samples obtained from tissues. The bins may or may not all have the same width. The widths of the bin in the binning process may vary according to a bin width function. The bin width function may vary with a time or time-based value, such as mass, mass to charge ratio and/or ion mobility. The bin width function may be non-linear (e.g., logarithmic-based or power-based, such as square or square-root based). The bin width function may take into account the fact that the time of flight of an ion may not be directly proportional to its mass, mass to charge ratio, and/or ion mobility. For example, the time of flight of an ion may be directly proportional to the square-root of its mass and/or mass to charge ratio.

The terms "spectrometric library" and "spectrometric database" are used interchangeably herein.

The skilled person may use any publicly available spectrometric data as reference spectrometric data. Examples of useful databases are: LipidMaps, LipidBlast and LipidXplorer, details of which are provided in the following publications: "LipidBlast—in-silico tandem mass spectrometry database for lipid identification" by Kind et al., Nat Methods. 2013 August; 10(8): 755-758; "LipidXplorer: A Software for Consensual Cross-Platform Lipidomics" by Herzog et al. PLoS ONE 7(1): e29851; and "Lipid classification, structures and tools" by Fahy et al. Biochimica et Biophysica Acta (BBA)—Molecular and Cell Biology of Lipids, Volume 1811, Issue 11, November 2011, Pages 637-647, Lipidomics and Imaging Mass Spectrometry, see also http://www.lipidmaps.org/.

Alternatively or in addition, the skilled person may construct a spectrometric library by obtaining spectrometric data from one or more samples, which may optionally, include type culture strains and/or environmental isolates; in the case of a compound, the sample(s) may optionally be purchased or synthesised.

The generation of a spectrometric library from plants may optionally be combined with a further analysis tool, e.g., taxonomic classification and/or histology. For example, the tool may be DNA analysis. This may involve DNA sequencing, optionally preceded by DNA isolation and/or amplification using, e.g., PCR.

The step of analysing the spectrometric data may comprise analysing one or more sample spectra so as to classify an aerosol, smoke or vapour sample.

Analysing the one or more sample spectra may comprise unsupervised analysis of the one or more sample spectra (e.g., for dimensionality reduction) and/or supervised analysis (e.g., for classification) of the one or more sample spectra.

Analysing the one or more sample spectra may comprise unsupervised analysis (e.g., for dimensionality reduction) followed by supervised analysis (e.g., for classification).

Analysing the one or more sample spectra may comprise using one or more of: (i) univariate analysis; (ii) multivariate analysis; (iii) principal component analysis (PCA); (iv) linear discriminant analysis (LDA); (v) maximum margin criteria (MMC); (vi) library-based analysis; (vii) soft independent modelling of class analogy (SIMCA); (viii) factor analysis (FA); (ix) recursive partitioning (decision trees); (x) random forests; (xi) independent component analysis (ICA); (xii) partial least squares discriminant analysis (PLS-DA); (xiii) orthogonal (partial least squares) projections to latent structures (OPLS); (xiv) OPLS discriminant analysis (OPLS-DA); (xv) support vector machines (SVM); (xvi) (artificial) neural networks; (xvii) multilayer perceptron; (xviii) radial basis function (RBF) networks; (xix) Bayesian analysis; (xx) cluster analysis; (xxi) a kernelized method; (xxii) subspace discriminant analysis; (xxiii) k-nearest neighbours (KNN); (xxiv) quadratic discriminant analysis (QDA); (xxv) probabilistic principal component Analysis (PPCA); (xxvi) non negative matrix factorisation; (xxvii) k-means factorisation; (xxviii) fuzzy c-means factorisation; and (xxix) discriminant analysis (DA).

Analysing the one or more sample spectra may comprise a combination of the foregoing analysis techniques, such as PCA-LDA, PCA-MMC, PLS-LDA, etc.

Analysing the one or more sample spectra may comprise developing a classification model and/or library using one or more reference sample spectra.

Analysing the one or more sample spectra may comprise performing linear discriminant analysis (LDA) (e.g., for classification) after performing principal component analysis (PCA) (e.g., for dimensionality reduction).

Analysing the one or more sample spectra may comprise performing a maximum margin criteria (MMC) process (e.g., for classification) after performing principal component analysis (PCA) (e.g., for dimensionality reduction)

Analysing the one or more sample spectra may comprise defining one or more classes within a classification model and/or library Analysing the one or more sample spectra may comprise defining one or more classes within a classification model and/or library manually or automatically according to one or more class criteria The one or more class criteria for each class may be based on one or more of: (i) a distance (e.g., squared or root-squared distance and/or Mahalanobis distance and/or (variance) scaled distance) between one or more pairs of reference points for reference sample spectra within a classification model space; (ii) a variance value between groups of reference points for reference sample spectra within a classification model space; and (iii) a variance value within a group of reference points for reference sample spectra within a classification model space.

The one or more classes may each be defined by one or more class definitions.

The one or more class definitions may comprise one or more of: (i) a set of one or more reference points for reference sample spectra, values, boundaries, lines, planes, hyperplanes, variances, volumes, Voronoi cells, and/or positions, within a classification model space; and (ii) one or more positions within a hierarchy of classes.

Analysing the one or more sample spectra may comprise using a classification model and/or library, for example a classification model and/or library as described above, to classify one or more sample spectra as belonging to one or more classes of sample.

Analysing the one or more sample spectra may comprise classifying one or more sample spectra as belonging to one or more classes in a supervised and/or unsupervised manner.

Analysing the one or more sample spectra may comprise classifying one or more sample spectra manually or automatically according to one or more classification criteria.

The one or more classification criteria may be based on one or more class definitions.

The one or more class definitions may comprise one or more of: (i) a set of one or more reference points for reference sample spectra, values, boundaries, lines, planes, hyperplanes, variances, volumes, Voronoi cells, and/or positions, within a classification model space; and (ii) one or more positions within a hierarchy of classes.

The one or more classification criteria may comprise one or more of: (i) a distance (e.g., squared or root-squared distance and/or Mahalanobis distance and/or (variance) scaled distance) between a projected sample point for one or more sample spectra within a classification model space and a set of one or more reference points for one or more reference sample spectra, values, boundaries, lines, planes, hyperplanes, volumes, Voronoi cells, or positions, within the classification model space being below a distance threshold or being the lowest such distance; (ii) one or more projected sample points for one or more sample spectra within a classification model space being one side or other of one or more reference points for one or more reference sample spectra, values, boundaries, lines, planes, hyperplanes, or positions, within the classification model space; (iii) one or more projected sample points within a classification model space being within one or more volumes or Voronoi cells within the classification model space; (iv) a probability that one or more projected sample points for one or more sample spectra within a classification model space belong to a class being above a probability threshold or being the highest such probability; and (v) a probability or classification score being above a probability or classification score threshold or being the highest such probability or classification score.

By way of example, a number of different analysis techniques will now be described in more detail.

By way of example, a method of building a classification model using multivariate analysis of plural reference sample spectra will now be described.

Figure 9:
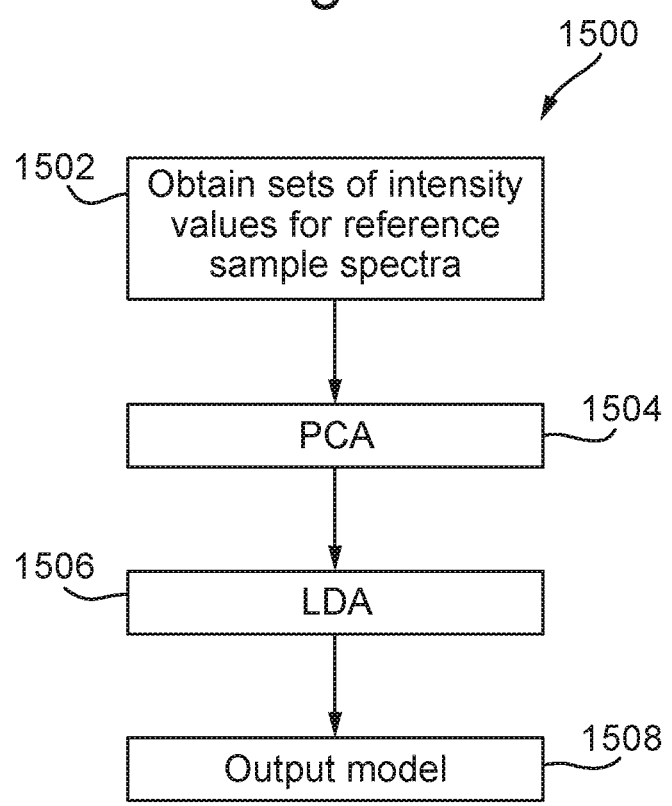
FIG. 9 shows a method of analysis that comprises building a classification model according to various embodiments.

FIG. 9 shows a method 1500 of building a classification model using multivariate analysis. In this example, the method comprises a step 1502 of obtaining plural sets of intensity values for reference sample spectra. The method then comprises a step 1504 of unsupervised principal component analysis (PCA) followed by a step 1506 of supervised linear discriminant analysis (LDA). This approach may be referred to herein as PCA-LDA. Other multivariate analysis approaches may be used, such as PCA-MMC. The PCA-LDA model is then output, for example to storage, in step 1508.

The multivariate analysis such as this can provide a classification model that allows an aerosol, smoke or vapour sample to be classified using one or more sample spectra obtained from the aerosol, smoke or vapour sample. The multivariate analysis will now be described in more detail with reference to a simple example.

FIG. 10 shows a set of reference sample spectra obtained from two classes of known reference samples. The classes may be any one or more of the classes of target described herein. However, for simplicity, in this example the two classes will be referred as a left-hand class and a right-hand class.

Each of the reference sample spectra has been pre-processed in order to derive a set of three reference peak-intensity values for respective mass to charge ratios in that reference sample spectrum. Although only three reference peak-intensity values are shown, it will be appreciated that many more reference peak-intensity values (e.g.,~100 reference peak-intensity values) may be derived for a corresponding number of mass to charge ratios in each of the reference sample spectra. In other embodiments, the reference peak-intensity values may correspond to: masses; mass to charge ratios; ion mobilities (drift times); and/or operational parameters.

Figure 11:
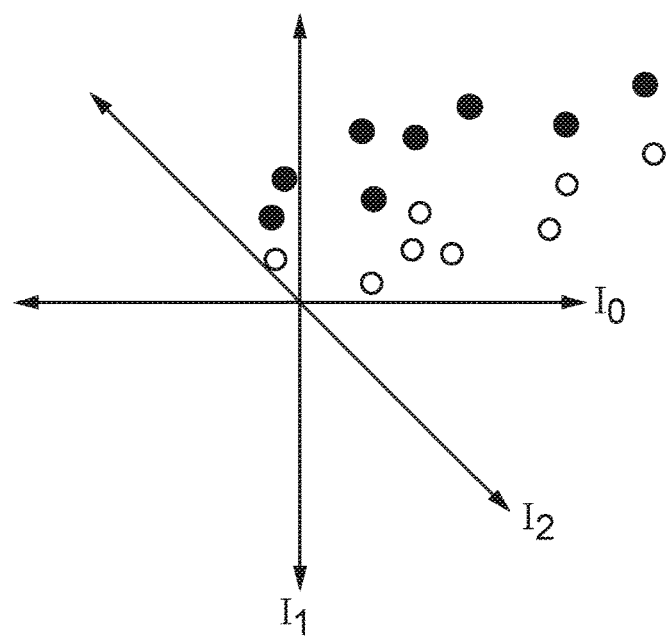
FIG. 11 shows a multivariate space having three dimensions defined by intensity axes, wherein the multivariate space comprises plural reference points, each reference point corresponding to a set of three peak intensity values derived from a reference sample spectrum.

FIG. 11 shows a multivariate space having three dimensions defined by intensity axes. Each of the dimensions or intensity axes corresponds to the peak-intensity at a particular mass to charge ratio. Again, it will be appreciated that there may be many more dimensions or intensity axes (e.g., ~100 dimensions or intensity axes) in the multivariate space. The multivariate space comprises plural reference points, with each reference point corresponding to a reference sample spectrum, i.e., the peak-intensity values of each reference sample spectrum provide the co-ordinates for the reference points in the multivariate space.

The set of reference sample spectra may be represented by a reference matrix D having rows associated with respective reference sample spectra, columns associated with respective mass to charge ratios, and the elements of the matrix being the peak-intensity values for the respective mass to charge ratios of the respective reference sample spectra.

In many cases, the large number of dimensions in the multivariate space and matrix D can make it difficult to group the reference sample spectra into classes. PCA may accordingly be carried out on the matrix D in order to calculate a PCA model that defines a PCA space having a reduced number of one or more dimensions defined by principal component axes. The principal components may be selected to be those that comprise or "explain" the largest variance in the matrix D and that cumulatively explain a threshold amount of the variance in the matrix D.

Figure 12:
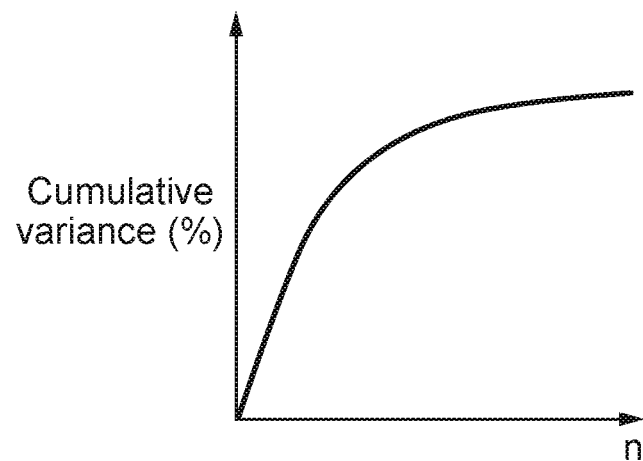
FIG. 12 shows a general relationship between cumulative variance and number of components of a PCA model.

FIG. 12 shows how the cumulative variance may increase as a function of the number n of principal components in the PCA model. The threshold amount of the variance may be selected as desired.

The PCA model may be calculated from the matrix D using a non-linear iterative partial least squares (NIPALS) algorithm or singular value decomposition, the details of which are known to the skilled person and so will not be described herein in detail. Other methods of calculating the PCA model may be used.

The resultant PCA model may be defined by a PCA scores matrix S and a PCA loadings matrix L. The PCA may also produce an error matrix E, which contains the variance not explained by the PCA model. The relationship between D, S, L and E may be:

$$D=SL^T+E \quad (1)$$

Figure 13:
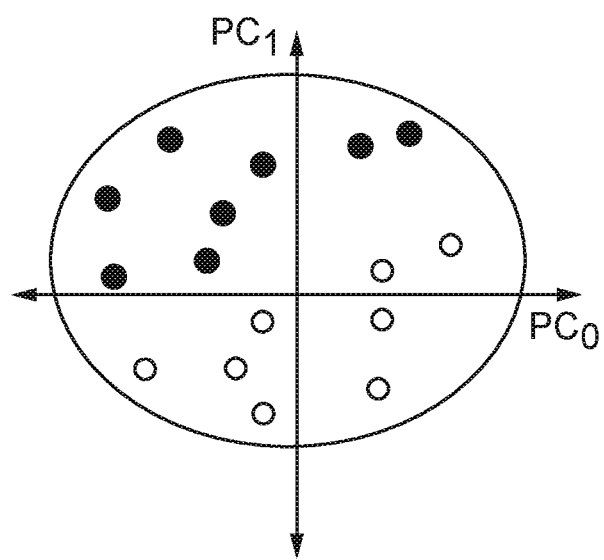
FIG. 13 shows a PCA space having two dimensions defined by principal component axes, wherein the PCA space comprises plural transformed reference points or scores, each transformed reference point or score corresponding to a reference point of FIG. 11.

FIG. 13 shows the resultant PCA space for the reference sample spectra of FIGS. 10 and 11. In this example, the PCA model has two principal components $PC_0$ and $PC_1$ and the PCA space therefore has two dimensions defined by two principal component axes. However, a lesser or greater number of principal components may be included in the PCA model as desired. It is generally desired that the number of principal components is at least one less than the number of dimensions in the multivariate space.

The PCA space comprises plural transformed reference points or PCA scores, with each transformed reference point or PCA score corresponding to a reference sample spectrum of FIG. 10 and therefore to a reference point of FIG. 11.

As is shown in FIG. 13, the reduced dimensionality of the PCA space makes it easier to group the reference sample spectra into the two classes. Any outliers may also be identified and removed from the classification model at this stage.

Further supervised multivariate analysis, such as multi-class LDA or maximum margin criteria (MMC), in the PCA space may then be performed so as to define classes and, optionally, further reduce the dimensionality.

As will be appreciated by the skilled person, multi-class LDA seeks to maximise the ratio of the variance between classes to the variance within classes (i.e., so as to give the largest possible distance between the most compact classes possible). The details of LDA are known to the skilled person and so will not be described herein in detail.

The resultant PCA-LDA model may be defined by a transformation matrix U, which may be derived from the PCA scores matrix S and class assignments for each of the transformed spectra contained therein by solving a generalised eigenvalue problem.

The transformation of the scores S from the original PCA space into the new LDA space may then be given by:

$$Z = SU \tag{2}$$

where the matrix Z contains the scores transformed into the LDA space.

Figure 14:
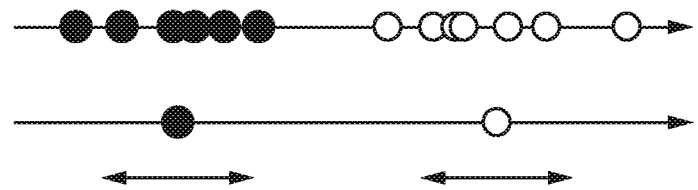
FIG. 14 shows a PCA-LDA space having a single dimension or axis, wherein the LDA is performed based on the PCA space of FIG. 13, the PCA-LDA space comprising plural further transformed reference points or class scores, each further transformed reference point or class score corresponding to a transformed reference point or score of FIG. 13.

FIG. 14 shows a PCA-LDA space having a single dimension or axis, wherein the LDA is performed in the PCA space of FIG. 13. As is shown in FIG. 14, the LDA space comprises plural further transformed reference points or PCA-LDA scores, with each further transformed reference point corresponding to a transformed reference point or PCA score of FIG. 13.

In this example, the further reduced dimensionality of the PCA-LDA space makes it even easier to group the reference sample spectra into the two classes. Each class in the PCA-LDA model may be defined by its transformed class average and covariance matrix or one or more hyperplanes (including points, lines, planes or higher order hyperplanes) or hypersurfaces or Voronoi cells in the PCA-LDA space.

The PCA loadings matrix L, the LDA matrix U and transformed class averages and covariance matrices or hyperplanes or hypersurfaces or Voronoi cells may be output to a database for later use in classifying an aerosol, smoke or vapour sample.

The transformed covariance matrix in the LDA space $V'_g$ for class g may be given by $$V'_g = U^T V_g U \tag{3}$$

where $V_g$ are the class covariance matrices in the PCA space.

The transformed class average position $z_g$ for class g may be given by $$S_g U = Z_g \tag{4}$$

where $s_g$ is the class average position in the PCA space.

By way of example, a method of using a classification model to classify an aerosol, smoke or vapour sample will now be described.

Figure 15:
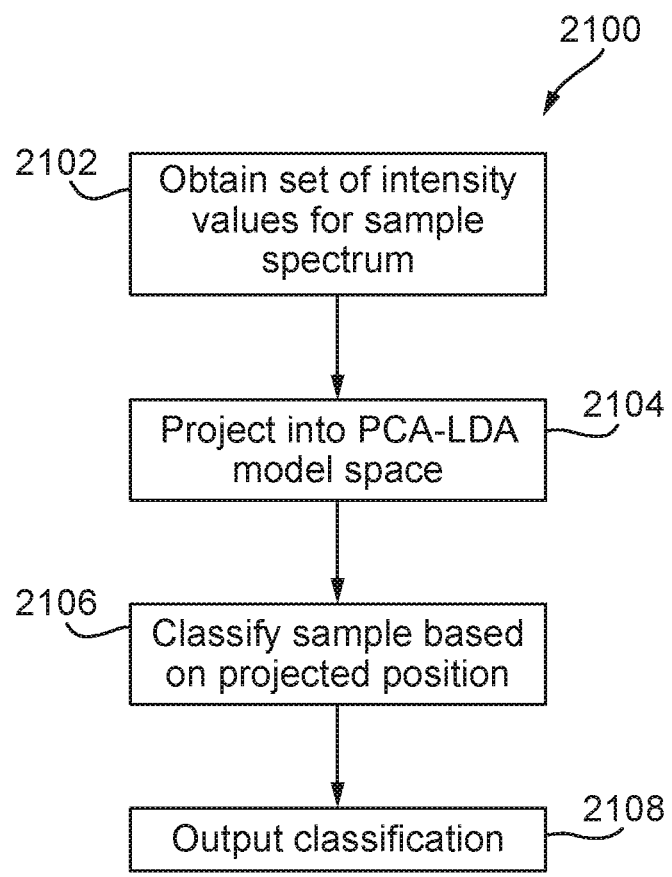
FIG. 15 shows a method of analysis that comprises using a classification model according to various embodiments.

FIG. 15 shows a method 2100 of using a classification model. In this example, the method comprises a step 2102 of obtaining a set of intensity values for a sample spectrum. The method then comprises a step 2104 of projecting the set of intensity values for the sample spectrum into PCA-LDA model space. Other classification model spaces may be used, such as PCA-MMC. The sample spectrum is then classified at step 2106 based on the project position and the classification is then output in step 2108.

Classification of an aerosol, smoke or vapour sample will now be described in more detail with reference to the simple PCA-LDA model described above.

Figure 16:
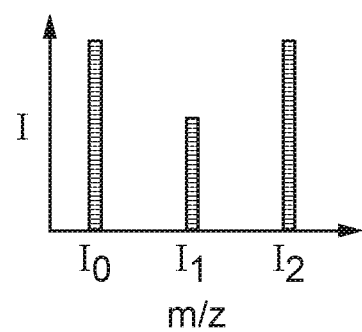
FIG. 16 shows a sample spectrum obtained from an unknown sample.

FIG. 16 shows a sample spectrum obtained from an unknown aerosol, smoke or vapour sample. The sample spectrum has been pre-processed in order to derive a set of three sample peak-intensity values for respective mass to charge ratios. As mentioned above, although only three sample peak-intensity values are shown, it will be appreciated that many more sample peak-intensity values (e.g., ~100 sample peak-intensity values) may be derived at many more corresponding mass to charge ratios for the sample spectrum. Also, as mentioned above, in other embodiments, the sample peak-intensity values may correspond to: masses; mass to charge ratios; ion mobilities (drift times); and/or operational parameters.

The sample spectrum may be represented by a sample vector $d_x$, with the elements of the vector being the peak-intensity values for the respective mass to charge ratios. A transformed PCA vector $s_x$ for the sample spectrum can be obtained as follows:

$$d_x L = s_x \tag{5}$$

Then, a transformed PCA-LDA vector $z_x$ for the sample spectrum can be obtained as follows:

$$s_x U = z_x \tag{6}$$

Figure 17:
FIG. 17 shows the PCA-LDA space of FIG. 14, wherein the PCA-LDA space further comprises a PCA-LDA projected sample point derived from the peak intensity values of the sample spectrum of FIG. 16.

FIG. 17 again shows the PCA-LDA space of FIG. 14. However, the PCA-LDA space of FIG. 17 further comprises the projected sample point, corresponding to the transformed PCA-LDA vector $z_x$, derived from the peak intensity values of the sample spectrum of FIG. 16.

In this example, the projected sample point is to one side of a hyperplane between the classes that relates to the right-hand class, and so the aerosol, smoke or vapour sample may be classified as belonging to the right-hand class.

Alternatively, the Mahalanobis distance from the class centres in the LDA space may be used, where the Mahalanobis distance of the point $z_x$ from the centre of class g may be given by the square root of:

$$(z_x - z_g)^T (V'_g)^{-1} (z_x - z_g) \tag{8}$$

and the data vector $d_x$ may be assigned to the class for which this distance is smallest.

In addition, treating each class as a multivariate Gaussian, a probability of membership of the data vector to each class may be calculated.

By way of example, a method of building a classification library using plural input reference sample spectra will now be described.

Figure 18:
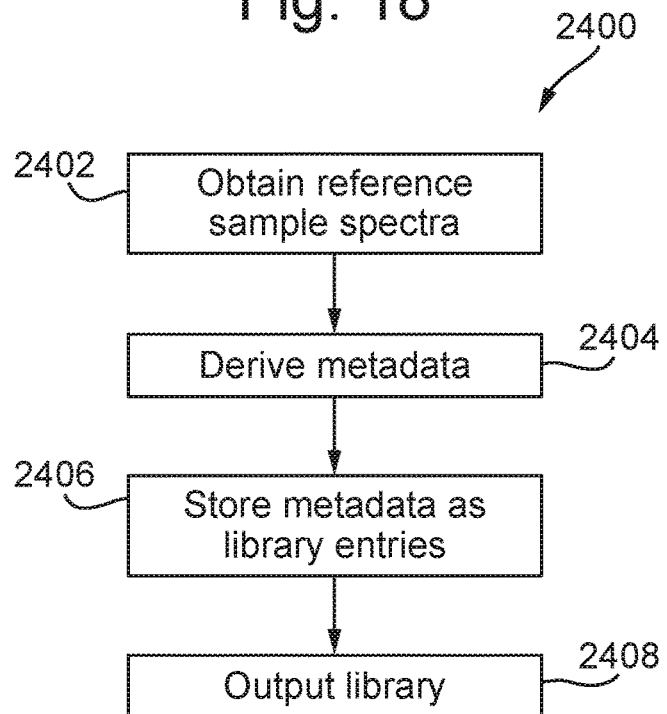
FIG. 18 shows a method of analysis that comprises building a classification library according to various embodiments.

FIG. 18 shows a method 2400 of building a classification library. In this example, the method comprises a step 2402 of obtaining plural input reference sample spectra and a step 2404 of deriving metadata from the plural input reference sample spectra for each class of sample. The method then comprises a step 2406 of storing the metadata for each class of sample as a separate library entry. The classification library is then output, for example to electronic storage, in step 2408.

A classification library such as this allows an aerosol, smoke or vapour sample to be classified using one or more sample spectra obtained from the aerosol, smoke or vapour sample. The library based analysis will now be described in more detail with reference to an example.

In this example, each entry in the classification library is created from plural pre-processed reference sample spectra that are representative of a class. In this example, the reference sample spectra for a class are pre-processed according to the following procedure:

First, a re-binning process is performed. In this embodiment, the data are resampled onto a logarithmic grid with abscissae:

$$x_i = \lfloor N_{chan} \log \frac{m}{M_{min}} / \log \frac{M_{max}}{M_{min}} \rfloor$$

where $N_{chan}$ is a selected value and denotes the nearest integer below x. In one example, $N_{chan}$ is $2^{12}$ or 4096.

Then, a background subtraction process is performed. In this embodiment, a cubic spline with k knots is then constructed such that p % of the data between each pair of knots lies below the curve. This curve is then subtracted from the data. In one example, k is 32. In one example, p is 5. A constant value corresponding to the q % quantile of the intensity subtracted data is then subtracted from each intensity. Positive and negative values are retained. In one example, q is 45.

Then, a normalisation process is performed. In this embodiment, the data are normalised to have mean $\bar{y}_i$. In one example, $\bar{y}_i = 1$.

An entry in the library then consists of metadata in the form of a median spectrum value $\mu_i$ and a deviation value $D_i$ for each of the $N_{chan}$ points in the spectrum.

The likelihood for the i'th channel is given by:

$$Pr(y_i|\mu_i, D_i) = \frac{1}{D_i} \frac{C^{C-1/2} \Gamma(C)}{\sqrt{\pi}\, \Gamma(C-1/2)} \frac{1}{\left(C + \frac{(y_i - \mu_i)^2}{D_i^2}\right)^C}$$

where $\frac{1}{2} \leq C < \infty$ and where $\Gamma(C)$ is the gamma function.

The above equation is a generalised Cauchy distribution which reduces to a standard Cauchy distribution for C=1 and becomes a Gaussian (normal) distribution as C→∞. The parameter $D_i$ controls the width of the distribution (in the Gaussian limit $D_i = \sigma_i$ is simply the standard deviation) while the global value C controls the size of the tails.

In one example, C is 3/2, which lies between Cauchy and Gaussian, so that the likelihood becomes:

$$Pr(y_i|\mu_i, D_i) = \frac{3}{4} \frac{1}{D_i} \frac{1}{(3/2 + (y_i - \mu_i)^2/D_i^2)^{3/2}}$$

For each library entry, the parameters $\mu_i$ are set to the median of the list of values in the i'th channel of the input reference sample spectra while the deviation $D_i$ is taken to be the interquartile range of these values divided by √2. This choice can ensure that the likelihood for the i'th channel has the same interquartile range as the input data, with the use of quantiles providing some protection against outlying data.

By way of example, a method of using a classification library to classify an aerosol, smoke or vapour sample will now be described.

Figure 19:
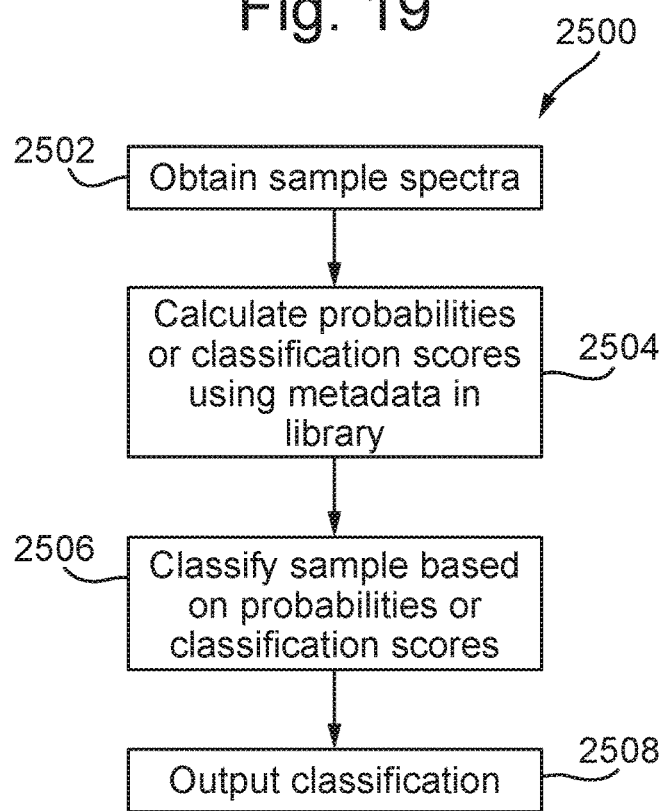
FIG. 19 shows a method of analysis that comprises using a classification library according to various embodiments.

FIG. 19 shows a method 2500 of using a classification library. In this example, the method comprises a step 2502 of obtaining a set of plural sample spectra. The method then comprises a step 2504 of calculating a probability or classification score for the set of plural sample spectra for each class of sample using metadata for the class entry in the classification library. The sample spectra are then classified at step 2506 and the classification is then output in step 2508.

Classification of an aerosol, smoke or vapour sample will now be described in more detail with reference to the classification library described above.

In this example, an unknown sample spectrum y is the median spectrum of a set of plural sample spectra. Taking the median spectrum y can protect against outlying data on a channel by channel basis.

The likelihood $L_s$ for the input data given the library entry s is then given by:

$$L_s = Pr(y|\mu, D) = \prod_{i=1}^{N_{chan}} Pr(y_i|\mu_i, D_i)$$

where $\mu_i$ and $D_i$ are, respectively, the library median values and deviation values for channel i. The likelihoods $L_s$ may be calculated as log likelihoods for numerical safety.

The likelihoods $L_s$ are then normalised over all candidate classes 's' to give probabilities, assuming a uniform prior probability over the classes. The resulting probability for the class $\tilde{s}$ is given by:

$$Pr(\tilde{s}|y) = \frac{L_{\tilde{s}}^{(1/F)}}{\sum_s L_s^{(1/F)}}$$

The exponent (1/F) can soften the probabilities which may otherwise be too definitive. In one example, F=100. These probabilities may be expressed as percentages, e.g., in a user interface.

Alternatively, RMS classification scores $R_s$ may be calculated using the same median sample values and derivation values from the library:

$$R_s(y, \mu, D) = \sqrt{\frac{1}{N_{chan}} \sum_{i=1}^{N_{chan}} \frac{(y_i - \mu_i)^2}{D_i^2}}$$

Again, the scores $R_s$ are normalised over all candidate classes 's'.

The aerosol, smoke or vapour sample may then be classified as belonging to the class having the highest probability and/or highest RMS classification score.

Any of the methods provided herein may optionally include a step of using one or more additional analytical tools. Such a tool may, for example, be selected from microscopic examination; nucleic acid analysis, for example, using restriction enzymes, hybridisation, polymerase chain reaction (PCR) amplification and/or sequencing; and/or testing for antigens. Such tools are well known in the art.

Data acquisition may, e.g., involve one or more of the following. The instrument may, e.g., be a medimass REIMS source on Xevo G2-XS QTof. The aerosol may, e.g., be analysed directly (no Venturi), or involve a Venturi such as a Venturi air jet pump-based ion transfer apparatus.

Sampling may, e.g., involve a diathermy generator and monopolar cutting electrode device, which may, e.g., be used to make 3-5 s burns. The plant material may, e.g., be placed on wetted tissue and "burns" sampled using the above-mentioned cutting device. Data acquisition may, e.g., use Tof MS in sensitivity mode; a scan rate of, e.g., 1 scan/s; polarity which may, e.g., be negative & positive polarity; a mass range of, e.g., 50-1200 m/z; and/or diathermy settings of, e.g., autocut mode 20 w.

Data analysis may, e.g., involve a progenesis QI bridge tool (RC3) and Progenesis QI v.2.2; an internal lockmass correction, e.g., applied on 255.2324 (palmitic acid); adaptive background subtraction; and/or a direct ionisation workflow.

Although the present invention has been described with reference to preferred embodiments, it will be understood by those skilled in the art that various changes in form and detail may be made without departing from the scope of the invention as set forth in the accompanying claims.

Example 1—Plant Speciation and Determination of Herbicide Susceptibility

Species of weed grass were sampled using a diathermy generator and monopolar cutting electrode device (referred to herein as iKnife technology). Details of the species are given in Table 1.1

TABLE 1.1

| Species | Wild-type | Target site resistant (TSR) | Multiple herbicide resistant (MHR) |
|---|---|---|---|
| Alopecurus myosuroides | Pellium (B-G PEL) | — | — |
| Alopecurus myosuroides | — | Oxford (B-G Ox) | — |
| Alopecurus myosuroides | — | Nottingham (B-G Nots) | — |
| Alopecurus myosuroides | — | — | Rothamsted (B-G Roth) |
| Lollium rigidum | Rye grass | — | — |

Leaves were removed from growing 2 week old cultured seedlings and directly sampled using the device. The aerosol/smoke generated from the grass was transferred to a mass spectrometer. In some experiments, this was done by a Venturi air jet pump-based ion transfer apparatus mounted in the orthogonal position relative to the atmospheric interface of a time of flight mass spectrometer, but in others, the aerosol/smoke generated from the grass was analysed directly without the use of a Venturi air jet pump-based ion transfer apparatus. A database of spectra was acquired in negative ion mode over 50-1200 m/z range and MVA models were created using Principal Components Analysis (PCA) for data reduction followed by Linear Discriminant Analysis (LDA). Spectra obtained from the test samples were compared to the model in real time giving a species level identification.

Using this method, the inventors were able to rapidly differentiate between leaf material originating from seedlings of various types of black-grass or ryegrass (see Table 1.1) based on differences in spectral features, particularly across the mass range 50-1200 m/z in negative ionization mode.

Figure 2:
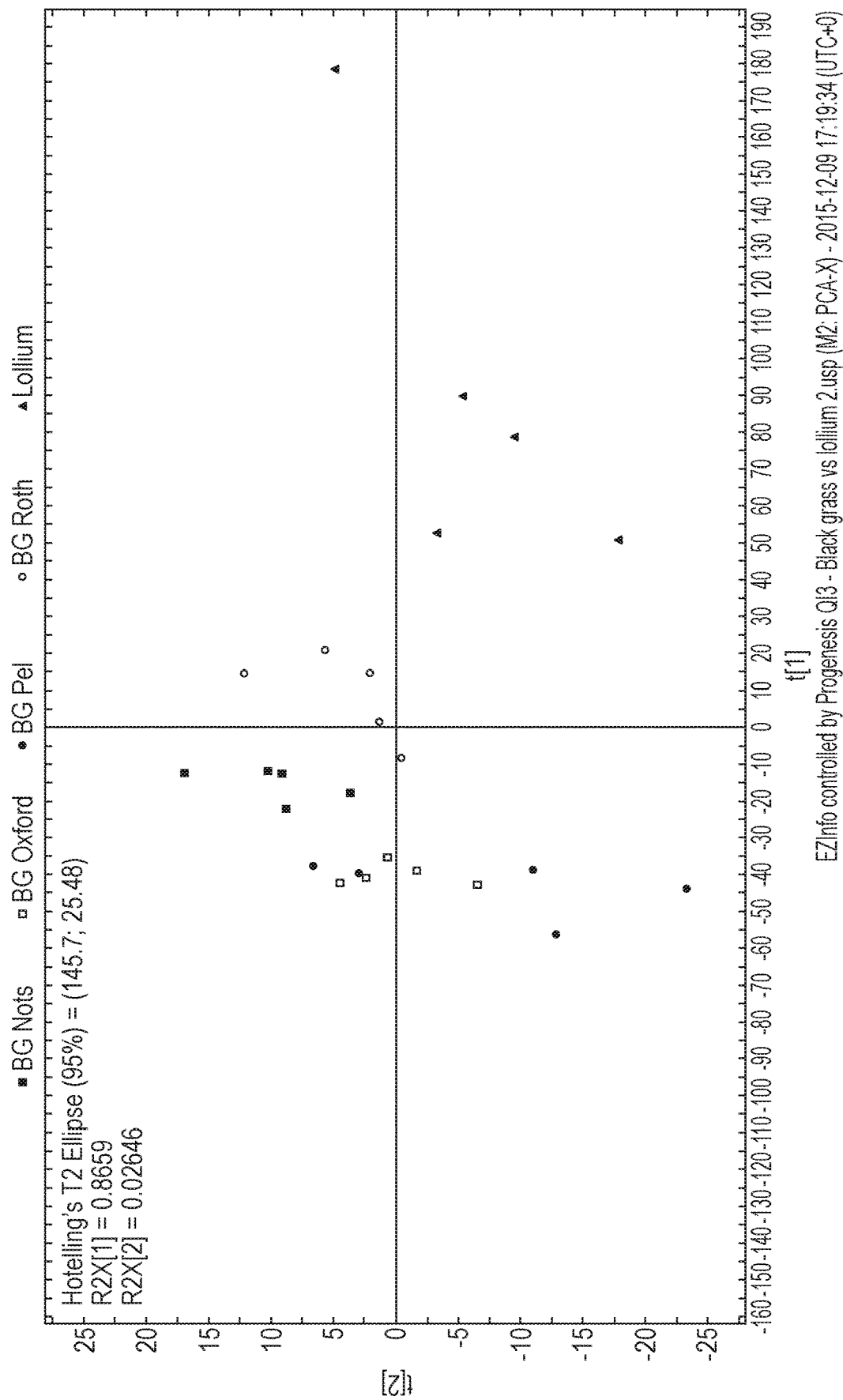
FIG. 2 shows results of Example 1; Shown is a PCA plot with pareto scaling; BG Nots stands for black grass Nottingham; BG Oxford stands for black grass Oxford; BG Pel stands for black grass Pellium; BG Roth stands for black grass Rothamsted; and Lollium stands for rye grass Lollium rigidum; See Also Table 2.1; For each species, 5 results from 2-3 biological replicates were obtained.
Figure 3:
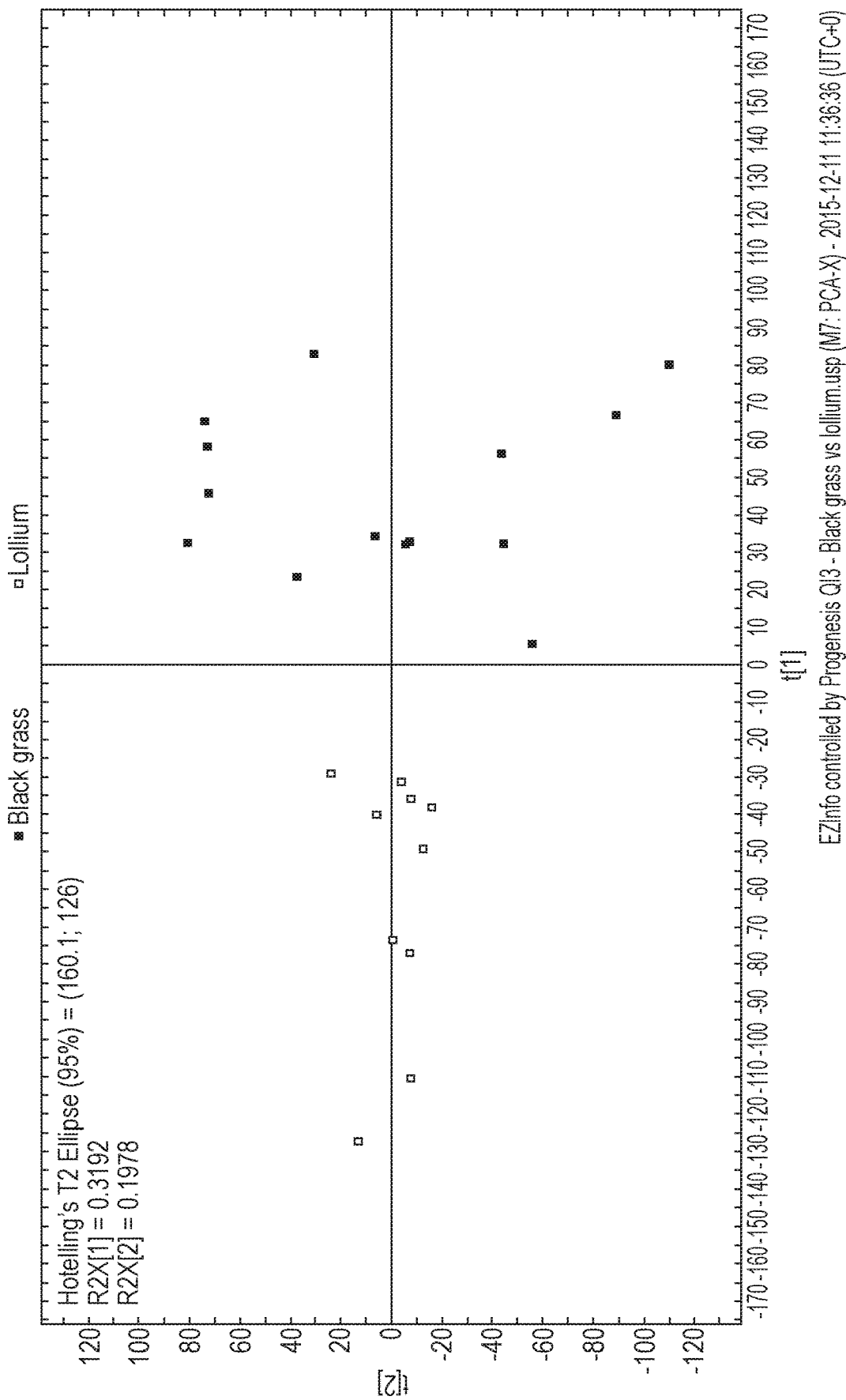
FIG. 3 shows results of Example 1; Supervised analysis was used to generate the shown OPLS-DA scores plot.
Figure 4:
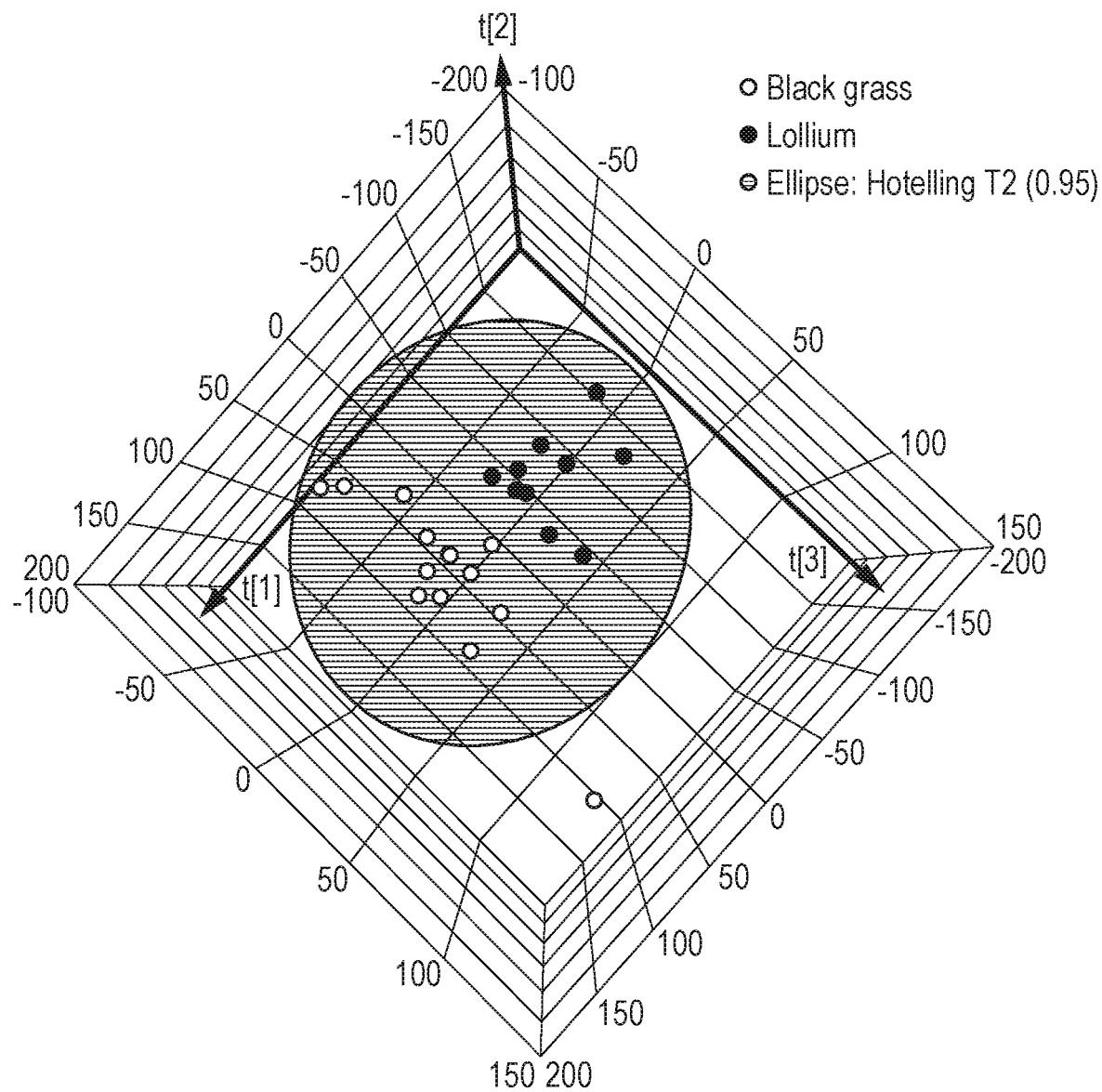
FIG. 4 shows results of Example 1; Shown is a 3D Principal component analysis scores plot (pareto scaling) showing unsupervised discrimination between wild type black-grass and annual ryegrass species.

A minimum of 3 biological replicates per species with 20 technical replicates of each specimen were used for robust model training. The full spectral fingerprint was subjected to PCA in order to reduce the data dimensionality and remove noise, followed by a LDA for classification. The models were subsequently verified with cross-validation and independent test set challenges. For results refer to FIG. 2, which shows a clear separation between rye grass and black grass, as well as a good separation between different black grass species; and FIG. 3 and FIG. 4, which show a clear separation between rye grass and the combined black grasses.

The acquired spectra featured fatty acids and very long chain fatty acids in the 150-500 m/z region, glycerophospholipids in the 600-900 region and triglycerides in the 900-1000 region in all cases. Several other small molecular weight compounds including members of the polyphenol (flavones-C-glyocides and anthocyanins); fatty acid and aromatic acid classes previously characterized in conventional ESI HRMS based metabolomics studies were also identified following REIMS technology analysis operated in the MS/MS acquisition mode.

The different plant species could be distinguished, in particular based on the profile of glycerophospholipid compounds, especially those belonging to the phosphatidyl-ethanolamine (PE), phosphatidyl-choline (PC) and/or phoshatidyl-inositol (PI) classes. These alterations in membrane composition are associated with herbicide tolerance traits. Thus, the method may be used to analyse susceptibility to herbicides.

A list of compounds that were found to be more or less abundant in one or more species compared to one or more other species tested is shown in Table 1.2.

TABLE 1.2

| m/z | Peak Width | IDs | Anova (p) | Max fold change | Highest mean | Lowest mean | Max abundance |
|---|---|---|---|---|---|---|---|
| 155.0360 | 0.17 | 1 | 5.17E−07 | 71.2 | Lollium | BG Pel | 11.8327 |
| 295.0697 | 0.17 | 1 | 4.4E−05 | 3.97 | Lollium | BG Pel | 53.2282 |
| 349.2758 | 0.17 | 1 | 0.00298 | 4.26 | BG Pel | Lollium | 23.4406 |
| 387.1298 | 0.17 | 2 | 0.12 | Infinity | BG Roth | BG Nots | 5.6713 |
| 407.1135 | 0.17 | 12 | 0.0685 | 8.55 | BG Roth | BG Pel | 8.0085 |
| 435.1518 | 0.17 | 0 | 0.491 | Infinity | BG Roth | BG Oxford | 3.6905 |
| 479.2577 | 0.13 | 1 | 0.471 | Infinity | BG Oxford | BG Nots | 0.0921 |
| 517.1728 | 0.17 | 1 | 0.141 | Infinity | Lollium | BG Nots | 2.5067 |
| 560.4678 | 0.17 | 1 | 0.446 | Infinity | BG Oxford | BG Roth | 2.5142 |
| 579.4373 | 0.17 | 0 | 0.719 | Infinity | BG Roth | BG Nots | 1.4880 |
| 596.2097 | 0.17 | 0 | 0.528 | 1.54 | BG Roth | BG Nots | 9.5520 |
| 665.2402 | 0.15 | 1 | 0.345 | Infinity | BG Pel | BG Nots | 2.5134 |
| 669.5659 | 0.13 | 1 | 0.509 | Infinity | BG Oxford | BG Nots | 0.0925 |
| 677.3451 | 0.17 | 1 | 0.519 | Infinity | BG Roth | BG Nots | 2.4189 |
| 739.3429 | 0.15 | 0 | 0.604 | Infinity | BG Oxford | BG Nots | 0.6394 |
| 739.4558 | 0.17 | 6 | 0.119 | 8.78 | BG Oxford | Lollium | 10.6035 |
| 741.4758 | 0.17 | 13 | 0.000229 | 3.15 | BG Pel | Lollium | 383.2134 |
| 742.4819 | 0.17 | 1 | 8.06E−05 | 3.18 | BG Pel | Lollium | 198.0521 |
| 743.4941 | 0.17 | 11 | 2.64E−05 | 4.76 | BG Oxford | Lollium | 478.4930 |

TABLE 1.2-continued

| m/z | Peak Width | IDs | Anova (p) | Max fold change | Highest mean | Lowest mean | Max abundance |
|---|---|---|---|---|---|---|---|
| 744.0069 | 0.17 | 0 | 0.02 | Infinity | Lollium | BG Nots | 9.5827 |
| 744.4981 | 0.17 | 1 | 2.93E−05 | 4.73 | BG Oxford | Lollium | 192.2238 |
| 745.0070 | 0.17 | 0 | 0.02 | Infinity | Lollium | BG Nots | 5.5903 |
| 749.4260 | 0.13 | 1 | 0.534 | Infinity | BG Pel | BG Roth | 0.0719 |
| 779.4627 | 0.15 | 1 | 0.0435 | Infinity | BG Oxford | BG Nots | 7.5642 |
| 855.7002 | 0.17 | 1 | 0.431 | Infinity | BG Pel | BG Roth | 0.5591 |
| 941.8797 | 0.17 | 0 | 0.0143 | Infinity | BG Roth | BG Nots | 10.1974 |
| 942.8790 | 0.17 | 0 | 0.144 | Infinity | BG Roth | BG Nots | 3.6316 |
| 976.7251 | 0.17 | 1 | 0.017 | Infinity | BG Oxford | BG Nots | 12.8782 |
| 1021.5873 | 0.17 | 1 | 0.31 | 5.71 | BG Pel | BG Nots | 13.0680 |
| 1033.6467 | 0.17 | 0 | 0.114 | Infinity | BG Roth | BG Nots | 12.9027 |
| 1058.0204 | 0.17 | 1 | 0.000171 | Infinity | Lollium | BG Nots | 14.7535 |

The compounds were identified through database searches based on their determined m/z. Identification details are shown for selected compounds in Table 1.3.

TABLE 1.3

| m/z | Description | Adducts | Formula | Score | Mass error (ppm) |
|---|---|---|---|---|---|
| 749.4260 | Common name: PI(14:1(9Z)/14:1(9Z)) Systematic name: 1,2-di-(9Z-tetradecenoyl)-sn-glycero-3-phospho-(1'-myo-inositol) | M − H | $C_{37}H_{67}O_{13}P$ | 32.5 | 1.74 |
| 517.1728 | Phellodensin E | M − H | $C_{26}H_{30}O_{11}$ | 34.1 | 2.4 |
| 742.4819 | Phosphatidylethanolamine (38:7) | M − H | $C_{43}H_{70}NO_8P$ | | 0.28 |
| 387.1298 | Secologanin* | M − H | C17H24O10 | 36.2 | 0.24 |
| | Verbenalin* | M − H | C17H24O10 | 36.2 | 0.24 |
| 743.4941 | PG(18:3(6Z,9Z,12Z)/16:0)** | M − H | $C_{40}H_{73}O_{10}P$ | 30.5 | 9.78 |
| | PG(18:3(9Z,12Z,15Z)/16:0)** | M − H | $C_{40}H_{73}O_{10}P$ | 30.5 | 9.78 |
| | PG(20:3(8Z,11Z,14Z)/14:0)** | M − H | $C_{40}H_{73}O_{10}P$ | 30.5 | 9.78 |
| | PG(20:2(11Z,14Z)/14:1 (9Z))** | M − H | $C_{40}H_{73}O_{10}P$ | 30.5 | 9.78 |
| | PG(17:2(9Z,12Z)/17:1 (9Z))** | M − H | $C_{40}H_{73}O_{10}P$ | 30.5 | 9.78 |
| | PG(18:2(9Z,12Z)/16:1(9Z))** | M − H | $C_{40}H_{73}O_{10}P$ | 30.5 | 9.78 |
| | PG(17:1(9Z)/17:2(9Z,12Z))** | M − H | $C_{40}H_{73}O_{10}P$ | 30.5 | 9.78 |
| | PG(16:1(9Z)/18:2(9Z,12Z))** | M − H | $C_{40}H_{73}O_{10}P$ | 30.5 | 9.78 |
| | PG(14:1(9Z)/20:2(11Z,14Z))** | M − H | $C_{40}H_{73}O_{10}P$ | 30.5 | 9.78 |
| | PG(16:0/18:3(9Z,12Z,15Z))** | M − H | $C_{40}H_{73}O_{10}P$ | 30.5 | 9.78 |
| | PG(16:0/18:3(6Z,9Z,12Z))** | M − H | $C_{40}H_{73}O_{10}P$ | 30.5 | 9.78 |

*= two possible identifications
**= 11 possible identifications

Figure 5:
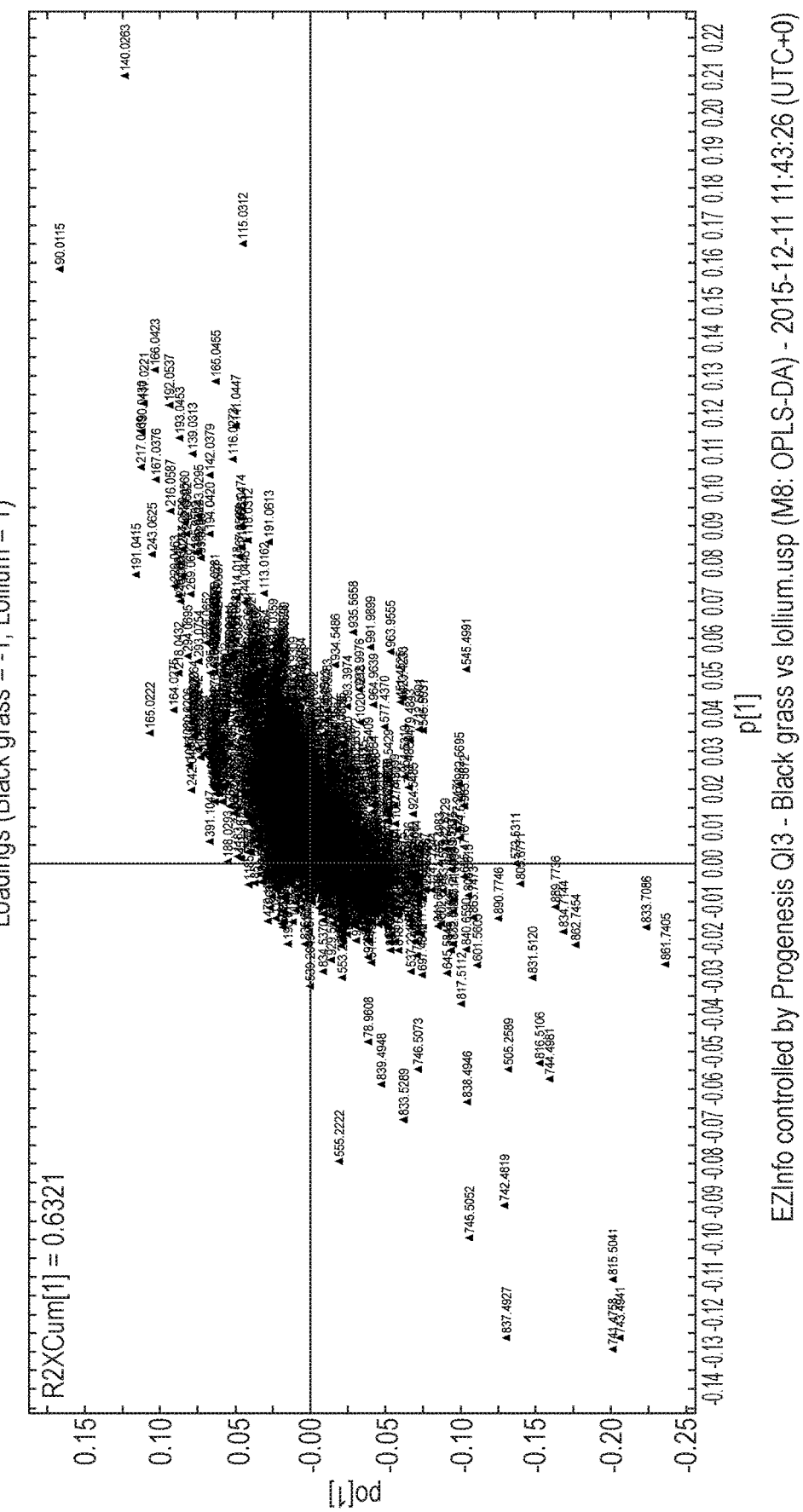
FIG. 5 shows results of Example 1; Shown is a an OPLS-DA loadings plot, which shows the m/z of compounds that are particularly abundance in black grass (bottom left quadrant) or in rye grass (top right quadrant)

FIG. 5 shows an OPLS-DA loadings plot, which shows the m/z of compounds that are particularly abundance in black grass (bottom left quadrant) or in rye grass (top right quadrant). Thus, it can be seen that the following are examples of m/z of compounds that were particularly highly abundant in black grass: 743.4941; 741.4758; 815.5041; 837.4927; 745.5052; 742.4819; 861.7405; 833.7086; 744.4981; 816.5106; 505.2589; 838.4946; 555.2222; 833.5289; 746.5073; 839.4948; 78.9608; 817.5112; 831.5120; 862.7454; 833.7086; and 861.7405. The following are examples of m/z of compounds that were particularly highly abundant in rye grass: 140.0263; 90.0115; 115.0312; 166.0423; 165.0455; 192.0537; 193.0453; and 139.0313.

Figure 6:
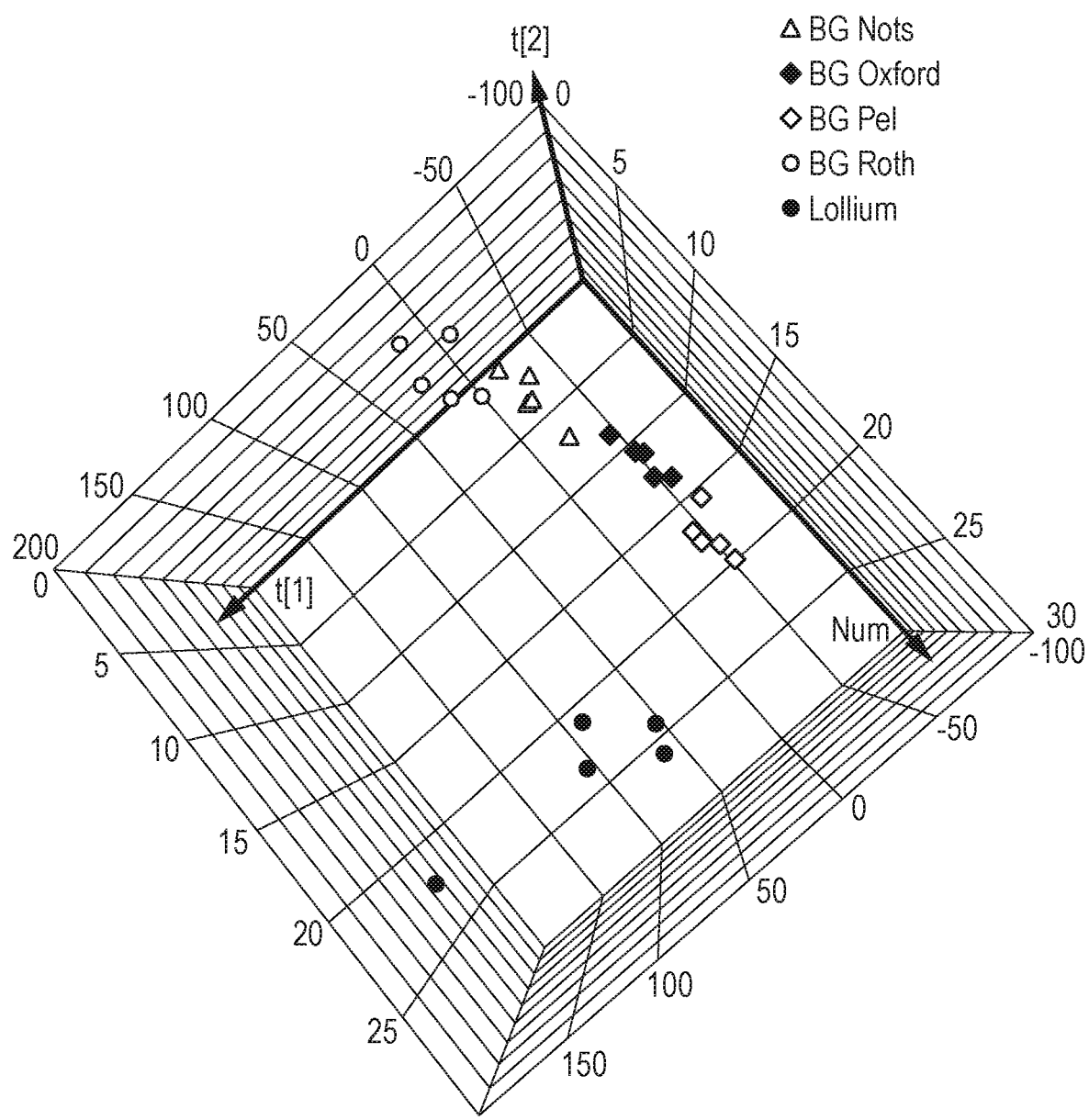
FIG. 6 shows results of Example 1; Shown is a PCA plot with pareto scaling; BG Nots stands for black grass Nottingham; BG Oxfor stands for black grass Oxford; BG Pel stands for black grass Pellium; BG Roth stands for black grass Rothamsted; and Lollium stands for rye grass Lollium rigidum.

FIG. 6 highlights that the method may be used to distinguish between (i) multiple herbicide resistant; (ii) target site resistant; and (iii) wild type (herbicide sensitive) plants.

Figure 7:
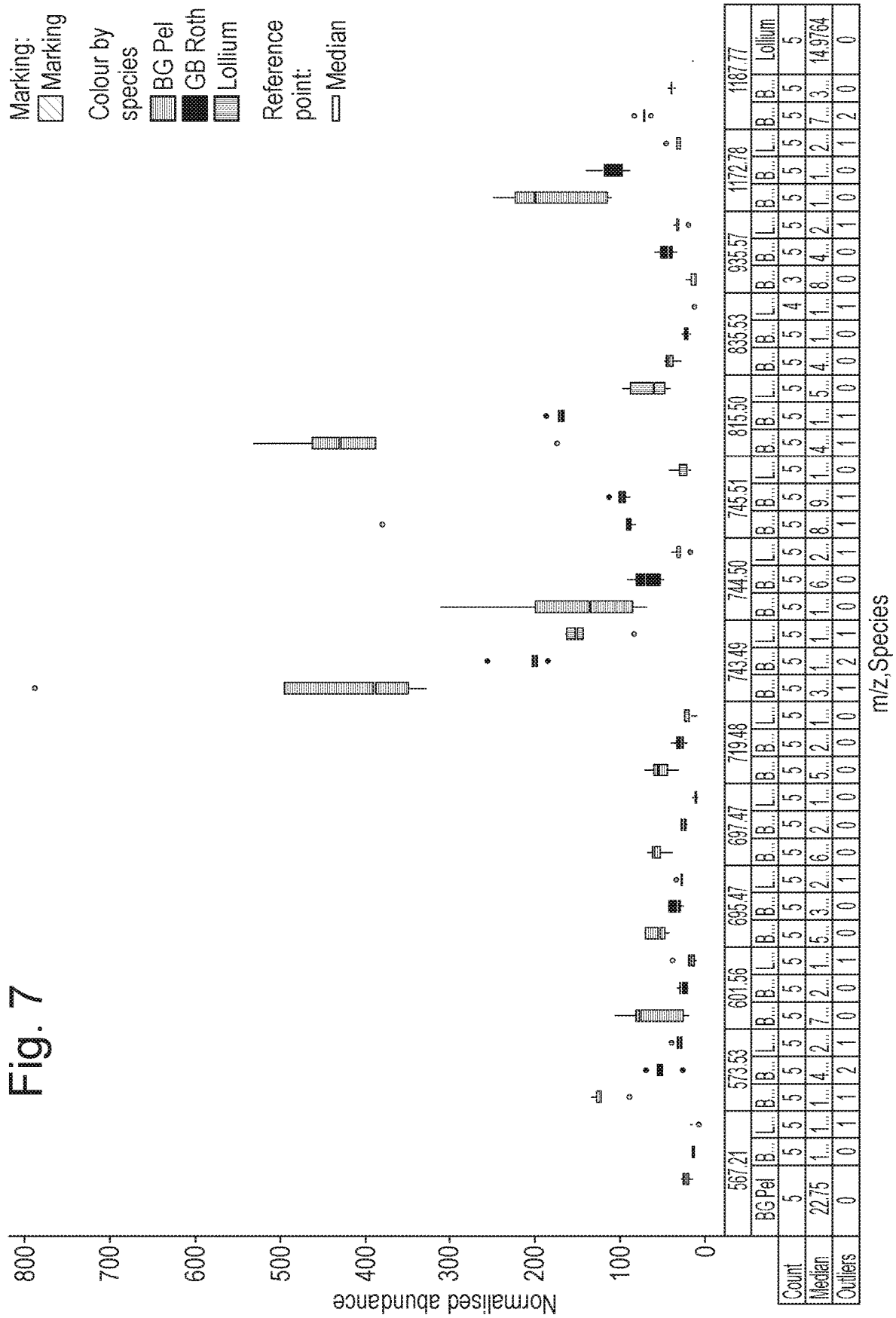
FIG. 7 shows certain phospholipids that were determined to be downregulated in multiple herbicide resistant black grass compared to wild type black grass; BG Pel stands for black grass Pellium; B . . . stands for black grass Rothamsted; and L . . . stands for Lollium rigidum; The relative abundance of various compounds denoted by their m/z (567.21 and so on) is shown for each of these species; The median is shown as a white line.

FIG. 7 shows certain phospholipids that were determined to be downregulated in multiple herbicide resistant black grass compared to wild type black grass. BG Pel stands for black grass Pellium; B . . . stands for black grass Rothamsted; and L . . . stands for Lollium rigidum. The relative abundance of various compounds denoted by their m/z (567.21 and so on) is shown for each of these species. The median is shown as a white line. The compound with m/z 719.48 is a PA(38:6), the compound with m/z 743.49 is a PG(34:3), the compound with m/z 744.50 is a PE(36:1), the compound with m/z of 754.51 is a PG(34:2) and the compound with m/z of 815.50 is a PG(P-41:8).

Figure 8A:
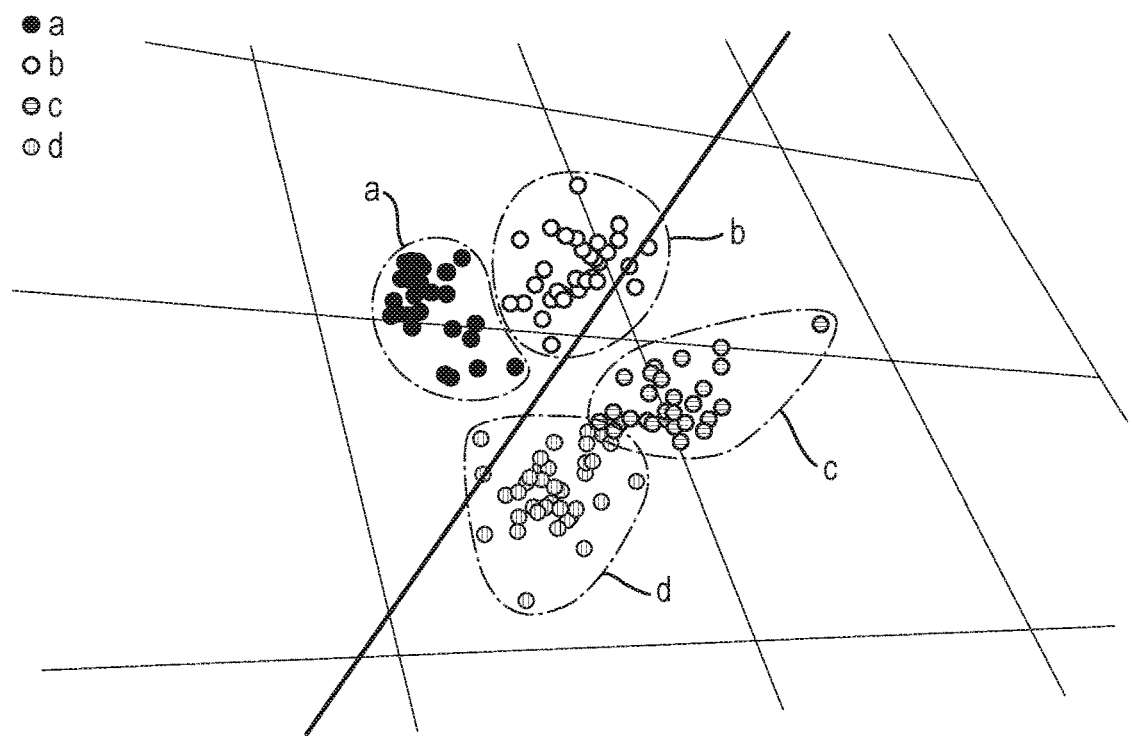
FIG. 8A-B shows results of Example 2; the original Figure and legend thereto is in colour, so the Figure is shown in clean format (FIG. 8B) and in annotated format (FIG. 8A); Shown is an LDA plot of white blotch control (marked a); white blotch drought (marked b), purple leaf drought (marked c) and purple leaf control (marked d)
Figure 8B:
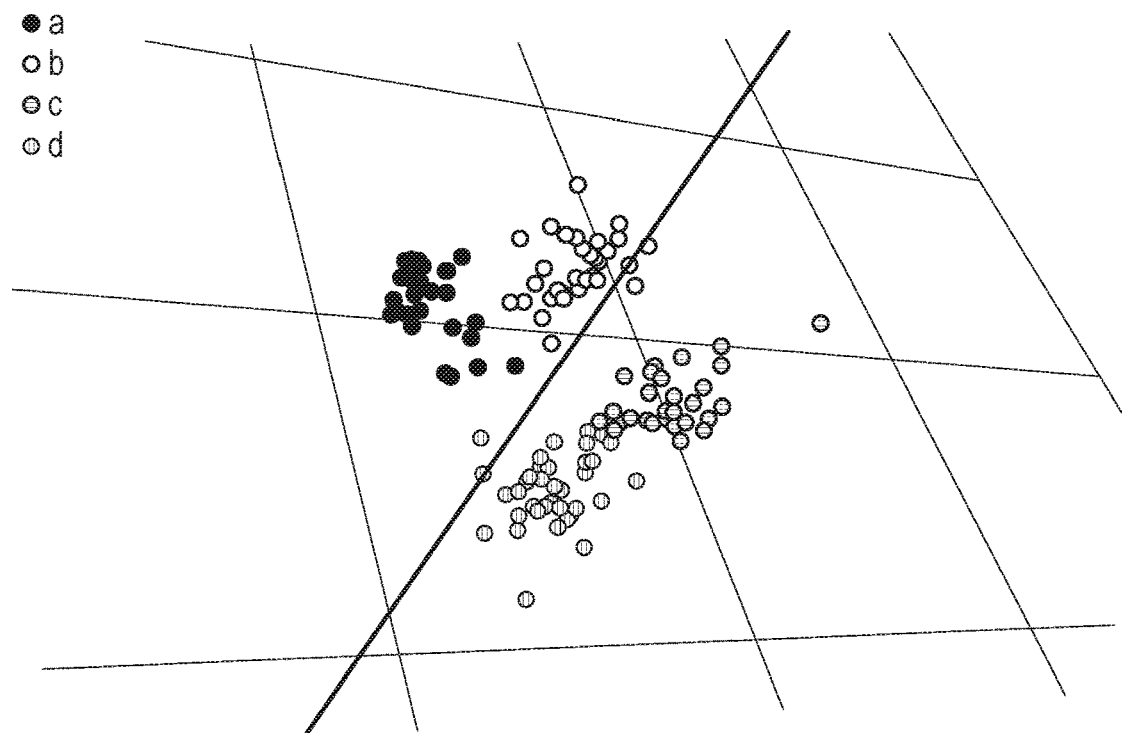

Example 2 Plant Phenotyping and Analysis of Drought Response Using REIMS Technology Analysis Pansies with 2 different genotypes and phenotypes, namely purple (ocean) or white blotch were either watered as normal (control) or exposed to drought. Leaves were either sampled in situ, i.e. on the plant, or removed from the plant prior to sampling. Sampling was carried out using bipolar forceps. The aerosol/smoke generated from the leaves was transferred to a mass spectrometer. MVA models were created using Principal Components Analysis (PCA) for data reduction followed by Linear Discriminant Analysis (LDA). As can be seen in FIG. 8A-B, the method allowed a distinction to be made between the purple and the white blotched genotypes and phenotypes. Moreover, the method allowed a distinction to be made between plant that had been watered and plants that had been exposed to drought.

Example 3 Analysis of Viral Infection

Virally-infected and healthy samples of leaves from a variety of different plant species were analysed.
Test Plants (Both Healthy and Infected Forms were Used)
1—paprika (species: Galga, *Capsicum* annum)
Infected with TSWV (tomato spotted wilt virus)
2—*Nicotiana benthamiana* Domin
2.1—Infected with TSWV (tomato spotted wilt virus)
2.2—Infected with a Cucumber Mosaic virus subspecies (mainly a cucumber mosaic virus, CMV, which contains fragments of peanut stunt virus, PSV) showing mainly CMV virus symptoms.
2.3—Infected with CMV RS isolate
3—*Nicotiana tabacum* L. cv. Xanthi nc
3.1—Infected with TSWV (tomato spotted wilt virus)
3.2—Infected with a Cucumber Mosaic virus subspecies (mainly a cucumber mosaic virus, CMV, which contains fragments of peanut stunt virus, PSV) showing mainly CMV virus symptoms.
4—*Phaseolus vulgaris* L. Minidor
4.1—Infected with CMV-Y. This virus systematically infects the plant
4.2—Infected with CMV-S. This virus only infects the leaves at the point of inoculation.
Instruments and settings used:
  Atmospheric Interface chamber: Waters interface, Direct IPA Setup
  Aesculight AE 10 IR Laser (10.6 μm)
  Smoke sampling tools: Tecan EVO 75
  MS: Waters Xevo G2-XS QTOF
  Solvent dosing: Leucine enkephaline with the flow rate of 0.20 mL/min.
  Aesculight Laser in CW P1 (Continous Wave) and SP A1 (Superpulse) mode were used.

All the leaves were burned on the superior side and the inferior side.

Figure 20:
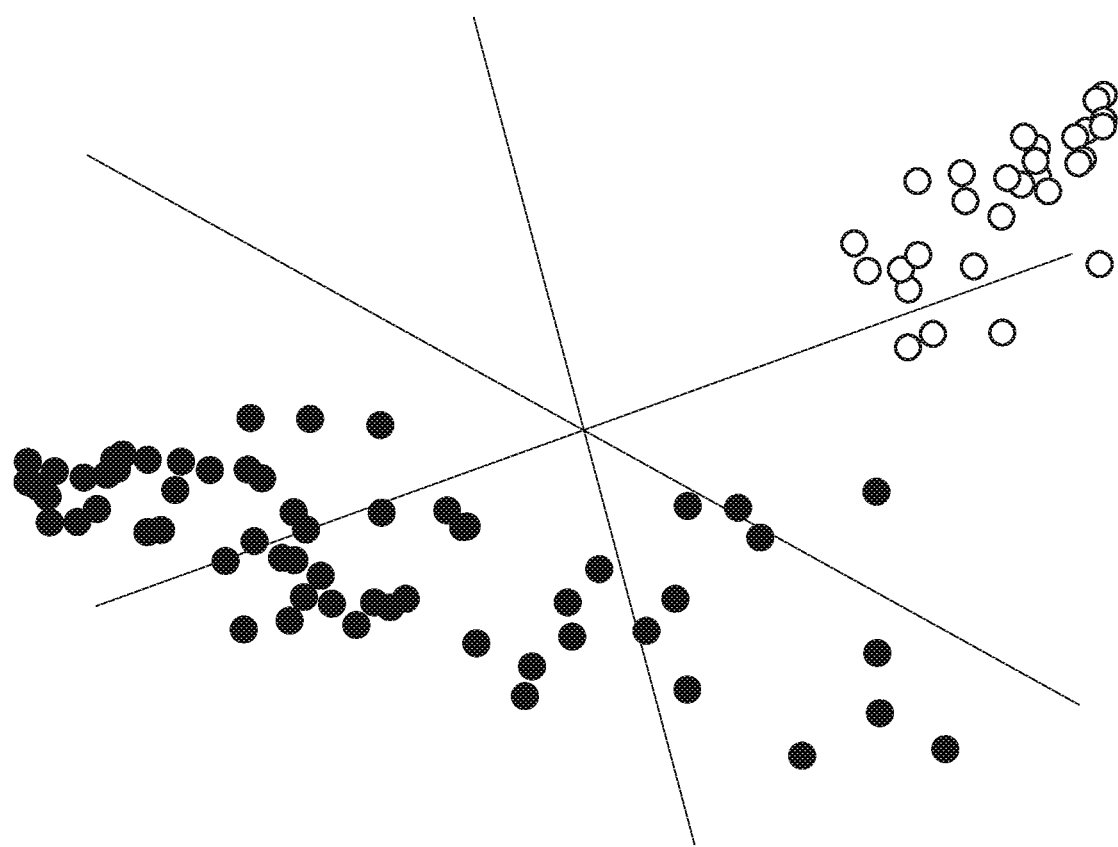
FIG. 20 shows results from Example 3, differentiating healthy leaf samples (empty circles) from infected leaf samples (filled circles)

An exemplary PCA plot is shows in FIG. 20, which illustrates that healthy parts of a leaf can be distinguished from virally infected ones.

Cross-validation was carried out. The cross-validation result was a correct classification rate of 100%, showing that infected leaves can be separated from healthy leaves, and the inferior and the superior part of the leaf can also be distinguished.

Conclusions

Infected and healthy plant leaves can be differentiated based on the REIMS fingerprint of the plant, using the statistical methods mentioned herein including Principal Component Analysis (PCA) and/or Linear Discriminant Analysis (LDA).

Although the spectral signal of the superior and inferior of the leaves is not identical, it does not interfere with the separation of infected and healthy leaves. Thus, the method may be used to detect and identify a biotic stress, such as a viral infection.

The fragmented species (MSMS spectra) suggest that there are glycerophospholipids in the signal from virally infected plants.

Example 4 Analysis of Fundal Infection

In order to assess the ability of rapid evaporative ionization mass spectrometry analysis to detect fungal infection of leaves, a visibly apparent model was chosen.
The Tar spot leaf disease is caused by the fungus *Rhytisma acerinum*, commonly seen on the leaves of the Sycamore tree though can also affect other acer species. REIMS analysis was conducted on the visible 'tar spots' as well as on apparent unaffected regions of the same leaf.

Sampling was carried out using Waters Synapt G2S with medimass REIMS source. No isopropyl alcohol dosing was used in this Example. Erbe surgical power supply with power set to 30 W and cut mode used. Wetting of the leaves was required in some instances.

Figure 21:
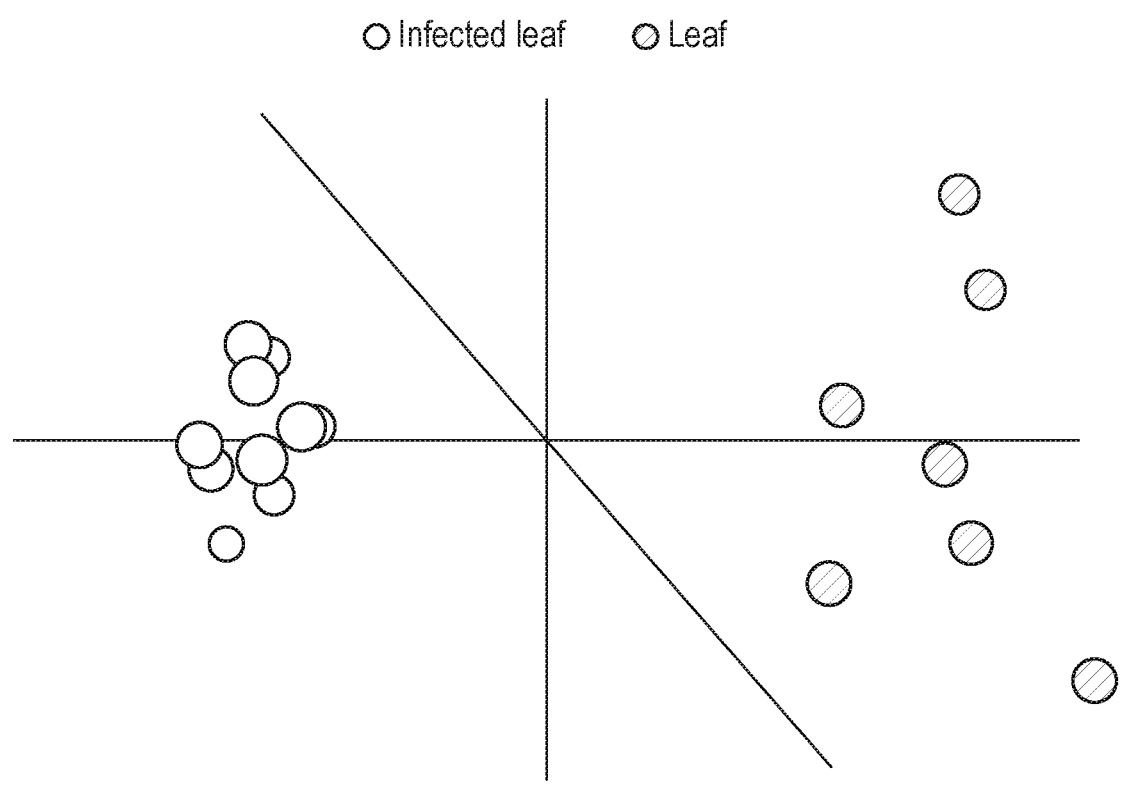
FIG. 21 shows results from Example 4. Principal component analysis demonstrating the separation of sampling points taken from the infected and uninfected regions of the sycamore leaves.

Spectra from the unaffected regions of multiple leaves were compared to those taken from the visible backspot regions. Upon the analysis of these spectra by unsupervised analysis technique—in this instance principal component analysis, the ability to differentiate these two components of the leaf was apparent, as shown in FIG. 21.

Thus, the multivariate separation was clear between the two regions. The spectrum of the infected area was determined to have a distinct chemical signature, particularly in the m/z 50-1200 range. Many of the differences between the infected and uninfected regions appear to be lipid species within the spectra that are related to the cellular components of the fungus present in the leaf, whilst the spectra from the unaffected regions much more closely resembles spectra taken from a range of other plant samples.

The invention claimed is:

1. A method of analysis using mass spectrometry and/or ion mobility spectrometry comprising:
  (a) using a first device to generate smoke, aerosol or vapour from a target plant material, wherein the first device is a rapid evaporation ionization mass spectrometry ("REIMS") device;
  (b) mass analysing and/or ion mobility analysing said smoke, aerosol or vapour, or ions derived therefrom, in order to obtain spectrometric data; and
  (c) analysing said spectrometric data in order to identify and/or characterise said plant material.

2. A method according to claim 1, wherein the step of analysing comprises analysing said spectrometric data in order to (i) analyse the identity of said plant material; (ii) analyse the genotype and/or phenotype of said plant material; (iii) analyse the susceptibility and/or response of said plant material to an abiotic or biotic stress; (iv) analyse the effect of manipulating the genotype and/or phenotype of said plant material; (v) analyse the production of a compound by said plant material; (vi) analyse the utilisation of a substance by said plant material; (vii) analyse the viability of said plant material; (viii) analyse the disease and/or stress state of said plant material; and/or (ix) analyse a compound or biomarker in said plant material.

3. A method according to claim 1, wherein the step of analysing comprises analysing said spectrometric data in order to determine and/or monitor the susceptibility and/or response of said plant material to an abiotic or biotic stress selected from exposure to (i) one or more herbicides; (ii) drought; (iii) high salinity; (iv) water logging; (v) radiation; (vi) nutrient and/or mineral deficiency; (vii) pesticides; (viii) toxins; (ix) heat; (x) frost; (xi) alkaline or acidic conditions; (xii) a virus; and/or (xiii) a fungus.

4. A method according to claim 3, wherein said method comprises exposing the target plant material to an abiotic and/or biotic stress prior to the using of the first device to generate smoke, aerosol or vapour from the target plant material.

5. A method according to claim 1, wherein said plant material is:
  a member of the grass family such as wheat, rice, corn, rye, barley, oat, sorghum, wild rice, and/or millet; or mutant and/or transgenic or comprises mutant and/or transgenic cells; or diseased and/or stressed.

6. A method according to claim 1, wherein said method comprises analysing said spectrometric data in order to analyse the effect of a genotype and/or phenotype manipulation on the susceptibility and/or response of a plant material to an abiotic and/or biotic stress.

7. A method according to claim 1, comprising analysing said spectrometric data in order to analyse the stress and/or disease state of said plant material and further comprising a step of determining whether the growth conditions of said plant material should be altered.

8. A method as claimed in claim 1, comprising analysing said spectrometric data to determine the presence and/or absence of one or more compounds and/or one or more biomarkers in or on said plant material.

9. A method according to claim 1, comprising determining based upon said spectrometric data that one or more glycerophospholipids are expressed at a lower level relative to a predetermined level and based upon said determination determining that said plant material is resistant to one or more herbicides.

10. A method according to claim 9, wherein said glycerophospholipids are selected from one or more of PA(38:6), PG(34:3), PE(36:1), PG(34:2) and PG(P-41:8).

11. A method according to claim 1, wherein said target plant material is a first target sample and said spectrometric data is first spectrometric data; and wherein the method further comprises generating aerosol, smoke or vapour from a second, different target plant material sample; mass analysing and/or ion mobility analysing the aerosol, smoke or vapour generated from the second target sample, or ions derived therefrom, so as to obtain second spectrometric data; and comparing the first and second spectrometric data to determine differences between the first and the second target samples.

12. A method according to claim 11, wherein said first target sample and said second target sample are samples from a first and second separate plant material, wherein
  (i) said first plant material was exposed to a first abiotic or biotic stress factor and said second plant material was not exposed to said first abiotic or biotic stress factor, and said method comprises analysing said first and second spectrometric data to analyse the effect of said first abiotic or biotic stress factor on the first plant material; or
  (ii) said second plant material was exposed to a second abiotic or biotic stress factor and said first plant material was not exposed to said second abiotic or biotic stress factor, and said method comprises analysing said first and second spectrometric data to analyse the effect of said second abiotic or biotic stress factor on the second plant material.

13. A method according to claim 11, wherein said first target sample and said second target sample are samples taken from a single plant material at a first time and a subsequent second time respectively, wherein said plant material was exposed to a first abiotic or biotic stress factor after said first sample was obtained but before said second sample was obtained, and the method comprises analysing said first and second spectrometric data to analyse the effect of said first abiotic or biotic stress factor on said plant material.

14. The method of claim 1, comprising using the first device to generate aerosol, smoke or vapour from multiple different regions on the target, and comprising mass analysing and/or ion mobility analysing said aerosol, smoke, vapour or ions derived therefrom generated at each of said different regions so as to obtain said spectrometric data for the different regions, and correlating the spectrometric data to its respective region on the target so as to provide ion imaging or map data for the target.

15. A method according to claim 1, wherein said step of using said first device to generate aerosol, smoke or vapour from said target plant material comprises contacting said target plant material with one or more electrodes and applying an AC or RF voltage to said one or more electrodes in order to generate said aerosol, smoke or vapour.

16. A method as claimed in claim 1, comprising causing said aerosol, smoke or vapour, or analyte therein, to impact upon a collision surface so as to generate said ions derived from the aerosol, smoke or vapour.

17. Apparatus comprising: (a) a first device for generating smoke, aerosol or vapour from a target plant material, wherein the first device is a rapid evaporation ionization mass spectrometry ("REIMS") device; (b) a mass spectrometer and/or ion mobility spectrometer for analysing said smoke, aerosol or vapour, or ions derived therefrom, in order to obtain spectrometric data; and (c) a processor adapted to analyse said spectrometric data in order to identify and/or characterise said target plant material.

18. An apparatus comprising: (a) a first device for generating smoke, aerosol or vapour from a target plant material, wherein the first device is a rapid evaporation ionization mass spectrometry ("REIMS") device; (b) a mass spectrometer and/or ion mobility spectrometer for analysing said smoke, aerosol or vapour, or ions derived therefrom, in order to obtain spectrometric data; and (c) a processor adapted to analyse said spectrometric data in order to identify and/or characterise said target plant material, wherein the apparatus is arranged and adapted to perform the method of claim 1.

19. A method of analysis using mass spectrometry and/or ion mobility spectrometry comprising:
  (a) using a first device to generate smoke, aerosol or vapour from a target plant material, wherein said step of using said first device to generate aerosol, smoke or vapour from said target plant material comprises contacting said target plant material with one or more electrodes and applying an AC or RF voltage to said one or more electrodes in order to generate said aerosol, smoke or vapour;
  (b) mass analysing and/or ion mobility analysing said smoke, aerosol or vapour, or ions derived therefrom, in order to obtain spectrometric data; and
  (c) analysing said spectrometric data in order to identify and/or characterise said plant material.

* * * * *